(12) United States Patent
Kobayashi et al.

(10) Patent No.: US 7,767,651 B2
(45) Date of Patent: Aug. 3, 2010

(54) SPIROKETAL DERIVATIVES AND USE THEREOF AS DIABETIC MEDICINE

(75) Inventors: Takamitsu Kobayashi, Gotenba (JP); Tsutomu Sato, Gotenba (JP); Masahiro Nishimoto, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 369 days.

(21) Appl. No.: 11/815,074

(22) PCT Filed: Jan. 27, 2006

(86) PCT No.: PCT/JP2006/301284

§ 371 (c)(1),
(2), (4) Date: Jul. 30, 2007

(87) PCT Pub. No.: WO2006/080421

PCT Pub. Date: Aug. 3, 2006

(65) Prior Publication Data

US 2009/0030006 A1    Jan. 29, 2009

(30) Foreign Application Priority Data

Jan. 28, 2005 (JP) .............................. 2005-020901
Jun. 16, 2005 (JP) .............................. 2005-176690

(51) Int. Cl.
*A01N 43/04* (2006.01)
*C07H 1/00* (2006.01)
*C07H 3/00* (2006.01)
*C08B 37/00* (2006.01)

(52) U.S. Cl. ......................................... 514/23; 536/1.11

(58) Field of Classification Search ........................ None
See application file for complete search history.

(56) References Cited

U.S. PATENT DOCUMENTS

| | | | |
|---|---|---|---|
| 5,424,406 A | 6/1995 | Tsujihara et al. | |
| 6,048,842 A | 4/2000 | Tsujihara et al. | |
| 2001/0041674 A1 | 11/2001 | Tomiyama et al. | |
| 2002/0137903 A1 | 9/2002 | Ellsworth et al. | |
| 2003/0114390 A1 | 6/2003 | Washburn et al. | |
| 2004/0138439 A1 | 7/2004 | Deshpande et al. | |
| 2005/0233988 A1 | 10/2005 | Nomura et al. | |

FOREIGN PATENT DOCUMENTS

| | | |
|---|---|---|
| EP | 0 598 359 A1 | 5/1994 |
| EP | 0 684 254 A1 | 11/1995 |
| EP | 1 500 403 A1 | 1/2005 |
| JP | 6-199886 A | 7/1994 |
| JP | 8-27006 A | 1/1996 |
| JP | 9-124684 A | 5/1997 |
| JP | 9-124685 A | 5/1997 |
| JP | 9-188625 A | 7/1997 |
| JP | 10-237089 A | 9/1998 |
| JP | 2000-80041 A | 3/2000 |
| JP | 2003-12686 A | 1/2003 |
| JP | 2004-359630 A | 12/2004 |
| JP | 2005-247834 A | 9/2005 |
| WO | 01/16147 A1 | 3/2001 |
| WO | 01/27128 A1 | 4/2001 |
| WO | 01/68660 A1 | 9/2001 |
| WO | 01/74834 A1 | 10/2001 |
| WO | 01/74835 A1 | 10/2001 |
| WO | 02/28872 A1 | 4/2002 |
| WO | 02/36602 A1 | 5/2002 |
| WO | 02/44192 A1 | 6/2002 |
| WO | 02/053573 A1 | 7/2002 |
| WO | 02/064606 A1 | 8/2002 |
| WO | 02/068439 A1 | 9/2002 |
| WO | 02/068440 A1 | 9/2002 |
| WO | 02/083066 A3 | 10/2002 |

(Continued)

OTHER PUBLICATIONS

Stella, "Prodrugs as Therapeutics", Expert Opinion Ther. Patents (2004) 14(3), pp. 277-280.*

(Continued)

*Primary Examiner*—Traviss C McIntosh, III
(74) *Attorney, Agent, or Firm*—Browdy and Neimark, PLLC

(57) ABSTRACT

The present invention provides a compound of Formula (I):

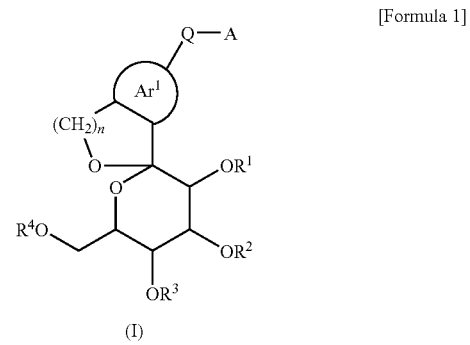

(I)

wherein $R^1$, $R^2$, $R^3$ and $R^4$ are each independently selected from a hydrogen atom, an optionally substituted $C_1$-$C_6$ alkyl group, an optionally substituted $C_7$-$C_{14}$ aralkyl group and —C(=O)Rx; Rx represents an optionally substituted $C_1$-$C_6$ alkyl group, an optionally substituted aryl group, an optionally substituted heteroaryl group, an optionally substituted $C_1$-$C_6$ alkoxy group or —NReRf; $Ar^1$ represents an optionally substituted aromatic carbocyclic ring or an optionally mono-substituted aromatic heterocyclic ring; Q represents —$(CH_2)_m$-$(L)_p$- or -$(L)_p$-$(CH_2)_m$—; m represents an integer selected from 0 to 2, n represents an integer selected from 1 and 2, and p represents an integer selected from 0 and 1; L represents —O—, —S— or —$NR^5$—; and A represents an optionally substituted aryl group or an optionally substituted heteroaryl group, a prodrug thereof and a pharmaceutically acceptable salt thereof, as well as a pharmaceutical preparation or pharmaceutical composition comprising such a compound.

17 Claims, No Drawings

FOREIGN PATENT DOCUMENTS

| | | |
|---|---|---|
| WO | 02/088157 A1 | 11/2002 |
| WO | 02/098893 A1 | 12/2002 |
| WO | 03/000712 A1 | 1/2003 |
| WO | 03/011880 A1 | 2/2003 |
| WO | 03/020737 A1 | 3/2003 |
| WO | 03/090783 A1 | 11/2003 |
| WO | 03/099836 A1 | 12/2003 |
| WO | 2004/007517 A1 | 1/2004 |
| WO | 2004/013118 A1 | 2/2004 |
| WO | 2004/014931 A1 | 2/2004 |
| WO | 2004/052902 A1 | 6/2004 |
| WO | 2004/052903 A1 | 6/2004 |
| WO | 2004/058790 A1 | 7/2004 |
| WO | 2004/080990 A1 | 9/2004 |
| WO | 2004/087727 A1 | 10/2004 |
| WO | 2004/089967 A1 | 10/2004 |
| WO | 2004/099230 A1 | 11/2004 |
| WO | 2004/113359 A1 | 12/2004 |
| WO | 2005/011592 A2 | 2/2005 |
| WO | 2005/012242 A2 | 2/2005 |
| WO | 2005/012243 A2 | 2/2005 |
| WO | 2005/012318 A2 | 2/2005 |
| WO | 2005/012321 A1 | 2/2005 |
| WO | 2005/012326 A1 | 2/2005 |
| WO | 2005/021566 A2 | 3/2005 |
| WO | 2005/038013 A1 | 4/2005 |
| WO | 2005/042552 A2 | 5/2005 |
| WO | 2005/063785 A2 | 7/2005 |
| WO | 2005/085237 A1 | 9/2005 |
| WO | 2005/085265 A1 | 9/2005 |
| WO | 2005/085267 A1 | 9/2005 |
| WO | 2005/092877 A1 | 10/2005 |
| WO | 2005/095372 A1 | 10/2005 |
| WO | 2005/095373 A1 | 10/2005 |
| WO | 2005/095429 A1 | 10/2005 |
| WO | 2005/121161 A1 | 12/2005 |
| WO | 2006/002912 A1 | 1/2006 |
| WO | 2006/008038 A1 | 1/2006 |

OTHER PUBLICATIONS

Adachi et al., Metabolism, vol. 49, No. 8, 2000, 990-995.*
Danishefsky, Samuel et al., A fully synthetic route to the papulacandins. Stereospecific spiroacetalization of a C-1-arylated methylglycoside, carbohydrate Research, 1987, 171, 317-327, particularly.
Ahmed, Md. Moinuddin et al., De novo synthesis of a glacto-papulacandin moiety via aniterative dihyroxylation strategy, Tetrahedron Letters, 2005 46(24), 4151-4155, particularly, p. 4152, 1d.
Y. Kinai et al., "The Human Kidney Low Affinity Na+/glucose Cotransporter SGLT2", J. Clin. Invest., vol. 93, pp. 397-404, Jan. 1994.
K. Tsujihara et al., "Na+ -Glucose Cotransporter Inhibitors as Antidiabetics. I. Synthesis and Pharmacological Properties of 4'-Dehydroxyphlorizin Derivatives Based on a New Concept", Chem. Pharm. Bull. vol. 44, No. 6, pp. 1174-1180, 1996.
M. Hongu et al., "Na+ -Glucose Cotransporter Inhibitors as Antidiabetic Agents. III. Synthesis and Pharmacological Properties of 4'-Dehydroxyphlorizin Derivatives Modified at the OH Groups of the Glucose Moiety", Chem. Pharm. Bull. vol. 46, No. 10, pp. 1545-1555, 1998.
M. Hongu et al., "Na+ -Glucose Cotransporter Inhibitors as Antidiabetic Agents. II. Synthesis and Structure-Activity Relationships of 4'-Dehydroxyphlorizin Derivatives", Chem. Pharm. Bull. vol. 46, No. 1, pp. 22-33, 1998.
K. Tsujihara et al., "Na+ -Glucose Cotransporter (SGLT) Inhibitors as Antidiabetic Agents. 4. Synthesis and Pharmacological Properties of 4'-Dehydroxyphlorizin Derivatives Substituted on the B Ring", J. Med. Chem. vol. 42, pp. 5311-5324, 1999.
Nippon Rinsho, vol. 60, Suppl. 9, pp. 588-593, 2002. (Japanese literature refers to a pharmacological mechanism of SGLT inhibitor, which was being developed as a medicament for treating diabetes, and to pharmacological effects of T-1095 that was known as an SGLT inhibitor.).
J. T. Link et al., "A method for preparing C-glycosides related to phlorizin", Tetrahedron Letters, vol. 41, pp. 9213-9217, 2000.
K. Ohsumi et al., "Pyrazole-O-Glucosides as Novel Na+ -Glucose Cotransporter (SGLT) Inhibitors", Biorg. Med. Chem. Letters, vol. 13, pp. 2269-2272, 2003.
S. Danishefsky et al., "A fully synthetic route to the papulacandins. Stereo-specific spiroacetalization of a C-1-arylated methyl glycoside", Carbohydrate Research, vol. 171, pp. 317-327, 1987.
W. Oldendorf et al., "Rapid, Transient Drop in Brain Glucose After Intravenous Phloretin or 3-0-Methyl-D-Glucose", Stroke, vol. 14, No. 3, pp. 388-393, May-Jun. 1983.
Md. Moinuddin and G. A. O'Doherty, "De novo synthesis of a galacto-papulacandin moiety via an iterative dihydroxylation strategy", Tetrahedron Letters, vol. 46, pp. 4151-4155, 2005.
Crernecki,Stanislas et al, "C-Glycosides. 9. Stereospecific Synthesis of C-Glycosidic Spiroketal of the Papulacandins" J. Org. Chem., vol. 56, No. 22, pp. 6289-6292 (1991).

* cited by examiner

SPIROKETAL DERIVATIVES AND USE THEREOF AS DIABETIC MEDICINE

TECHNICAL FIELD

The present invention relates to pharmaceutically useful spiroketal derivatives, prodrugs thereof and pharmaceutically acceptable salts thereof. Particularly, the present invention relates to spiroketal derivatives and prodrugs thereof and salts thereof, which are useful as prophylactic or therapeutic agents for hyperglycemia-induced diseases such as diabetes including insulin-dependent diabetes mellitus (type I diabetes) and non-insulin-dependent diabetes mellitus (type II diabetes), diabetic complications and obesity, because of their ability to inhibit $Na^+$-glucose cotransporter 2 (SGLT2).

BACKGROUND ART

In recent years, the number of diabetic patients has increased due to westernized diets and a chronic lack of exercise, etc. In diabetic patients, chronic hyperglycemia causes reductions in both insulin secretion and insulin sensitivity, which in turn will cause elevation of blood glucose levels and lead to exacerbation of symptoms. Drugs conventionally used as therapeutic agents for diabetes include biguanides, sulfonylureas, glycosidase inhibitors and insulin-resistance improving agents. However, adverse side effects of these drugs have been reported; for example, lactic acidosis for biguanides, hypoglycemia for sulfonylureas, and diarrhea for glycosidase inhibitors. It is now strongly desired to develop therapeutic agents for diabetes that depend on a new mechanism of action which is different from those conventionally proposed.

Phloridzin, a naturally-occurring glucose derivative, is reported to produce a hypoglycemic effect by inhibiting sodium-dependent glucose cotransporter 2 (SGLT2) present at the S1 site of renal proximal tubules resulting in inhibiting excessive glucose reabsorption in the kidney and in accelerating the glucose excretion (see Nonpatent Document 1). Until now, an increasing number of studies have been conducted to develop therapeutic agents for diabetes that depend on SGLT2 inhibition.

For example, compounds used as SGLT2 inhibitors are reported in JP 2000-080041 A (Patent Document 1), International Publication No. WO01/068660 (Patent Document 2), International Publication No. WO04/007517 (Patent Document 3) and so on. However, phloridzin and the compounds disclosed in these patent applications have a problem in that, when administered orally, they are readily hydrolyzed by the action of glycosidase or the like present in the small intestine, and hence rapidly lose their pharmacological effects. Moreover, in the case of phloridzin, its aglycon phloretin is reported to strongly inhibit sugar transporters of the facilitated diffusion type. For example, there is a report showing that phloretin produces an adverse effect of reducing intracerebral glucose levels when intravenously administered to rats (see, e.g., Nonpatent Document 2).

For these reasons, attempts have been made to convert these compounds into their prodrug forms with the aim of avoiding such digestion problems and improving absorption efficiency. However, although it is desired that prodrugs when administered are precisely metabolized into active compounds in or near their target organs, stable effects are often difficult to achieve due to the action of various metabolic enzymes present in the body and large variations among individuals. Other attempts have also been made to replace glycosidic linkages in these compounds by carbon-carbon linkages (see Patent Documents 4 to 8). However, there still remains a demand for further improvements in their pharmaceutical properties, including activity and metabolic stability.

Patent Document 1: Japanese Patent Publication 2000-080041 A
Patent Document 2: International Publication No. WO01/068660 Pamphlet
Patent Document 3: International Publication No. WO04/007517 Pamphlet
Patent Document 4: US Patent Publication 2001/041674 A
Patent Document 5: US Patent Publication 2002/137903 A
Patent Document 6: International Publication No. WO01/027128 Pamphlet
Patent Document 7: International Publication No. WO02/083066 Pamphlet
Patent Document 8: International Publication No. WO04/013118 Pamphlet
Non-patent Document 1: J. Clin. Invest., 93, 397 (1994)
Non-patent Document 2: Stroke, 14, 388 (1983)

DISCLOSURE OF THE INVENTION

Problems to be Solved by the Invention

An object of the present invention is to provide a spiroketal derivative having pharmaceutically preferred properties. Particularly, the present invention aims to provide a spiroketal derivative having a hypoglycemic effect and further having pharmaceutically preferred properties such as prolonged efficacy, metabolic stability or safety. Another object of the present invention is to provide a pharmaceutical composition used for prevention or treatment of hyperglycemia-induced diseases such as diabetes including insulin-dependent diabetes mellitus (type I diabetes) and non-insulin-dependent diabetes mellitus (type II diabetes), diabetic complications and obesity.

Measure to Solve the Problems

As a result of extensive and intensive efforts made to achieve the objects stated above, the inventors of the present invention have found that a spiroketal derivative of Formula (I) has excellent inhibitory activity against SGLT2. This finding led to the completion of the present invention.

Namely, according to one aspect of the present invention, there is provided a compound of Formula (I):

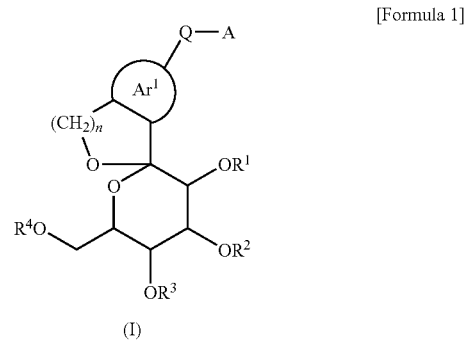

[Formula 1]

(I)

wherein $R^1$, $R^2$, $R^3$ and $R^4$ are each independently selected from a hydrogen atom, a $C_1$-$C_6$ alkyl group which may be substituted with one or more Ra, a $C_7$-$C_{14}$ aralkyl group which may be substituted with one or more Rb, and —C(=O)Rx;

Rx represents a $C_1$-$C_6$ alkyl group which may be substituted with one or more Ra, an aryl group which may be substituted with one or more Rb, a heteroaryl group which may be substituted with one or more Rb, a $C_1$-$C_6$ alkoxy group which may be substituted with one or more Ra, or —NReRf;

$Ar^1$ represents an aromatic carbocyclic ring which may be substituted with one or more Rb, or an aromatic heterocyclic ring which may be substituted with one or more Rb;

Q represents —$(CH_2)_m$-$(L)_p$- or -$(L)_p$-$(CH_2)_m$—;

m represents an integer selected from 0 to 2, n represents an integer selected from 1 and 2, and p represents an integer selected from 0 and 1;

L represents —O—, —S— or —$NR^5$—, $R^5$ is selected from a hydrogen atom, a $C_1$-$C_6$ alkyl group which may be substituted with one or more Ra, and —C(=O)Rx;

A represents an aryl group which may be substituted with one or more Rb or a heteroaryl group which may be substituted with one or more Rb, wherein the aryl group or the heteroaryl group may form a condensed ring together with the aromatic carbocyclic ring or the aromatic heterocyclic ring;

Ra is independently selected from a halogen atom, a hydroxyl group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkoxycarbonyl group which may be substituted with one or more Rc, and a $C_1$-$C_6$ alkylcarbonyl group which may be substituted with one or more Rc;

Rb is independently selected from a $C_1$-$C_6$ alkyl group which may be substituted with one or more Rc, a $C_3$-$C_8$ cycloalkyl group which may be substituted with one or more Rc, a $C_2$-$C_6$ alkenyl group which may be substituted with one or more Rc, a $C_2$-$C_6$ alkynyl group which may be substituted with one or more Rc, a $C_7$-$C_{14}$ aralkyl group which may be substituted with one or more Rd, a halogen atom, a hydroxyl group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkylcarbonyl group which may be substituted with one or more Rc, a $C_1$-$C_6$ alkoxycarbonyl group which may be substituted with one or more Rc, a $C_1$-$C_3$ alkylenedioxy group, a heterocyclyl group, and a heterocyclyloxy group;

Rc is independently selected from a halogen atom, a hydroxyl group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamino group, and a di-($C_1$-$C_6$ alkyl)amino group;

Rd is independently selected from a $C_1$-$C_6$ alkyl group which may be substituted with one or more halogen atoms, a $C_7$-$C_{14}$ aralkyl group, a halogen atom, a hydroxyl group, a cyano group, a nitro group, an amino group, a $C_1$-$C_6$ alkylamino group, and a di-($C_1$-$C_6$ alkyl)amino group;

Re represents a hydrogen atom, a $C_1$-$C_6$ alkyl group which may be substituted with one or more Rc, an aryl group which may be substituted with one or more Rd, or a heteroaryl group which may be substituted with one or more Rd;

Rf represents a hydrogen atom or a $C_1$-$C_6$ alkyl group which may be substituted with one or more Rc; and Rg represents a hydrogen atom, a $C_1$-$C_6$ alkyl group which may be substituted with Rc, a $C_1$-$C_6$ alkylcarbonyl group which may be substituted with one or more Rc, an aryl group which may be substituted with one or more Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc, or Re and Rf, or Rf and Rg may form a 4- to 7-membered heterocyclic ring together with the nitrogen atom to which they are attached, or a prodrug thereof, or a pharmaceutically acceptable salt thereof.

According to another aspect of the present invention, there is provided a compound of Formula (Ia):

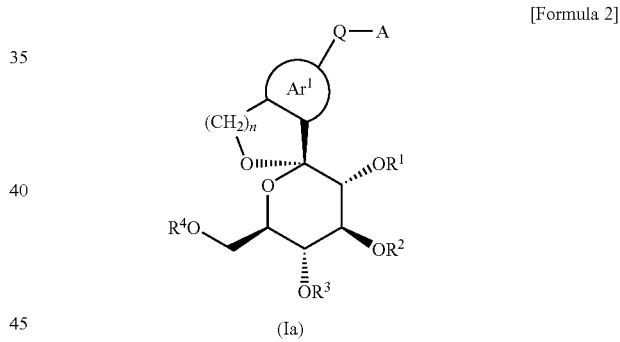

[Formula 2]

(Ia)

wherein $Ar^1$, Q, n, $R^1$, $R^2$, $R^3$, $R^4$ and A are as defined above, or a prodrug thereof, or a pharmaceutically acceptable salt thereof.

In the present invention, $Ar^1$ is preferably a benzene ring or a thiophene ring (each of which may be substituted with one or more Rb). Likewise, m is preferably 1, and n is preferably 1. Moreover, $R^1$, $R^2$, $R^3$ and $R^4$ are each independently selected from a hydrogen atom and —C(=O)Rx, and Rx is preferably a $C_1$-$C_6$ alkyl group which may be substituted with one or more Ra, or a $C_1$-$C_6$ alkoxy group which may be substituted with one or more Ra.

In a preferred substitution mode, $Ar^1$ has a substituent —$(CH_2)_m$-A on its ring atom that is 2 atoms apart from the ring atom directly attached to the substituted glucitol group. For example, when $Ar^1$ is a benzene ring, a meta-substituted form is preferred; when $Ar^1$ is a pyridine ring, a 2,4-substituted, 3,5-substituted or 2,6-substituted form is preferred. Alternatively, when $Ar^1$ is a thiophene ring, a 2,5-substituted or 3,5-substituted form is preferred. The substituted glucitol group and the substituent —(CH$_2$)$_m$-A may be attached to a ring nitrogen atom.

According to yet another aspect of the present invention, there is provided a compound of Formula (Ib):

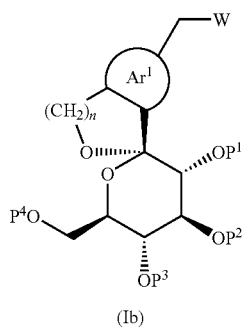

[Formula 3]

(Ib)

wherein n represents an integer selected from 1 and 2;

Ar$^1$ represents an aromatic carbocyclic ring which may be substituted with one or more Rb, or an aromatic heterocyclic ring which may be substituted with one or more Rb;

W represents —O—Z or a halogen atom;

Z represents a hydrogen atom, an acyl group or a benzyl group;

P$^1$, P$^2$, P$^3$ and P$^4$ are each independently selected from a hydrogen atom, an acyl group or a benzyl group; and Rb is as defined above. This compound is useful, for example, as a synthetic intermediate for the compound of the present invention represented by Formula (I). As used herein, the term "acyl group" is a common name for groups represented by RCO— and encompasses a formyl group, a C$_1$-C$_6$ alkylcarbonyl group (e.g., an acetyl group, a propionyl group), an arylcarbonyl group (e.g., a benzoyl group, a naphthoyl group), a C$_7$-C$_{14}$ aralkylcarbonyl group (e.g., a benzylcarbonyl group) and so on.

According to yet another aspect of the present invention, there is provided a pharmaceutical composition for use as an Na$^+$-glucose cotransporter inhibitor, which comprises a compound of the above Formula (I) or (Ia) or a prodrug thereof, or a pharmaceutically acceptable salt thereof.

According to yet another aspect of the present invention, there is provided a pharmaceutical composition for use in preventing or treating diabetes (e.g., insulin-dependent diabetes mellitus (type I diabetes) or non-insulin-dependent diabetes mellitus (type II diabetes)) or hyperglycemia, diabetic complications induced thereby, or obesity, which comprises a compound of the above Formula (I) or (Ia) or a prodrug thereof, or a pharmaceutically acceptable salt thereof.

According to yet another aspect of the present invention, there is provided a method for preventing or treating diabetes (e.g., insulin-dependent diabetes mellitus (type I diabetes) or non-insulin-dependent diabetes mellitus (type II diabetes)), hyperglycemia-induced diabetic complications or obesity, which comprises administering to a patient a therapeutically effective amount of a compound of the above Formula (I) or (Ia) or a prodrug thereof, or a pharmaceutically acceptable salt thereof.

In the above Formulae (I) and (Ia), groups defined as R$^1$, R$^2$, R$^3$ and R$^4$ include, for example, a hydrogen atom, a C$_1$-C$_6$ alkyl group, a C$_1$-C$_6$ alkoxy-C$_1$-C$_6$ alkyl group, a C$_7$-C$_{14}$ aralkyl group, a C$_1$-C$_6$ alkylcarbonyl group, a C$_7$-C$_{14}$ aralkylcarbonyl group, a C$_1$-C$_6$ alkoxycarbonyl group, and a C$_7$-C$_{14}$ aralkyloxycarbonyl group. These groups may be substituted with one or more substituents which are each independently selected from a halogen atom, a hydroxyl group, a C$_1$-C$_6$ alkoxy group, a C$_1$-C$_6$ alkylcarbonyl group, a carboxyl group, an amino group and a substituted amino group, preferably each independently selected from a C$_1$-C$_6$ alkylcarbonyl group. A hydrogen atom is particularly preferred as R$^1$, R$^2$, R$^3$ and R$^4$.

In the above Formulae (I) and (Ia), Ar$^1$ may be substituted with the same or different 1 to 4 substituents, for example, which are each independently selected from a halogen atom; a hydroxyl group; a C$_1$-C$_6$ alkyl group, a C$_3$-C$_8$ cycloalkyl group, a C$_1$-C$_6$ alkoxy group and a C$_1$-C$_6$ alkylthio group (these 4 groups may be substituted with 1 to 4 substituents selected from a halogen atom, a hydroxyl group and an amino group); a methylenedioxy group; a cyano group; a C$_1$-C$_6$ alkylsulfonyl group; a C$_1$-C$_6$ alkylsulfonylamino group; a nitro group; a carboxyl group; a substituted amino group; and a 4- to 6-membered heterocyclyl group.

Among the groups defined as Ar$^1$, the aromatic carbocyclic ring preferably refers to an aromatic carbocyclic ring containing 5 to 6 carbon atoms, including a benzene ring. The aromatic heterocyclic ring preferably refers to a 5- to 6-membered aromatic heterocyclic group, including a pyrrole ring, a thiophene ring, a furan ring, a pyridine ring, a thiazole ring, an isothiazole ring, a pyrazole ring, an indazole ring, an oxazole ring, an isoxazole ring, an imidazole ring, a triazole ring, a pyrimidine ring, a uridine ring, a pyrazine ring and a pyridazine ring. Among them, Ar$^1$ is preferably a benzene ring, a pyrrole ring, a thiophene ring, a furan ring or a pyrazole ring, and more preferably a benzene ring, a thiophene ring or a pyrazole ring.

In the above Formulae (I) and (Ia), A may be substituted with the same or different 1 to 3 substituents, for example, which are each independently selected from a halogen atom; a hydroxyl group; a C$_1$-C$_6$ alkyl group, a C$_3$-C$_8$ cycloalkyl group, a C$_1$-C$_6$ alkyloxy group and a C$_1$-C$_6$ alkylthio group (these 4 groups may be substituted with 1 to 4 substituents which are each independently selected from a halogen atom or a hydroxyl group or an amino group); a methylenedioxy group; a cyano group; a C$_1$-C$_6$ alkylsulfonyl group; a C$_1$-C$_6$ alkylsulfonylamino group; a nitro group; a carboxyl group; a substituted amino group; a 5- or 6-membered heteroaryl group; and a 4- to 6-membered heterocyclyl group.

Groups defined as A include, for example, a phenyl group, a naphthyl group, an azulenyl group, a pyrrolyl group, an indolyl group, a pyridyl group, a quinolinyl group, an isoquinolinyl group, a thienyl group, a benzothienyl group, a furyl group, a benzofuranyl group, a thiazolyl group, a benzothiazolyl group, an isothiazolyl group, a benzoisothiazolyl group, a pyrazolyl group, an indazolyl group, an oxazolyl group, a benzoxazolyl group, an isoxazolyl group, a benzoisoxazolyl group, an imidazolyl group, a benzoimidazolyl group, a triazolyl group, a benzotriazolyl group, a pyrimidinyl group, a uridyl group, a pyrazinyl group, a pyridazinyl group, an imidazopyridyl group, a triazolopyridyl group and a pyrrolopyridyl group. Preferred are a phenyl group, a naphthyl group, a thienyl group, a benzothienyl group, a furyl group and a benzofuranyl group, and more preferred are a phenyl group, a thienyl group and a benzothienyl group.

As used herein, the term "C$_1$-C$_6$ alkyl group" refers to a linear or branched alkyl group containing 1 to 6 carbon atoms. Examples include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl. Preferred C$_1$-C$_6$ alkyl groups are, for example, linear or branched alkyl groups containing 1 to 3 carbon atoms, with methyl and ethyl being particularly preferred.

As used herein, the term "$C_2$-$C_6$ alkenyl group" refers to a linear or branched alkenyl group containing 2 to 6 carbon atoms. Examples include ethenyl (vinyl), 1-propenyl, 2-propenyl (allyl), propen-2-yl and 3-butenyl (homoallyl).

As used herein, the term "$C_2$-$C_6$ alkynyl group" refers to a linear or branched alkynyl group containing 2 to 6 carbon atoms. Examples include ethynyl, 1-propynyl, 2-propynyl, 1-butynyl, 2-butynyl and 3-butynyl.

As used herein, the term "$C_3$-$C_8$ cycloalkyl group" refers to a cyclic alkyl group containing 3 to 8 carbon atoms. Examples include cyclopropyl, cyclobutyl, cyclopentyl, cyclohexyl, cycloheptyl and cyclooctyl.

As used herein, the term "$C_1$-$C_6$ alkoxy group" refers to an alkyloxy group whose alkyl moiety is a linear or branched alkyl group containing 1 to 6 carbon atoms. Examples include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy and 3-ethylbutoxy.

As used herein, the term "$C_7$-$C_{14}$ aralkyl group" refers to an arylalkyl group containing 7 to 14 carbon atoms, which contains an aryl group. Examples include benzyl, 1-phenethyl, 2-phenethyl, 1-naphthylmethyl and 2-naphthylmethyl.

As used herein, the term "$C_7$-$C_{14}$ aralkyloxy group" refers to an arylalkyloxy group containing 7 to 14 carbon atoms, which contains the already-defined aralkyl group. Examples include benzyloxy, 1-phenethyloxy, 2-phenethyloxy, 1-naphthylmethyloxy and 2-naphthylmethyloxy.

As used herein, the term "aryl group" refers to an aryl group having an aromatic hydrocarbon ring containing 6 to 10 carbon atoms. Examples include phenyl, 1-naphthyl and 2-naphthyl.

As used herein, the term "heteroaryl group" refers to a 5- to 10-membered aromatic heterocyclic group containing one or more heteroatoms independently selected from an oxygen atom, a nitrogen atom and a sulfur atom. Examples include furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrimidinyl, pyrazinyl, pyridazinyl, indolyl, quinolinyl and isoquinolinyl. Preferred heteroaryl groups are 5- to 6-membered cyclic heteroaryl groups such as a furyl group, a pyrazolyl group, a thienyl group and a pyridinyl group, with a thienyl group being particularly preferred.

As used herein, the term "aryloxy group" refers to an aryloxy group whose aryl moiety is the already-defined aromatic hydrocarbon group containing 6 to 10 carbon atoms. Examples include phenoxy, 1-naphthoxy and 2-naphthoxy.

As used herein, the term "heteroaryloxy group" refers to a heteroaryloxy group whose heteroaryl moiety is the already-defined 5- to 10-membered aromatic heterocyclic group containing one or more heteroatoms selected from an oxygen atom, a nitrogen atom and a sulfur atom. Examples include furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridinyloxy, pyrimidinyloxy, pyrazinyloxy, pyridazinyloxy, indolyloxy, quinolinyloxy and isoquinolinyloxy. Preferred heteroaryloxy groups are 5- to 6-membered heteroaryloxy groups.

As used herein, the term "$C_1$-$C_6$ alkylamino group" refers to an alkylamino group whose alkyl moiety is a linear or branched alkyl group containing 1 to 6 carbon atoms. Examples include methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino and 2-ethylbutylamino.

As used herein, the term "di-($C_1$-$C_6$ alkyl)amino group" refers to a dialkylamino group whose two alkyl moieties are the same or different linear or branched alkyl groups containing 1 to 6 carbon atoms. Examples of the "di-($C_1$-$C_6$ alkyl) amino group" include dimethylamino, diethylamino, di-n-propylamino, di-i-propylamino, di-n-butylamino, methyl-n-butylamino, methyl-s-butylamino, methyl-1-butylamino, methyl-t-butylamino, ethyl-n-butylamino, ethyl-s-butylamino, ethyl-1-butylamino and ethyl-t-butylamino.

As used herein, the term "$C_1$-$C_6$ alkylthio group" refers to an alkylthio group whose alkyl moiety is a linear or branched alkyl group containing 1 to 6 carbon atoms. Examples include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio and 2-ethylbutylthio.

As used herein, the term "$C_1$-$C_6$ alkylsulfinyl group" refers to an alkylsulfinyl group (—SO—R) whose alkyl moiety is a linear or branched alkyl group containing 1 to 6 carbon atoms. Examples include methylsulfinyl, ethylsulfinyl, n-propylsulfinyl, i-propylsulfinyl, n-butylsulfinyl, s-butylsulfinyl, i-butylsulfinyl, t-butylsulfinyl, n-pentylsulfinyl, 3-methylbutylsulfinyl, 2-methylbutylsulfinyl, 1-methylbutylsulfinyl, 1-ethylpropylsulfinyl, n-hexylsulfinyl, 4-methylpentylsulfinyl, 3-methylpentylsulfinyl, 2-methylpentylsulfinyl, 1-methylpentylsulfinyl, 3-ethylbutylsulfinyl and 2-ethylbutylsulfinyl.

As used herein, the term "$C_1$-$C_6$ alkylsulfonyl group" refers to an alkylsulfonyl group whose alkyl moiety is a linear or branched alkyl group containing 1 to 6 carbon atoms. Examples include methylsulfonyl, ethylsulfonyl, n-propylsulfonyl, i-propylsulfonyl, n-butylsulfonyl, s-butylsulfonyl, i-butylsulfonyl, t-butylsulfonyl, n-pentylsulfonyl, 3-methylbutylsulfonyl, 2-methylbutylsulfonyl, 1-methylbutylsulfonyl, 1-ethylpropylsulfonyl, n-hexylsulfonyl, 4-methylpentylsulfonyl, 3-methylpentylsulfonyl, 2-methylpentylsulfonyl, 1-methylpentylsulfonyl, 3-ethylbutylsulfonyl and 2-ethylbutylsulfonyl.

As used herein, "—C(=O)—Rx" encompasses a $C_1$-$C_6$ alkylcarbonyl group, a $C_7$-$C_{14}$ aralkylcarbonyl group, a $C_1$-$C_6$ alkoxycarbonyl group, a $C_7$-$C_{14}$ aralkyloxycarbonyl group and the like. Examples of a $C_1$-$C_6$ alkylcarbonyl group include an acetyl group, a propionyl group, a butyryl group and a pivaloyl group, with an acetyl group being particularly preferred. Examples of a $C_7$-$C_{14}$ aralkylcarbonyl group include a benzylcarbonyl group and a naphthylmethylcarbonyl group, with a benzylcarbonyl group being preferred.

Examples of a $C_1$-$C_6$ alkoxycarbonyl group include a methoxycarbonyl group and an ethoxycarbonyl group, with a methoxycarbonyl group being preferred. Examples of a $C_7$-$C_{14}$ aralkyloxycarbonyl group include a benzyloxycarbonyl group and a naphthylmethyloxycarbonyl group, with a benzyloxycarbonyl group being preferred.

As used herein, the term "halogen atom" encompasses a fluorine atom, a chlorine atom, a bromine atom, an iodine atom and the like.

As used herein, the term "4- to 7-membered heterocyclic ring" refers to a heterocyclic ring which may be completely saturated or partially or completely unsaturated and which contains one nitrogen atom and may further contain one or more heteroatoms independently selected from an oxygen atom, a nitrogen atom and a sulfur atom. Examples include azetidine, pyrrolidine, piperidine and morpholine, with piperidine being particularly preferred.

As used herein, the term "aromatic carbocyclic ring" refers to a 6- to 10-membered aromatic carbocyclic ring. Examples include a benzene ring and a naphthalene ring.

As used herein, the term "aromatic heterocyclic ring" refers to a 5- to 6-membered aromatic heterocyclic ring containing one or more heteroatoms independently selected from an oxygen atom, a nitrogen atom and a sulfur atom. Examples include a pyrrole ring, an indole ring, a thiophene ring, a benzothiophene ring, a furan ring, a benzofuran ring, a pyridine ring, a quinoline ring, an isoquinoline ring, a thiazole ring, a benzothiazole ring, an isothiazole ring, a benzoisothiazole ring, a pyrazole ring, an indazole ring, an oxazole ring, a benzoxazole ring, an isoxazole ring, a benzoisoxazole ring, an imidazole ring, a benzoimidazole ring, a triazole ring, a benzotriazole ring, a pyrimidine ring, a uridine ring, a pyrazine ring and a pyridazine ring.

As used herein, the term "substituted amino group" encompasses —NReRf, wherein Re represents a hydrogen atom, a $C_1$-$C_6$ alkyl group, a $C_1$-$C_6$ alkylcarbonyl group, carbamoyl or a $C_1$-$C_6$ alkoxycarbonyl group; and Rf represents a hydrogen atom or a $C_1$-$C_6$ alkyl group, or Re and Rf may form a 4- to 7-membered heterocyclic ring together with the nitrogen atom to which they are attached, and the like.

As used herein, the term "$C_1$-$C_3$ alkylenedioxy group" refers to a divalent group represented by the formula —O—($C_1$-$C_3$ alkylene)-O—. Examples include a methylenedioxy group, an ethylenedioxy group and a dimethylmethylenedioxy group.

As used herein, the term "heterocyclyl group" refers to a 4- to 7-membered heterocyclic group which may be completely saturated or partially or completely unsaturated and which contains one or more heteroatoms independently selected from an oxygen atom, a nitrogen atom and a sulfur atom. Examples include azetidinyl, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, pyridinyl, pyrazinyl, pyrimidinyl, pyridazinyl, hexamethyleneimino, furyl, tetrahydrofuryl, thienyl, tetrahydrothienyl, dioxolanyl, oxathiolanyl and dioxanyl. Such a heterocyclic group may be substituted at any substitutable position on its carbon or nitrogen atom(s).

As used herein, the term "heterocyclyloxy group" refers to an oxy group attached to a 4- to 7-membered heterocyclic ring which may be completely saturated or partially or completely unsaturated and which contains one or more heteroatoms independently selected from an oxygen atom, a nitrogen atom and a sulfur atom. Examples include azetidinyloxy, pyrrolidinyloxy, piperidinyloxy, piperazinyloxy, pyrrolyloxy, imidazolyloxy, imidazolinyloxy, pyrazolyloxy, pyrazolinyloxy, oxazolinyloxy, morpholinyloxy, thiomorpholinyloxy, pyridinyloxy, pyrazinyloxy, pyrimidinyloxy, pyridazinyloxy, hexamethyleneiminoxy, furyloxy, tetrahydrofuryloxy, thienyloxy, tetrahydrothienyloxy, dioxolanyloxy, oxathiolanyloxy and dioxanyloxy. Such a heterocyclic group may be substituted at any substitutable position on its carbon or nitrogen atom(s).

The compound of the present invention also includes mixtures or isolated forms of various stereoisomers such as tautomers and optical isomers.

In some cases, the compound of the present invention may form an acid addition salt. Depending on the type of substituent, the compound of the present invention may also form a salt with a base. Specific examples of such a salt include acid addition salts with mineral acids (e.g., hydrochloric acid, hydrobromic acid, hydroiodic acid, sulfuric acid, nitric acid, phosphoric acid), with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid) and with acidic amino acids (e.g., aspartic acid, glutamic acid). Likewise, examples of a salt formed with a base include salts with inorganic bases (e.g., sodium, potassium, magnesium, calcium, aluminum), salts with organic bases (e.g., methylamine, ethylamine, ethanolamine), salts with basic amino acids (e.g., lysine, ornithine), as well as ammonium salts.

Moreover, the compound of the present invention also includes hydrates, various pharmaceutically acceptable solvates and polymorphic crystalline forms, etc.

It should be noted that the compound of the present invention is not limited to the compounds shown in the Example section described later, and it encompasses all spiroketal derivatives of the above Formula (I) and their pharmaceutically acceptable salts.

Moreover, the present invention also encompasses so-called prodrugs, i.e., compounds that are metabolized in vivo into compounds of the above Formula (I) or their pharmaceutically acceptable salts. Examples of prodrug-forming groups for the compound of the present invention include those found in Prog. Med. vol. 5, pp. 2157-2161 (1985) and "Iyakuhin no Kaihatsu (Development of Pharmaceuticals)" vol. 7 (Molecular Design), pp. 163-198, published in 1990 by Hirokawa Publishing Co., Japan.

The compound of the present invention can be prepared by applying various known synthesis methods, depending on its characteristics based on the skeletal structure or the type of substituent. In some cases, depending on the type of functional group, it is technically preferable to protect this functional group with a suitable protecting group at the stage of starting material or at an intermediate stage. In this case, the protecting group can be removed in the subsequent step to obtain a desired compound. For example, a hydroxyl group or a carboxyl group can be given as a functional group required to be protected during the production process. Protecting groups for these groups include those found in "Protective Groups in Organic Synthesis" 2nd edition, written by Greene and Wuts. The type of protecting group to be used, as well as reaction conditions for introduction and removal of the protecting group may be selected as appropriate based on known techniques such as shown in the above document.

The compound of the present invention has inhibitory activity against sodium-dependent glucose cotransporter 2 (SGLT2) involved in glucose reabsorption in the kidney (J. Clin. Invest., vol. 93, p. 397, 1994). Inhibition of SGLT2 prevents sugar reabsorption and removes excess sugar from the body to thereby produce a therapeutic effect on diabetes and an improving effect on insulin resistance through correction of hyperglycemia without applying any load to pancreatic β cells.

Thus, according to one aspect of the present invention, there is provided a pharmaceutical preparation for preventing or treating diseases or conditions which can be ameliorated by inhibition of SGLT2 activity, e.g., diabetes, diabetes-related diseases and diabetic complications.

As used herein, the term "diabetes" encompasses type I diabetes, type II diabetes, and other types of diabetes with specific etiology. Likewise, the term "diabetes-related diseases" includes, for example, obesity, hyperinsulinemia, abnormal carbohydrate metabolism, hyperlipidemia, hypercholesterolemia, hypertriglyceridemia, abnormal lipid metabolism, hypertension, congestive heart failure, edema, hyperuricemia and gout.

As used herein, the term "diabetic complications" include both acute complications and chronic complications. Examples of "acute complications" include hyperglycemia (e.g., ketoacidosis), infections (e.g., skin, soft tissue, biliary system, respiratory system and urinary tract infections), etc. Examples of "chronic complications" include microangiopathy (e.g., nephropathy, retinopathy), arteriosclerosis (e.g., atherosclerosis, heart infarction, brain infarction, lower extremity arterial occlusion), neuropathy (e.g., sensory nerves, motor nerves, autonomic nerves), foot gangrene, etc. Major diabetic complications include diabetic retinopathy, diabetic nephropathy and diabetic neuropathy.

The compound of the present invention may also be used in combination with any therapeutic agent for diabetes, diabetic complications, hyperlipidemia or hypertension, which depends on a different mechanism of action other than inhibition of SGLT2 activity. When combined with other drugs, the compound of the present invention can be expected to produce an additive effect on these diseases, which is greater than either one alone.

Examples of a "therapeutic agent for diabetes or diabetic complications" available for combination use include, for example, insulin sensitizers (e.g., PPARδ agonists, PPARα/γ agonists, PPARδ agonists, PPARα/γ/δ agonists), glycosidase inhibitors, biguanides, insulin secretagogues, insulin formulations, glucagon receptor antagonists, insulin receptor kinase stimulators, tripeptidyl peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose-bisphosphatase inhibitors, pyruvate dehydrogenase inhibitors, glucokinase activators, D-chiroinositol, glycogen synthase kinase-3 inhibitors, glucagon-like peptide-1, glucagon-like peptide-1 analogs, glucagon-like peptide-1 agonists, amylin, amylin analogs, amylin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKKβ inhibitors, lipid peroxidase inhibitors, N-acetylated-α-linked-acid-dipeptidase inhibitors, insulin-like growth factor-I, platelet-derived growth factors (PDGF), platelet-derived growth factor (PDGF) analogs, epidermal growth factors (EGF), nerve growth factors, carnitine derivatives, uridine, 5-hydroxy-1-methylhydantoin, EGB-761, bimoclomol, sulodexide, Y-128 and TAR-428.

Illustrative examples of a therapeutic agent for diabetes or diabetic complications are as follows.

"Biguanides" include metformin hydrochloride and phenformin.

"Insulin secretagogues" include those of the sulfonylurea type such as glyburide (glibenclamide), glypizide, gliclazide and chlorpropamide, as well as those of the non-sulfonylurea type such as nateglinide, repaglinide and mitiglinide.

"Insulin formulations" encompass both recombinantly produced human insulin and animal-derived insulin. Such formulations can be divided into three groups depending on the length of their duration: fast-acting formulations (e.g., human insulin, human neutral insulin); intermediate-acting formulations (e.g., insulin-human isophane insulin aqueous suspension, human neutral insulin-human isophane insulin aqueous suspension, human insulin zinc aqueous suspension, insulin zinc aqueous suspension); and long-acting formulations (e.g., human crystalline insulin zinc suspension).

"Glycosidase inhibitors" include acarbose, voglibose and miglitol.

"Insulin sensitizers" include PPARγ agonists such as troglitazone, pioglitazone and rosiglitazone, PPARα/γ dual agonists such as MK-767 (KRP-297), tesaglitazar, LM4156, LY510929, DRF-4823 and TY-51501, as well as PPARδ agonists such as GW-501516.

"Tripeptidyl peptidase II inhibitors" include UCL-139.

"Dipeptidyl peptidase IV inhibitors" include NVP-DPP728A, LAF-237, MK-0431, P32/98 and TSL-225.

"Aldose reductase inhibitors" include ascorbyl gamolenate, tolrestat, epalrestat, fidarestat, sorbinil, ponalrestat, risarestat and zenarestat.

"γ-Aminobutyric acid receptor antagonists" include topiramate.

"Sodium channel antagonists" include mexiletine hydrochloride.

"Transcription factor NF-κB inhibitors" include dexlipotam.

"Lipid peroxidase inhibitors" include tirilazad mesylate.

"N-Acetylated-α-linked-acid-dipeptidase inhibitors" include GPI-5693.

"Carnitine derivatives" include carnitine and levacecamine hydrochloride.

Examples of a "therapeutic agent for hyperlipidemia or hypertension" available for combination use include, for example, hydroxymethylglutaryl coenzyme A reductase inhibitors, fibrate compounds, β₃-adrenergic receptor agonists, AMPK activators, acyl-coenzyme A:cholesterol acyltransferase inhibitors, probucol, thyroid hormone receptor agonists, cholesterol absorption inhibitors, lipase inhibitors, microsomal triglyceride transfer protein inhibitors, lipoxygenase inhibitors, carnitine palmitoyl transferase inhibitors, squalene synthase inhibitors, low-density lipoprotein receptor promoters, nicotinic acid derivatives, bile acid binding resins, sodium-dependent bile acid transporter inhibitors, cholesterol ester transport protein inhibitors, angiotensin-converting enzyme inhibitors, angiotensin II receptor antagonists, endothelin-converting enzyme inhibitors, endothelin receptor antagonists, diuretics, calcium antagonists, vasodilator antihypertensives, sympatholytic agents, central-acting antihypertensives, α₂-adrenergic receptor agonists, antiplatelet agents, uric acid production inhibitors, uric acid excretion stimulators, urine alkalizers, anorectics, ACE inhibitors, adiponectin receptor agonists, GPR40 agonists and GPR40 antagonists.

Illustrative examples of a therapeutic agent for hyperlipidemia or hypertension are as follows.

"Hydroxymethylglutaryl coenzyme A reductase inhibitors" include fluvastatin, lovastatin, pravastatin, cerivastatin and pitavastatin.

"Fibrate compounds" include bezafibrate, beclobrate and binifibrate.

"Squalene synthase inhibitors" include TAK-475 and α-phosphonosulfonate derivatives (U.S. Pat. No. 5,712,396).

"Acyl-coenzyme A:cholesterol acyltransferase inhibitors" include CI-1011, NTE-122, FCE-27677, RP-73163, MCC-147 and DPU-129.

"Low-density lipoprotein receptor promoters" include MD-700 and LY-295427.

"Microsomal triglyceride transfer protein inhibitors (MTP inhibitors)" include compounds as described in, e.g., U.S. Pat. Nos. 5,739,135, 5,712,279 and 5,760,246.

"Anorectics" include adrenaline/noradrenaline agonists (e.g., mazindol, ephedrine), serotonin agonists (selective serotonin reuptake inhibitors such as fluvoxamine), adrenaline/serotonin agonists (e.g., sibutramine), melanocortin 4 receptor (MC4R) agonists, α-melanocyte-concentrating hormones (α-MCH), leptin, as well as cocaine- and amphetamine-regulated transcripts (CART).

"Thyroid hormone receptor agonists" include liothyronine sodium and levothyroxine sodium.

"Cholesterol absorption inhibitors" include ezetimibe.

"Lipase inhibitors" include orlistat.

"Carnitine palmitoyl transferase inhibitors" include etomoxir.

"Nicotinic acid derivatives" include nicotinic acid, nicotinamide, nicomol and nicorandil.

"Bile acid binding resins" include cholestyramine, colestilan and colesevelam hydrochloride.

"Angiotensin-converting enzyme inhibitors" include captoril, enalapril maleate, alacepril and cilazapril.

"Angiotensin II receptor antagonists" include candesartan cilexetil, losartan potassium and eprosartan mesylate.

"Endothelin-converting enzyme inhibitors" include CGS-31447 and CGS-35066.

"Endothelin receptor antagonists" include L-749805, TBC-3214 and BMS-182874.

By way of example, in treating diabetes or the like, it would be preferable to use the compound of the present invention in combination with at least one drug selected from the group consisting of an insulin sensitizer (e.g., a PPARγ agonist, a PPARα/γ agonist, a PPARδ agonist, a PPARα/γ/δ agonist), a glycosidase inhibitor, a biguanide, an insulin secretagogue, an insulin formulation and a dipeptidyl peptidase IV inhibitor.

Alternatively, it would be preferable to use the compound of the present invention in combination with at least one drug selected from the group consisting of a hydroxymethylglutaryl coenzyme A reductase inhibitor, a fibrate compound, a squalene synthase inhibitor, an acyl-coenzyme A:cholesterol acyltransferase inhibitor, a low-density lipoprotein receptor promoter, a microsomal triglyceride transfer protein inhibitor and an anorectic.

The pharmaceutical preparation of the present invention can be administered systemically or topically via oral route or parenteral (e.g., intrarectal, subcutaneous, intramuscular, intravenous, percutaneous) route.

For use as a pharmaceutical preparation, the compound of the present invention may be formulated into any desired dosage form selected from solid compositions, liquid compositions and other compositions, as appropriate for the intended purpose. The pharmaceutical preparation of the present invention can be prepared by blending the compound of the present invention with pharmaceutically acceptable carrier(s). More specifically, the compound of the present invention may be supplemented with commonly used excipients, extenders, binders, disintegrating agents, coating agents, sugar-coating agents, pH adjusters, solubilizers, aqueous or non-aqueous solvents and so on, and then formulated using standard techniques into tablets, pills, capsules, granules, powders, solutions, emulsions, suspensions, injections, etc. Examples of excipients and extenders include, for example, lactose, magnesium stearate, starch, talc, gelatin, agar, pectin, gum arabic, olive oil, sesame oil, cacao butter, ethylene glycol and other commonly used materials.

Also, the compound of the present invention may be modified to form an inclusion compound with, e.g., α-, β- or γ-cyclodextrin or methylated cyclodextrin before being formulated.

The dose of the compound of present invention will vary depending on the disease or symptom to be treated, body weight, age, sex, the route of administration, etc. The adult dose is preferably 0.1 to 1000 mg/kg body weight/day, more preferably 0.1 to 200 mg/kg body weight/day, given as a single dose or in divided doses.

The compound of the present invention can be synthesized, for example, as shown in the production schemes below.

The compound of the present invention can be synthesized as shown in Scheme 1:

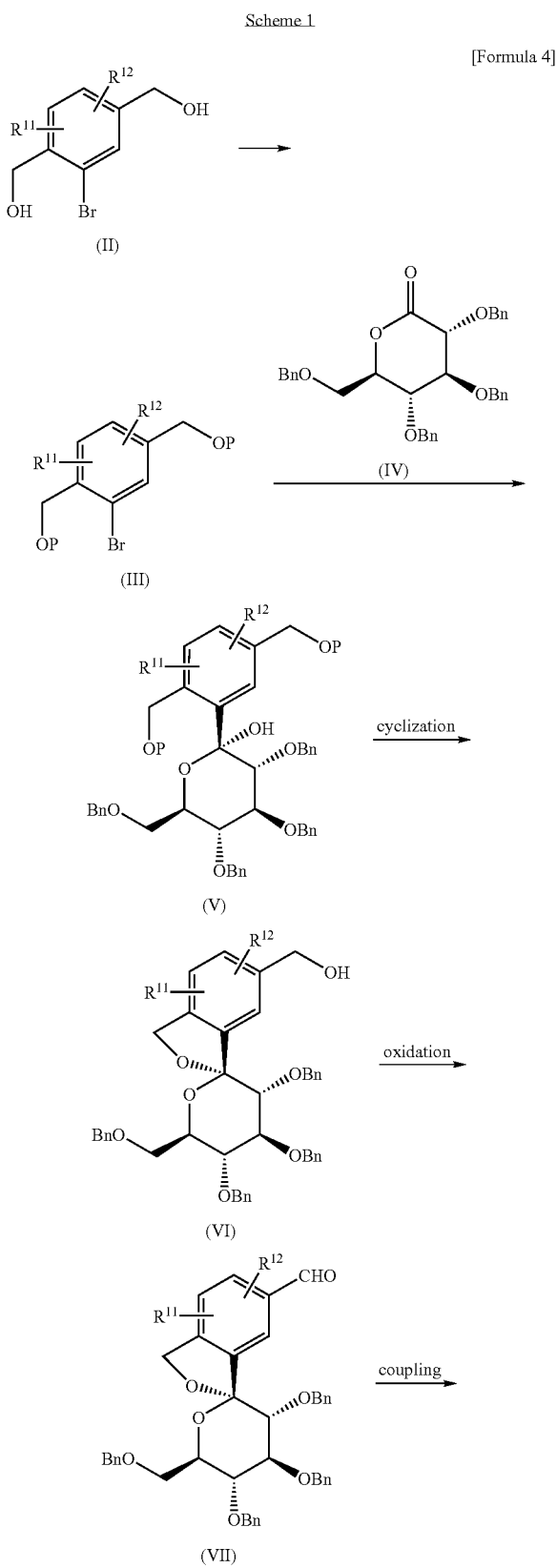

-continued

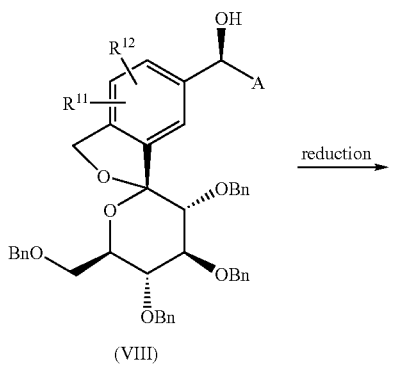

(VIII)

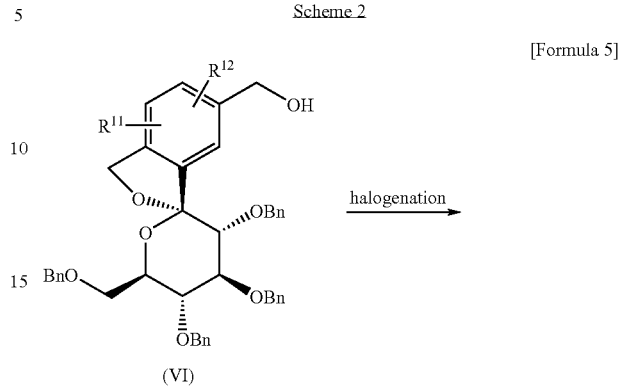

wherein R¹¹ and R¹² have the same meaning as defined above for substituents on Ar¹, A is as defined above, and P represents a protecting group for a hydroxyl group.

More specifically, after Compound (II) is protected with a protecting group P (e.g., a trityl group, a tert-butyldimethylsilyl group or a tetrahydropyranyl group, preferably a group removable by the action of an acid), the resulting Compound (III) is treated with an alkyllithium (e.g., n-butyllithium, sec-butyllithium) and reacted with Compound (IV) to obtain Compound (V). In the presence or absence of a silane reagent (e.g., triethylsilane), Compound (V) is then treated with an acid (e.g., trifluoroacetic acid or boron trifluoride-diethyl ether complex) and converted into Compound (VI), followed by treatment with an oxidizing agent (e.g., Dess-Martin reagent, TPAP-NMO, DMSO-acetic anhydride) to obtain Compound (VII). This compound is converted into Compound (VIII) by treatment with a metal reagent such as a Grignard reagent, followed by debenzylation, e.g., through catalytic hydrogenation in the presence of a palladium catalyst or a technique using a Lewis acid (boron tribromide, boron trichloride, boron trichloride-dimethylsulfide complex, boron trifluoride-diethyl ether complex plus ethanethiol, boron trifluoride-diethyl ether complex plus dimethylsulfide) to prepare the compound of the present invention. It should be noted that Compounds (II) and (IV) can be synthesized as described, for example, in J. Org. Chem., vol. 29, p. 2034, 1964 and Carbohydr. Res., vol. 260, p. 243, 1994, respectively.

The compound of the present invention can also be prepared as shown in the following Scheme 2:

Scheme 2

[Formula 5]

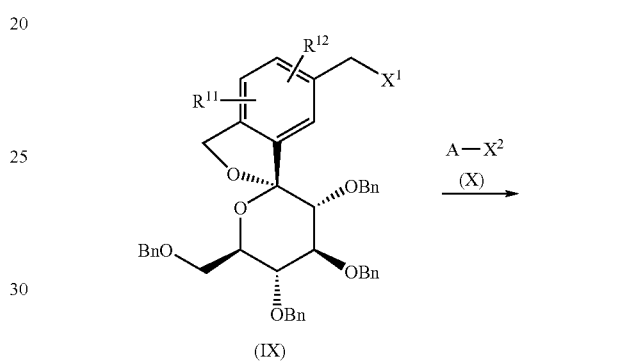

(VI)

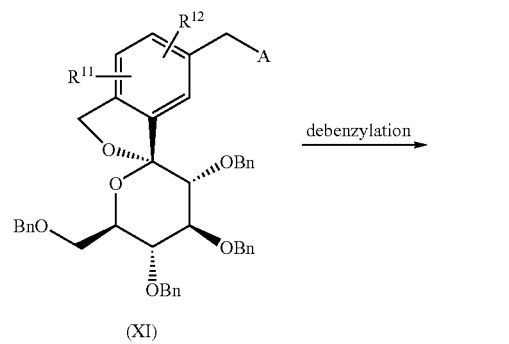

(IX)

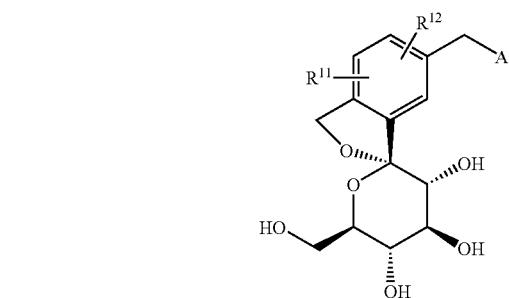

(XI)

wherein R¹¹ and R¹² have the same meaning as defined above for substituents on Ar¹, A is as defined above, X¹ represents a halogen atom, and X² represents a halogen atom or B(OR¹³), wherein R¹³ represents hydrogen or lower alkyl.

More specifically, Compound (VI) is treated with an appropriate halogenating agent (e.g., N-bromosuccimide, carbon tetrabromide). The resulting Compound (IX) is then reacted with Compound (X) in the presence of an appropriate palladium catalyst to obtain Compound (XI), followed by debenzylation, e.g., through catalytic hydrogenation in the presence of a palladium catalyst or a technique using a Lewis acid (boron tribromide, boron trichloride, boron trichloride-dimethylsulfide complex, boron trifluoride-diethyl ether complex plus ethanethiol, boron trifluoride-diethyl ether complex plus dimethylsulfide) to prepare the compound of the present invention.

The compound of the present invention can also be prepared as shown in Scheme 3.

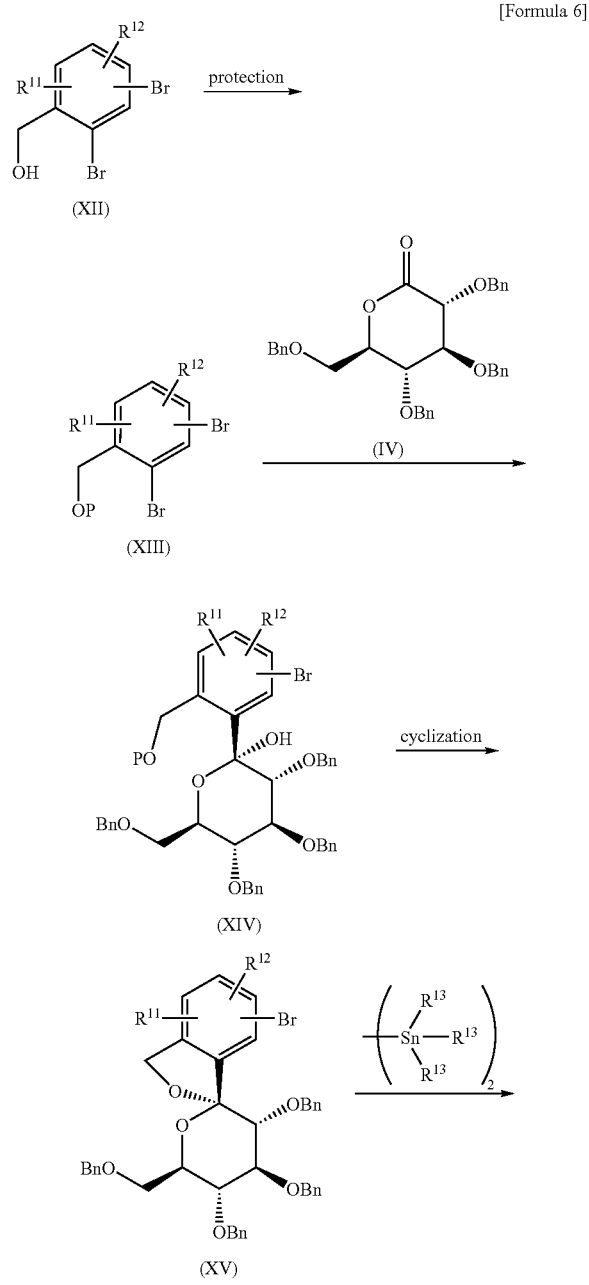

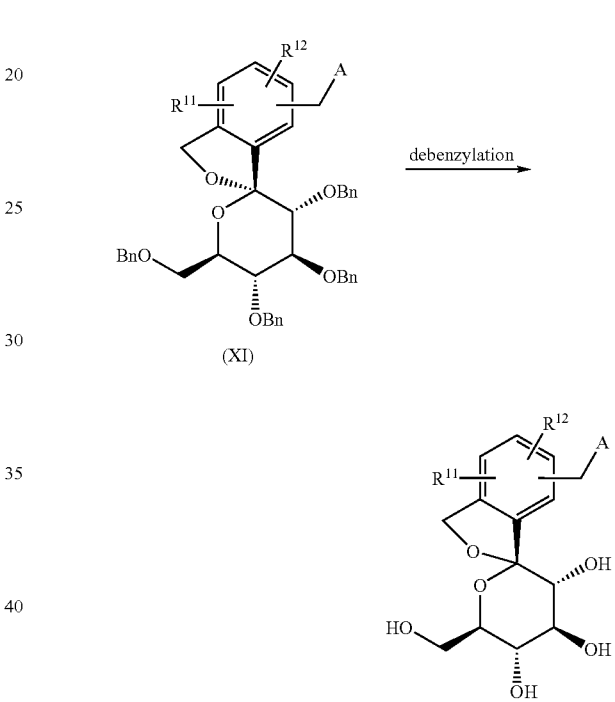

wherein $R^{11}$ and $R^{12}$ have the same meaning as defined above for substituents on $Ar^1$, $R^{13}$ represents lower alkyl, A is as defined above, P represents a protecting group for a hydroxyl group, and $X^1$ represents a halogen atom.

More specifically, after the hydroxyl group of Compound (XII) is protected with an appropriate protecting group P (e.g., a trityl group, a tert-butyldimethylsilyl group, a tetrahydropyranyl group), the resulting Compound (XIII) is treated with an appropriate alkyllithium (e.g., n-butyllithium, sec-butyllithium) and reacted with Compound (IV) to derive Compound (XIV). In the presence or absence of a silane reagent (e.g., triethylsilane), Compound (XIV) is then treated with an acid (e.g., trifluoroacetic acid or boron trifluoride-diethyl ether complex) to derive Compound (XV), followed by treatment with a hexaalkylditin in the presence of an appropriate palladium catalyst to obtain Compound (XVI). In the presence of an appropriate palladium catalyst, Compound (XVI) is then treated with Compound (XVII) to derive Compound (XI), followed by deprotection to synthesize the compound of the present invention.

The compound of the present invention can also be prepared as shown in the following Scheme 4:

Scheme 4

[Formula 7]

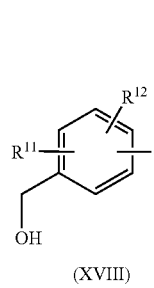 → 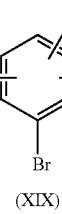

(XVIII)    (XIX)

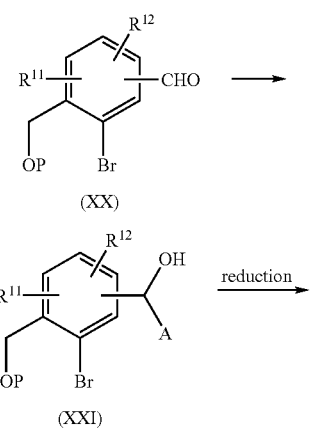

(XX), (XXI), (XXII), (XXIII)

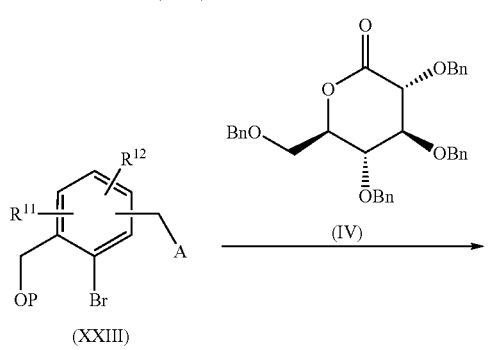

(XXIV)

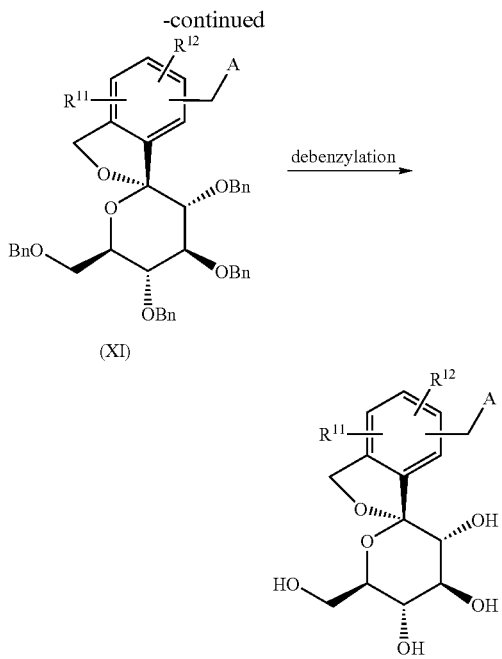

(XI)

-continued wherein $R^{11}$ and $R^{12}$ have the same meaning as defined above for substituents on $Ar^1$, A is as defined above, P represents a protecting group for a hydroxyl group, and X represents a halogen atom.

Compound (XVIII) is brominated with an appropriate brominating agent (e.g., bromine, N-bromosuccimide) and its hydroxyl group is protected with an appropriate protecting group P (e.g., a trityl group, a tert-butyldimethylsilyl group, a tetrahydropyranyl group), followed by using a Grignard reagent or the like to obtain Adduct (XXI). The resulting hydroxyl group is removed by being treated with a silane reagent (e.g., triethylsilane) in the presence of an acid (e.g., trifluoroacetic acid or boron trifluoride-diethyl ether complex) to derive Compound (XXII). If necessary, the hydroxyl group is protected again to give Compound (XXIII). The reaction between Compounds (IV) and (XXIII) is performed in the same manner as shown in Scheme 3 for the reaction between Compounds (IV) and (XIII). The conversion of Compound (XXIV) into Compound (XI) is performed in the same manner as shown in Scheme 3 for the conversion of Compound (XIV) into Compound (XV).

The compound of the present invention can also be prepared as shown in the following Scheme 5:

Scheme 5

[Formula 8]

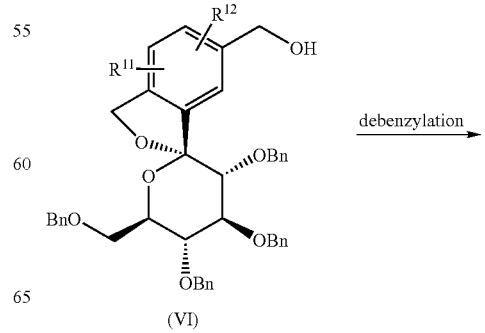

(VI)

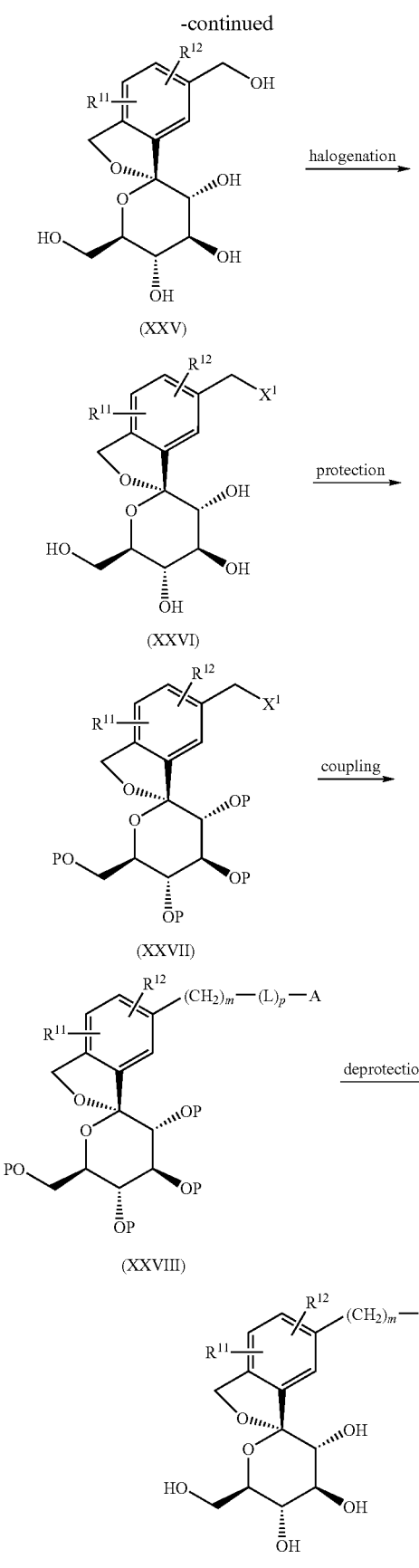

wherein $R^{11}$ and $R^{12}$ have the same meaning as defined above for substituents on $Ar^1$, L, m, p and A are as defined above, and $X^1$ represents a halogen atom.

Compound (VI) is debenzylated, e.g., through catalytic hydrogenation in the presence of a palladium catalyst or a technique using a Lewis acid (boron tribromide, boron trichloride, boron trichloride-dimethylsulfide complex, boron trifluoride-diethyl ether complex plus ethanethiol, boron trifluoride-diethyl ether complex plus dimethylsulfide), and the resulting Compound (XXV) is treated in an appropriate solvent (e.g., dimethyl sulfoxide, dimethylformamide) with a halogenating agent (e.g., trimethylsilyl chloride, trimethylsilyl bromide) to obtain Compound (XXVI). After each hydroxyl group is further protected with an appropriate protecting group (e.g., an acetyl group, a tert-butyldimethylsilyl group), the resulting Compound (XXVII) is reacted with boronic acid (e.g., phenylboronic acid) in the presence of an appropriate palladium catalyst (e.g., palladium acetate, DPPF), or alternatively, reacted with a Grignard reagent in the presence or absence of copper chloride, or alternatively, reacted with a nucleophilic reagent (e.g., phenol, aniline, thiophenol) in the presence of a base (e.g., potassium carbonate) to obtain Compound (XXVIII). This compound may be deprotected to prepare the compound of the present invention.

The compound of the present invention can also be prepared as shown in the following Scheme 6:

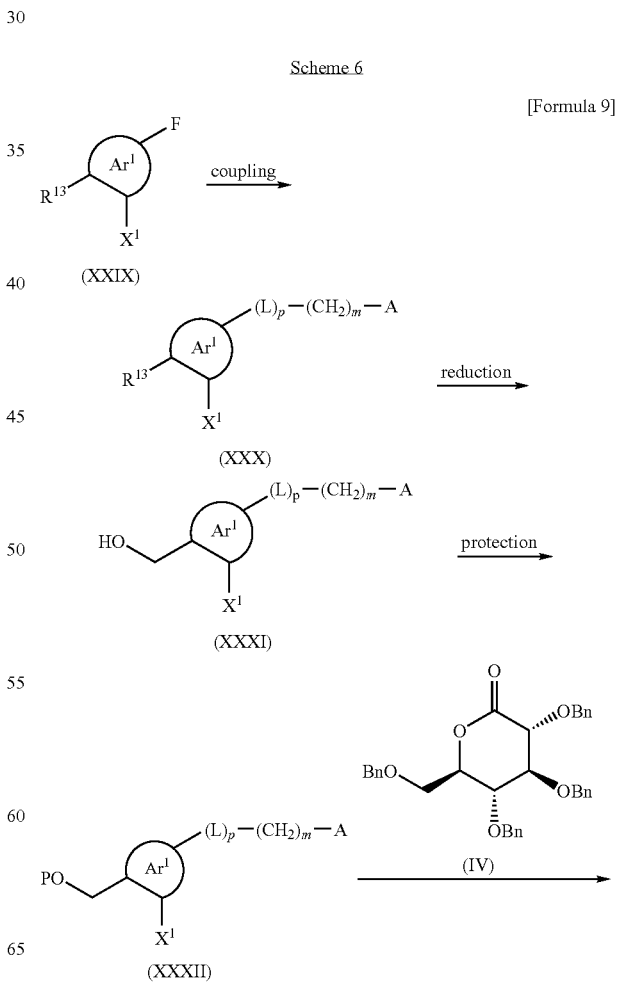

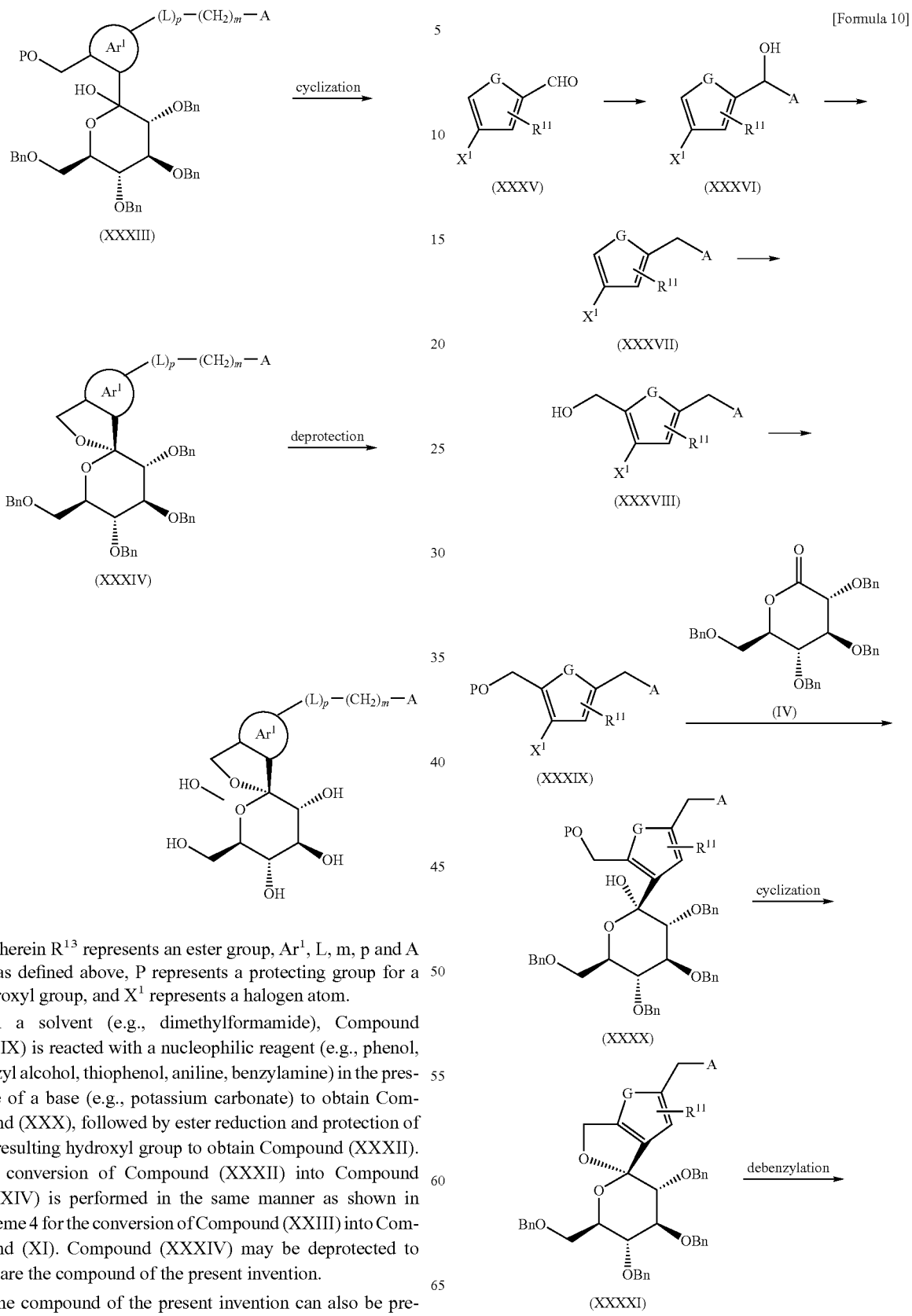

wherein $R^{13}$ represents an ester group, $Ar^1$, L, m, p and A are as defined above, P represents a protecting group for a hydroxyl group, and $X^1$ represents a halogen atom.

In a solvent (e.g., dimethylformamide), Compound (XXIX) is reacted with a nucleophilic reagent (e.g., phenol, benzyl alcohol, thiophenol, aniline, benzylamine) in the presence of a base (e.g., potassium carbonate) to obtain Compound (XXX), followed by ester reduction and protection of the resulting hydroxyl group to obtain Compound (XXXII). The conversion of Compound (XXXII) into Compound (XXXIV) is performed in the same manner as shown in Scheme 4 for the conversion of Compound (XXIII) into Compound (XI). Compound (XXXIV) may be deprotected to prepare the compound of the present invention.

The compound of the present invention can also be prepared as shown in the following Scheme 7:

-continued

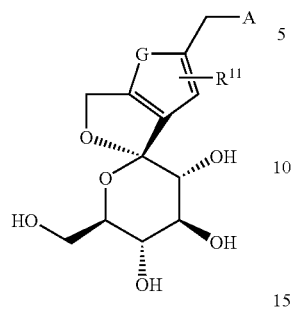

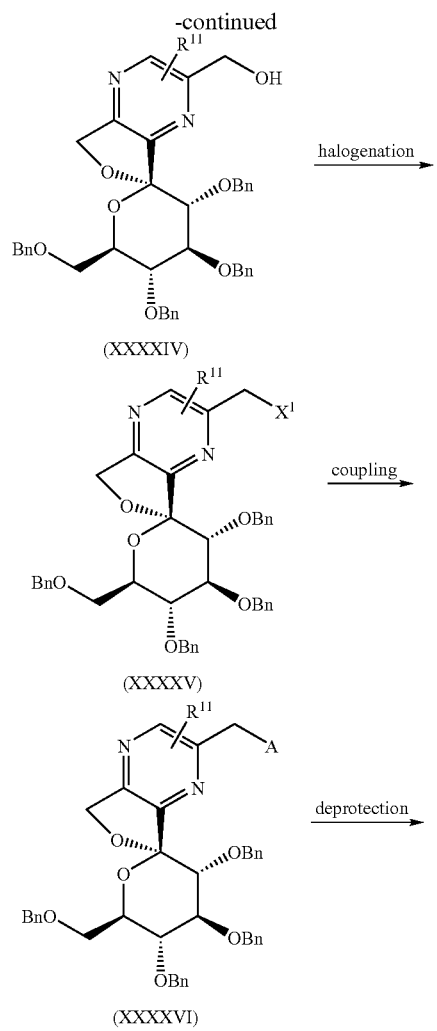

wherein R[11] has the same meaning as defined above for substituents on Ar[1], G represents —O—, —S— or —NP—, P represents a protecting group for an amino group, A is as defined above, and X[1] represents a halogen atom.

Compound (XXXV) is treated with a Grignard reagent or the like to give Compound (XXXVI), followed by using a reducing agent such as triethylsilane to obtain Compound (XXXVII). This compound is treated with a base such as LDA and then treated with oxirane to obtain Compound (XXXVIII), followed by protection of the hydroxyl group to obtain Compound (XXXIX). The conversion of Compound (XXXIX) into Compound (XXXX) is performed in the same manner as shown in Scheme 4 for the conversion of Compound (XXIII) into Compound (XI). Compound (XXXXI) may be deprotected to prepare the compound of the present invention.

The compound of the present invention can also be prepared as shown in the following Scheme 8:

Scheme 8

[Formula 11]

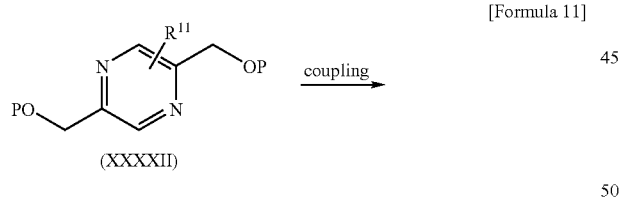

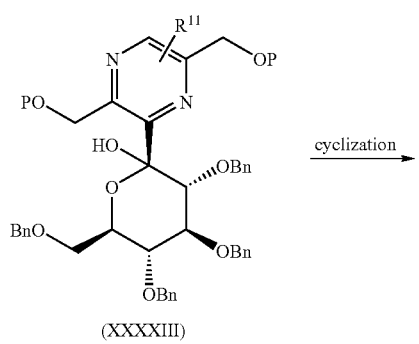

wherein R[11] has the same meaning as defined above for substituents on Ar[1], A is as defined above, X[1] represents a halogen atom, and P represents a protective group for a hydroxyl group.

Compound (XXXXIII), which is prepared by a coupling reaction using Compound (XXXXII), is cyclized and deprotected in the presence of an acid such as p-toluenesulfonic acid to give Compound (XXXXIV). The resulting compound is treated with a halogenating agent (for example trimethylsilyl chloride, trimethylsilyl bromide and the like) in an appropriate solvent (for example dimethylsulfoxide, dimethylformamide and the like) to give Compound (XXXXV). Thereafter, the resulting compound is reacted with boronic acid (for example, phenylboronic acid and the like) in the presence of a palladium catalyst (for example palladium acetate, DPPF and the like) to give Compound (XXXXVI). By deprotection of the resulting compound, the compound of the present invention may be produced.

How to prepare the compound of the present invention is not limited to the embodiments illustrated above. For example, the compound of the present invention can also be synthesized through any combination of the steps included in Schemes 1 to 8.

EXAMPLES

The present invention will be further described in more detail by way of the following examples and test examples, which are not intended to limit the scope of the invention.

In the following examples, individual symbols are as defined below:

NMR: nuclear magnetic resonance spectrum (TMS internal standard), MS: mass spectrometry, and HPLC: high performance liquid chromatography.

NMR, MS and HPLC were measured using the following instruments.

NMR: JEOL JNM-EX-270 (270 MHz) or Brucker ARX300 (300 MHz) or Varian Mercury 300 (300 MHz) or JEOL JNM-ECP400 (400 MHz)

MS: Thermo Finigan LCQ or Waters micromass ZQ or Q-micro Triple Quadrupole Mass Spectrometer HPLC: Waters 2690/2996 (detector)

Example 1

1,1-Anhydro-1-C-[5-(4-ethylphenyl)methyl-2-(hydroxymethyl)phenyl]-β-D-glucopyranose 1) Synthesis of (2-bromo-4-hydroxymethylphenyl)methanol Under a nitrogen stream, to a solution of 2-bromo-terephthalic acid (5.0 g, 20.4 mmol) in THF (50 ml), a THF solution of $BH_3$ (1.09 M, 74.9 ml) was added dropwise at 0° C. and the mixture was stirred at room temperature for 4 hours. After addition of THF-water (1:1) to this solution, the reaction mixture was extracted with ethyl acetate. The organic layer was dried over anhydrous magnesium sulfate and then evaporated under reduced pressure to remove the solvent. The resulting residue was purified by silica gel column chromatography (developing solution=ethyl acetate:n-hexane (1:2)) to give the titled compound (4.1 g, 92%).

$^1$H-NMR (DMSO-$d_6$) δ: 4.48 (4H, t, J=5.1 Hz), 5.27 (1H, t, J=6 Hz), 5.37 (1H, t, J=5.7 Hz), 7.31 (1H, d, J=7.8 Hz), 7.45-7.49 (2H, m)

MS (ESI$^+$): 240 [M+Na]$^+$

2) Synthesis of 2-bromo-1,4-bis(trityloxymethyl)benzene

Under a nitrogen stream, to a solution of trityl chloride (11.58 g, 41.6 mmol) and (2-bromo-4-hydroxymethylphenyl)methanol (4.1 g, 18.9 mmol) in DMF (12 ml), triethylamine (5.8 ml, 41.6 mmol) and DMAP (369.2 mg, 3.02 mmol) were added and the mixture was stirred for 18 hours at room temperature. The reaction mixture was evaporated under reduced pressure to remove the solvent and then extracted with methylene chloride. The organic layer was washed with water and saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:2)) to give the titled compound (2.4 g, 18%).

$^1$H-NMR (CDCl$_3$) δ: 4.20 (4H, d, J=18 Hz), 7.22-7.34 (21H, m), 7.47-7.53 (12H, m)

3) Synthesis of 3,4,5-tris-benzyloxy-6-benzyloxymethyl-2-(2,5-bis(trityloxymethyl)phenyl)tetrahydropyran-2-ol Under a nitrogen stream, to a solution of 2-bromo-1,4-bis(trityloxymethyl)benzene (255.3 mg, 0.36 mmol) in toluene (1.5 ml), a cyclohexane solution of sec-butyllithium (0.99 M, 367 μl, 0.36 mmol) was added dropwise at room temperature and the solution was stirred for 30 minutes. This solution was added dropwise at −78° C. to a solution of 3,4,5-trisbenzyloxy-6-(benzyloxymethyl)tetrahydropyran-2-one (140 mg, 0.26 mmol) in toluene (1.5 ml) and the mixture was stirred at the same temperature for 30 minutes. After addition of water, the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:5)) to give the titled compound (242 mg, 80%).

$^1$H-NMR (CDCl$_3$) δ: 3.34 (1H, t, J=9.3 Hz), 3.46-3.51 (3H, m), 3.78 (1H, d, J=10.8 Hz), 3.92 (1H, t, J=9.3 Hz), 4.00-4.05 (1H, m), 4.08-4.16 (3H, m), 4.31 (2H, s), 4.41 (1H, d, J=12.3 Hz), 4.49-4.58 (2H, m), 4.77-4.84 (3H, m), 6.75 (2H, d, J=7.2 Hz), 6.95 (2H, t, J=7.2 Hz), 7.02-7.07 (1H, m), 7.11-7.32 (35H, m), 7.47-7.59 (12H, m), 7.69 (1H, d, J=7.5 Hz)

MS (ESI$^+$): 1184 [M+Na]$^+$

4) Synthesis of 1,1-anhydro-1-C-[2,5-bis(hydroxymethyl)phenyl]-2,3,4,6-tetra-O-benzyl-β-D-glucopyranose Under a nitrogen stream, to a solution of 3,4,5-trisbenzyloxy-6-benzyloxymethyl-2-(2,5-bis(trityloxymethyl)phenyl)tetrahydropyran-2-ol (242 mg, 0.21 mmol) in acetonitrile (3 ml), triethylsilane (36 μl, 0.23 mmol) and boron trifluoride diethyl ether complex (29 μl, 0.23 mmol) were added at −40° C. and the mixture was stirred at the same temperature for 1 hour. After stirring at 0° C. for an additional 1 hour, water was added and the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:4)) to give the titled compound (77.5 mg, 56%).

$^1$H-NMR (CDCl$_3$) δ: 3.62-3.71 (1H, d, J=11.1 Hz), 3.77-3.92 (3H, m), 4.07-4.18 (3H, m), 4.40-4.63 (6H, m), 4.83-4.95 (3H, m), 5.17 (2H, s), 6.75 (2H, s), 7.06-7.31 (25H, m)

MS (ESI$^+$): 681 [M+Na]$^+$

5) Synthesis of 1,1-anhydro-1-C-[5-formyl-2-(hydroxymethyl)phenyl]-2,3,4,6-tetra-O-benzyl-β-D-glucopyranose Under a nitrogen stream, to a solution of 1,1-anhydro-1-C-[2,5-bis-(hydroxymethyl)phenyl]-2,3,4,6-tetra-O-benzyl-β-D-glucopyranose (77.5 mg, 0.12 mmol) in methylene chloride (1.5 ml), Dess-Martin periodinane reagent (74.8 mg, 0.18 mmol) was added at room temperature and the mixture was stirred for 30 minutes. After addition of water, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:4)) to give the titled compound (25.2 mg, 33%).

$^1$H-NMR (CDCl$_3$) δ: 3.66 (1H, d, J=10.8 Hz), 3.76-3.95 (3H, m), 4.08-4.11 (1H, m), 4.15-4.27 (2H, m), 4.47 (2H, dd, J=12, 21.3 Hz), 4.65 (2H, d, J=10.8 Hz), 4.88 (1H, d, J=10.8 Hz), 4.95 (2H, s), 5.24 (2H, s), 6.77 (2H, d, J=6.9 Hz), 7.03-7.15 (3H, m), 7.19-7.41 (18H, m), 7.53 (1H, s), 7.87 (1H, d, J=7.8 Hz), 9.85 (1H, s)

MS (ESI$^+$): 679 [M+Na]$^+$

6) Synthesis of 1,1-anhydro-1-C-[5-(4-ethylphenyl)hydroxymethyl-2-(hydroxymethyl)phenyl]-2,3,4,6-tetra-O-benzyl-β-D-glucopyranose Under a nitrogen stream, to a solution of 1,1-anhydro-1-C-[5-formyl-2-(hydroxymethyl)phenyl]-2,3,4,6-tetra-O-benzyl-β-D-glucopyranose (25.2 mg, 0.038 mmol) in diethyl ether (0.3 ml), a THF solution of 4-ethylphenylmagnesium bromide (0.5 M, 153 μl, 0.077 mmol) was added at 0° C. and the mixture was stirred for 3 days at room temperature. After addition of water, the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:4)) to give the titled compound (23.3 mg, 80%).

$^1$H-NMR (CDCl$_3$) δ: 1.13 (3H, t, J=7.5 Hz), 2.53 (2H, q, J=7.2 Hz, J=7.8 Hz), 3.63 (1H, d, J=9.9 Hz), 3.78-3.90 (3H, m), 4.08-4.11 (2H, m), 4.43-4.64 (4H, m), 4.89 (3H, d, J=10.2 Hz), 5.17 (2H, s), 5.81 (1H, s), 6.67 (2H, s), 7.00-7.47 (25H, m)

7) Synthesis of 1,1-anhydro-1-C-[5-(4-ethylphenyl)methyl-2-(hydroxymethyl)phenyl]-2,3,4,6-tetra-O-benzyl-β-D-glucopyranose Under a nitrogen stream, to a solution of 1,1-anhydro-1-C-[5-(4-ethylphenyl)hydroxymethyl-2-(hydroxymethyl)phenyl]-2,3,4,6-tetra-O-benzyl-β-D-glucopyranose (23.3 mg, 0.031 mmol) in acetonitrile (1 ml), triethylsilane (5.8 μl, 0.037 mmol) and boron trifluoride diethyl ether complex (3.8 μl, 0.031 mmol) were added at −40° C. and the mixture was stirred at the same temperature for 2 hours. After addition of water, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:10)) to give the titled compound (18.9 mg, 83%).

$^1$H-NMR (CDCl$_3$) δ: 1.15 (3H, t, J=7.5 Hz), 2.55 (2H, q, J=7.2, 7.8 Hz), 3.63 (1H, d, J=9.3 Hz), 3.77-3.81 (1H, dd, J=3.6, 3.9 Hz), 3.83 (1H, s), 3.86 (1H, s), 3.95 (2H, s), 4.00 (1H, d, J=10.8 Hz), 4.06-4.11 (2H, m), 4.47 (2H, d, J=12 Hz), 4.60 (2H, d, J=12.3 Hz), 4.64 (1H, s), 4.84 (1H, d, J=3 Hz), 4.89 (2H, d, J=4.8 Hz), 5.17 (2H, dd, J=5.1, 12.3 Hz), 6.71 (2H, d, J=6.3 Hz), 6.96-7.31 (25H, m)

MS (ESI$^+$): 769 [M+Na]$^+$

8) Synthesis of 1,1-anhydro-1-C-[5-(4-ethylphenyl)methyl-2-(hydroxymethyl)phenyl]-β-D-glucopyranose To a solution of 1,1-anhydro-1-C-[5-(4-ethylphenyl)-methyl-2-(hydroxymethyl)phenyl]-2,3,4,6-tetra-O-benzyl-β-D-glucopyranose (18.9 mg, 0.025 mmol) in methanol (1 ml) and ethyl acetate (1 ml), 10% palladium catalyst (2 mg) was added. Under a hydrogen atmosphere, the reaction mixture was stirred for 5 hours at room temperature and then filtered to remove the catalyst. After distilling off the solvent under reduced pressure, the resulting residue was purified by silica gel column chromatography (developing solution=methylene chloride:methanol (10:1)) to give the titled compound (9.8 mg, 99%).

$^1$H-NMR (CD$_3$OD) δ: 1.19 (3H, t, J=7.5 Hz), 2.57 (2H, q, J=7.5, 7.8 Hz), 3.41-3.47 (1H, m), 3.64 (1H, dd, J=6 Hz), 3.73-3.83 (4H, m), 3.95 (2H, s), 5.11 (2H, dd, J=7.8, 12.3 Hz), 7.06-7.12 (4H, m), 7.16-7.23 (3H, m)

MS (ESI$^+$): 387[M+1]$^+$

HPLC retention time: 11.4 minutes

<HPLC Conditions>

Column: YMC-Pack ODS-A 6.0×150 mm, 5 μm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm

Example 2

1,1-Anhydro-1-C-[5-(2-benzothiophenyl)methyl-2-(hydroxymethyl)phenyl]-β-D-glucopyranose

1) Synthesis of 1,1-anhydro-1-C-[5-(2-benzothiophenyl)hydroxymethyl-2-(hydroxymethyl)phenyl]-2,3,4,6-tetra-O-benzyl-β-D-glucopyranose Under a nitrogen stream, to a solution of benzothiophene (51.8 mg, 0.386 mmol) in THF (750 μl), a hexane solution of n-butyllithium (2.71 M, 130 μl, 0.352 mmol) was added dropwise at −78° C. and the mixture was stirred for 10 minutes. After stirring at room temperature for 30 minutes, the reaction mixture was cooled to −78° C., and a solution of 1,1-anhydro-1-C-[5-formyl-2-(hydroxymethyl)phenyl]-2,3,4,6-tetra-O-benzyl-β-D-glucopyranose (207 mg, 0.315 mmol) in THF (450 μl) was added dropwise thereto. After stirring at room temperature for 1 hour, saturated aqueous ammonium chloride was added and the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel chromatography (developing solution=ethyl acetate:n-hexane (1:3)) to give the titled compound (266 mg) as a diastereomer mixture in quantitative yield.

$^1$H-NMR (CDCl$_3$) δ: 2.45 (0.6H, d, J=3.8 Hz), 2.56 (0.4H, d, J=4.0 Hz), 3.61-3.69 (1H, m), 3.75-3.87 (2H, m), 3.90 (1H, dd, J=9.6, 9.6 Hz), 4.05-4.18 (3H, m), 4.41-4.65 (4H, m), (3H, m), 5.21 (2H, s), 6.08 (0.4H, d, J=3.8 Hz), 6.11 (0.6H, d, J=4.0 Hz), 6.68-6.76 (2H, m), 7.00-7.40 (21H, m), (5H, m)

2) Synthesis of 1,1-anhydro-1-C-[5-(2-benzothiophenyl)methyl-2-(hydroxymethyl)phenyl]-2,3,4,6-tetra-O-benzyl-β-D-glucopyranose Under a nitrogen stream, to a solution of 1,1-anhydro-1-C-[5-(2-benzothiophenyl)-hydroxymethyl-2-(hydroxymethyl)phenyl]-2,3,4,6-tetra-O-benzyl-β-D-glucopyranose (249 mg, 0.315 mmol) in acetonitrile (3 ml), triethylsilane (60 µl, 0.376 mmol) and boron trifluoride diethyl ether complex (42 µl, 0.331 mmol) were added at −40° C. and the mixture was stirred at the same temperature for 2 hours. After addition of saturated aqueous potassium carbonate, the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel chromatography (developing solution=ethyl acetate:n-hexane (1:4)) to give the titled compound (103 mg, 42%) as a diastereomer mixture.

$^1$H-NMR (CDCl$_3$) δ: 3.66 (1H, dd, J=1.8, 11.1 Hz), 3.80 (1H, dd, J=3.7, 11.2 Hz), 3.84 (1H, dd, J=9.5, 9.5 Hz), 3.88 (1H, d, J=9.5 Hz), 4.05-4.15 (3H, m), 4.21 (1H, d, J=16.0 Hz), 4.25 (1H, d, J=16.0 Hz), 4.46 (1H, d, J=12.2 Hz), 4.49 (1H, d, J=10.7 Hz), 4.58 (1H, d, J=12.2 Hz), 4.61 (1H, d, J=10.7 Hz), 4.83-4.95 (3H, m), 5.18 (1H, d, J=12.7 Hz), 5.19 (1H, d, J=12.5 Hz), 6.74 (1H, dd, J=8.2, 1.7 Hz), 6.93 (1H, s), 7.06-7.36 (23H, m), 7.50 (1H, dd, J=7.2, 1.4 Hz), 7.61 (1H, d, J=7.9 Hz)

3) Synthesis of 1,1-anhydro-1-C-[5-(2-benzothiophenyl)methyl-2-(hydroxymethyl)phenyl]-β-D-glucopyranose Under a nitrogen stream, to a solution of 1,1-anhydro-1-C-[5-(2-benzothiophenyl)methyl-2-(hydroxymethyl)phenyl]-2,3,4,6-tetra-O-benzyl-β-D-glucopyranose (30.7 mg, 0.0396 mmol) and pentamethylbenzene (60.6 mg, 0.409 mmol) in dichloromethane (2 ml), a 1.0 M dichloromethane solution of boron trichloride (400 µl, 0.400 mmol) was added at −78° C. and the mixture was stirred at the same temperature for 1 hour. After addition of methanol, the reaction mixture was warmed to room temperature and evaporated under reduced pressure to remove the solvent. The resulting residue was purified by thin-layer chromatography (developing solution=methanol:dichloromethane (1:10)) to give the titled compound (10.4 mg, 63.8%).

$^1$H-NMR (CD$_3$OD) δ: 3.44 (1H, ddd, J=9.0, 5.3, 3.5 Hz), 3.65 (1H, dd, J=11.6, 5.3 Hz), 3.72-3.86 (4H, m), 4.27 (2H, s), 5.10 (1H, d, J=12.7 Hz), 5.14 (1H, d, J=12.7 Hz), 7.07 (1H, s), 7.18-7.37 (5H, m), 7.66 (1H, dd, J=1.5, 7.0 Hz), 7.72 (1H, d, J=8.1 Hz)

MS (ESI$^+$): 414 [M]$^+$

HPLC retention time: 12.3 minutes

<HPLC Conditions>

Column: YMC-Pack ODS-A 6.0×150 mm, 5 µm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm

Example 3

1,1-Anhydro-1-C-[5-(4-methoxyphenyl)methyl-2-(hydroxymethyl)phenyl]-β-D-glucopyranose

1) Synthesis of 1,1-anhydro-1-C-[5-(4-methoxyphenyl)hydroxymethyl-2-(hydroxymethyl)phenyl]-2,3,4,6-tetra-O-benzyl-β-D-glucopyranose Under a nitrogen stream, to a solution of 1,1-anhydro-1-C-[5-formyl-2-(hydroxymethyl)phenyl]-2,3,4,6-tetra-O-benzyl-β-D-glucopyranose (2.01 g, 3.06 mmol) in diethyl ether (24 ml), a THF solution of 4-methoxyphenylmagnesium bromide (0.5 M, 12.24 ml, 6.12 mmol) was added at 0° C. and the mixture was stirred for 2 hours and 30 minutes at room temperature. After addition of water, the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:4)) to give the titled compound (2.15 g, 92%).

$^1$H-NMR (CDCl$_3$) δ: 3.63 (1H, d, J=9.9 Hz), 3.69 (3H, s), 3.78-3.90 (3H, m), 4.08-4.11 (2H, m), 4.43-4.64 (4H, m), 4.89 (3H, d, J=10.2 Hz), 5.17 (2H, s), 5.81 (1H, s), 6.67 (2H, m), 7.06-7.48 (25H, m)

2) Synthesis of 1,1-anhydro-1-C-[5-(4-methoxyphenyl)methyl-2-(hydroxymethyl)phenyl]-2,3,4,6-tetra-O-benzyl-β-D-glucopyranose Under a nitrogen stream, to a solution of 1,1-anhydro-1-C-[5-(4-methoxyphenyl)hydroxymethyl-2-(hydroxymethyl)phenyl]-2,3,4,6-tetra-O-benzyl-β-D-glucopyranose (270 mg, 0.353 mmol) in methylene chloride (2.7 ml), triethylsilane (281 µl, 1.764 mmol) and boron trifluoride diethyl ether complex (47 µl, 0.37 mmol) were added at −40° C. and the mixture was stirred at the same temperature for 15 minutes. After addition of water, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:10)) to give the titled compound (260 mg, 90%).

$^1$H-NMR (CDCl$_3$) δ: 3.63 (1H, d, J=9.3 Hz), 3.69 (3H, s), 3.77-3.81 (1H, dd, J=3.9, 3.6 Hz), 3.83 (1H, s), 3.86 (1H, s), 3.92 (2H, s), 3.99 (1H, d, J=10.8 Hz), 4.06-4.14 (2H, m), 4.47 (2H, d, J=12 Hz), 4.56 (1H, s), 4.61 (2H, d, J=12.3 Hz), 4.84 (1H, d, J=3 Hz), 4.89 (2H, d, J=4.8 Hz), 5.16 (2H, dd, J=12.3, 5.1 Hz), 6.60-6.70 (4H, m), 6.98 (2H, d, J=6.3 Hz), 7.07-7.31 (21H, m)

3) Synthesis of 1,1-anhydro-1-C-[5-(4-methoxyphenyl)methyl-2-(hydroxymethyl)phenyl]-β-D-glucopyranose To a solution of 1,1-anhydro-1-C-[5-(4-methoxyphenyl)methyl-2-(hydroxymethyl)phenyl]-2,3,4,6-tetra-O-benzyl-β-D-glucopyranose (280 mg, 0.381 mmol) in methanol (1 ml) and ethyl acetate (1 ml), 10% palladium catalyst (28.7 mg) was added and 2N—HCl (15.2 µl) was further added. Under a hydrogen atmosphere, the reaction mixture was stirred for 45 minutes at room temperature and then filtered to remove the catalyst. After distilling off the solvent under reduced pressure, the resulting residue was purified by silica gel column chromatography (developing solution=methylene chloride:methanol (10:1)) to give the titled compound (114 mg, 98%).

$^1$H-NMR (CD$_3$OD) δ: 3.36-3.42 (1H, m), 3.60 (1H, dd, J=6 Hz), 3.70 (3H, s), 3.71-3.79 (4H, m), 3.88 (2H, s), 5.02 (2H, dd, J=12.3, 7.8 Hz), 6.74-6.78 (2H, m), 6.79-7.08 (2H, m), 7.12-7.18 (3H, m)

MS (ESI$^+$): 388 [M]$^+$

HPLC retention time: 9.62 minutes

<HPLC Conditions>

Column: YMC-Pack ODS-A 6.0×150 mm, 5 μm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm Example 4

1,1-Anhydro-1-C-[5-(4-isopropylphenyl)methyl-2-(hydroxymethyl)phenyl]-β-D-glucopyranose 1) Synthesis of 1,1-anhydro-1-C-[5-(4-isopropylphenyl)hydroxymethyl-2-(hydroxymethyl)phenyl]-2,3,4,6-tetra-O-benzyl-β-D-glucopyranose Under a nitrogen stream, a solution of 4-bromoisopropylbenzene (27.20 g, 136.62 mmol) in THF (242 ml) was cooled to −78° C., and a hexane solution of n-butyllithium (2.67 M, 54.37 ml) was added dropwise thereto. The reaction mixture was stirred at the same temperature for 1.5 hours. A solution of 1,1-anhydro-1-C-[5-formyl-2-(hydroxymethyl)phenyl]-2,3,4,6-tetra-O-benzyl-β-D-glucopyranose (56.08 g, 85.39 mmol) in THF (232 ml) was added dropwise and the mixture was stirred at −78° C. for 1.5 hours. Saturated aqueous ammonium chloride was added to stop the reaction. The reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:3)) to give the titled compound (57.78 g, 87%) as a diastereomer mixture.

$^1$H-NMR (CDCl$_3$) δ: 1.14 (6H, d, J=6.9 Hz), 2.08 (0.6H, d, J=3.3 Hz), 2.15 (0.4H, d, J=3.6 Hz), 2.75-2.81 (1H, m), 3.63-3.67 (1H, m), 3.76-4.15 (6H, m), 4.42-4.64 (4H, m), 4.84-4.94 (3H, m), 5.12-5.22 (2H, m), 5.80-5.84 (1H, m), 6.64-6.68 (2H, s), 7.02-7.49 (25H, m)

2) Synthesis of 1,1-anhydro-1-C-[5-(4-isopropylphenyl)methyl-2-(hydroxymethyl)phenyl]-2,3,4,6-tetra-O-benzyl-β-D-glucopyranose Under a nitrogen stream, to 1,1-anhydro-1-C-[5-(4-isopropylphenyl)hydroxymethyl-2-(hydroxymethyl)phenyl]-2,3,4,6-tetra-O-benzyl-β-D-glucopyranose (2.186 g, 2.81 mmol) in dichloromethane (28 ml), triethylsilane (2.24 ml, 14.02 mmol) and boron trifluoride diethyl ether complex (0.38 ml, 3.00 mmol) were added at −40° C. and the mixture was stirred at the same temperature for 1.5 hours. After addition of saturated aqueous potassium carbonate, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:5)) to give the titled compound (1.81 g, 85%).

$^1$H-NMR (CDCl$_3$) δ: 1.16 (6H, dd, J=6.9, 0.8 Hz), 2.77-2.81 (1H, m), 3.65 (1H, dd, J=11.0, 1.6 Hz), 3.78-3.87 (3H, m), 3.95-4.01 (3H, m), 4.06-4.15 (2H, m), 4.45 (2H, d, J=12.1 Hz), 4.56-4.63 (2H, m), 4.64 (1H, s), 4.85-4.94 (3H, m), 5.15 (2H, dd, J=17.6, 12.4 Hz), 6.68-6.71 (2H, m), 7.00-7.31 (25H, m)

3) Synthesis of 1,1-anhydro-1-C-[5-(4-isopropylphenyl)-methyl-2-(hydroxymethyl)phenyl]-β-D-glucopyranose To a solution of 1,1-anhydro-1-C-[5-(4-isopropylphenyl) methyl-2-(hydroxymethyl)phenyl]-2,3,4,6-tetra-O-benzyl-β-D-glucopyranose (1.78 g, 2.34 mmol) in methanol (11 ml) and ethyl acetate (11 ml), 10% palladium catalyst (0.22 g) was added. Under a hydrogen atmosphere, the reaction mixture was stirred for 1 hour at room temperature and then filtered to remove the catalyst. After distilling off the solvent under reduced pressure, the resulting residue was purified by silica gel column chromatography (developing solution=methylene chloride:methanol (10:1)) to give the titled compound (0.75 g, 80%).

$^1$H-NMR (CD$_3$OD) δ: 1.21 (6H, d, J=6.9 Hz), 2.82-2.86 (1H, m), 3.43-3.47 (1H, m), 3.64 (1H, dd, J=12.1, 5.8 Hz), 3.74-3.81 (4H, m), 3.95 (2H, s), 5.11 (2H, dd, J=19.5, 12.4 Hz), 7.11 (4H, s), 7.16-7.22 (3H, m)

MS (ESI$^+$): 401 [M+1]$^+$

HPLC retention time: 12.1 minutes

<HPLC Conditions>

Column: YMC-Pack ODS-A 6.0×150 mm, 5 μm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm Example 5

1,1-Anhydro-1-C-[5-(4-cyclopropylphenyl)methyl-2-(hydroxymethyl)phenyl]-β-D-glucopyranose 1) Synthesis of 1,1-anhydro-1-C-[5-(4-cyclopropylphenyl)hydroxymethyl-2-(hydroxymethyl)phenyl]-2,3,4,6-tetra-O-benzyl-β-D-glucopyranose Under a nitrogen stream, to a suspension of magnesium (0.27 g, 11.11 mmol) and 4-bromocyclopropylbenzene (2.00 g, 10.15 mmol) in ether (21 ml), 1,2-dibromoethane (0.014 ml, 0.16 mmol) was added. The reaction mixture was stirred at room temperature for 1.5 hours and then cooled to 0° C., followed by dropwise addition of a solution of 1,1-anhydro-1-C-[5-formyl-2-(hydroxymethyl)phenyl]-2,3,4,6-tetra-O-benzyl-β-D-glucopyranose (5.10 g, 7.77 mmol) in ether (21 ml). After stirring at 0° C. for 1 hour, saturated aqueous ammonium chloride was added to stop the reaction. The reaction mixture was extracted twice with ether. The organic layer was washed with saturated aqueous sodium chloride, dried over anhydrous magnesium sulfate, and then evaporated under reduced pressure to remove the solvent. The resulting residue was purified by silica gel chromatography (developing solution=n-hexane:acetone (3:1)) to give the titled compound (5.18 g, 86%).

$^1$H-NMR (CDCl$_3$) δ: 0.55-0.59 (2H, m), 0.86-0.92 (2H, m), 1.75-1.82 (1H, m), 2.12 (1H, d, J=3.6 Hz), 3.62-4.15 (7H, m), 4.43-4.64 (4H, m), 4.86-4.90 (3H, m), 5.12-5.21 (2H, m), 5.78-5.88 (1H, m), 6.65-6.69 (1H, m), 6.85-7.41 (26H, m)

2) Synthesis of 1,1-anhydro-1-C-[5-(4-cyclopropylphenyl)methyl-2-(hydroxymethyl)phenyl]-2,3,4,6-tetra-O-benzyl-β-D-glucopyranose Under a nitrogen stream, to 1,1-anhydro-1-C-[5-(4-cyclopropylphenyl)hydroxymethyl-2-(hydroxymethyl)phenyl]-2,3,4,6-tetra-O-benzyl-β-D-glucopyranose (5.16 g, 6.66 mmol) in dichloromethane (67 ml), triethylsilane (5.30 ml, 33.18 mmol) and boron trifluoride diethyl ether complex (0.91 ml, 7.18 mmol) were added at −40° C. and the mixture was stirred at the same temperature for 1.5 hours. After addition of saturated aqueous potassium carbonate, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:4)) to give the titled compound (4.27 g, 85%).

$^1$H-NMR (CDCl$_3$) δ: 0.56-0.58 (2H, m), 0.86-0.90 (2H, m), 1.74-1.84 (1H, m), 3.63-3.67 (1H, m), 3.77-3.86 (3H, m), 3.94 (2H, s), 3.99 (1H, d, J=10.4 Hz), 4.07-4.14 (2H, m), 4.45 (2H, d, J=12.1 Hz), 4.56-4.63 (2H, m), 4.85-4.90 (3H, m), 5.11-5.20 (2H, m), 6.68-6.71 (2H, m), 6.83-6.86 (2H, m), 6.97 (2H, d, J=8.2 Hz), 7.09-7.31 (21H, m)

3) Synthesis of 1,1-anhydro-1-C-[5-(4-cyclopropylphenyl)methyl-2-(hydroxymethyl)phenyl]-β-D-glucopyranose Under a nitrogen stream, to a solution of 1,1-anhydro-1-C-[5-(4-cyclopropylphenyl)methyl-2-(hydroxymethyl)phenyl]-2,3,4,6-tetra-O-benzyl-β-D-glucopyranose (2.55 g, 3.36 mmol) and pentamethylbenzene (4.99 g, 33.66 mmol) in dichloromethane (185 ml), a 1.0 M dichloromethane solution of boron trichloride (33.26 ml, 33.26 mmol) was added at −78° C. and the mixture was stirred at the same temperature for 2 hours. After addition of methanol (185 ml), the reaction mixture was warmed to room temperature and evaporated under reduced pressure to remove the solvent. The resulting residue was purified by thin-layer chromatography (developing solution=methanol:dichloromethane (1:10)) to give the titled compound (0.67 g, 50%).

$^1$H-NMR (CD$_3$OD) δ: 0.59-0.64 (2H, m), 0.87-0.94 (2H, m), 1.82-1.87 (1H, m), 3.40-3.47 (1H, m), 3.61 (1H, dd, J=12.1, 5.8 Hz), 3.74-3.83 (4H, m), 3.94 (2H, s), 5.09 (2H, dd, J=20.3, 12.4 Hz), 6.94-6.97 (2H, m), 7.05-7.08 (2H, m), 7.19 (3H, m)

MS (ESI$^+$): 398 [M]$^+$

HPLC retention time: 11.4 minutes

<HPLC Conditions>

Column: YMC-Pack ODS-A 6.0×150 mm, 5 μm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm

Example 6

1,1-Anhydro-1-C-[5-(4-n-propylphenyl)methyl-2-(hydroxymethyl)phenyl]-β-D-glucopyranose 1,1-Anhydro-1-C-[5-(4-cyclopropylphenyl)-methyl-2-(hydroxymethyl)phenyl]-2,3,4,6-tetra-O-benzyl-β-D-glucopyranose obtained in Example 5 (1.68 g, 2.21 mmol) was dissolved in methanol (10 ml) and ethyl acetate (10 ml). To this solution, 10% palladium catalyst (0.21 g) was added. Under a hydrogen atmosphere, the reaction mixture was stirred for 1.5 hours at room temperature and then filtered to remove the catalyst. After distilling off the solvent under reduced pressure, the resulting residue was purified by silica gel column chromatography (developing solution=methylene chloride:methanol (10:1)) to give the titled compound (0.65 g, 73%).

$^1$H-NMR (CD$_3$OD) δ: 0.92 (3H, t, J=7.4 Hz), 1.57-1.64 (2H, m), 2.50-2.55 (2H, m), 3.43-3.49 (1H, m), 3.65 (1H, dd, J=11.8, 5.5 Hz), 3.75-3.85 (4H, m), 3.95 (2H, s), 5.09 (2H, dd, J=19.2, 12.4 Hz), 7.04-7.22 (7H, m)

MS (ESI$^+$): 401 [M+1]$^+$

HPLC retention time: 12.3 minutes

<HPLC Conditions>

Column: YMC-Pack ODS-A 6.0×150 mm, 5 μm

Mobile phase: 20 minute gradient from 0.1% TFA/MeCN (5%)+0.1% TFA/H$_2$O (95%) to 0.1% TFA/MeCN (100%), followed by 5 minute elution under the same conditions (0.1% TFA/MeCN (100%))

Flow rate: 1.5 ml/minute

Column temperature: room temperature

Detection conditions: total plot summed over the entire wavelength range of 230 to 400 nm

Example 7

1,1-Anhydro-1-C-[5-(4-ethylphenyloxy)-2-(hydroxymethyl)phenyl]-β-D-glucopyranose

1) Synthesis of 2-bromo-4-(ethylphenoxy)-benzoic acid methyl ester

To a solution of 2-bromo-4-fluoro-benzoic acid methyl ester (488 mg, 2.09 mmol) in anhydrous DMF (15 ml), 4-ethylphenol (256 mg, 2.09 mmol) and potassium carbonate (289 mg, 2.09 mmol) were added at room temperature, followed by stirring under a nitrogen atmosphere for 16 hours at 160° C. The reaction mixture was cooled and, after addition of saturated aqueous ammonium chloride, was then extracted with ethyl acetate. The organic layer was washed with saturated aqueous sodium chloride and dried over sodium sulfate. After filtration, the solvent was distilled off under reduced pressure and the resulting residue was purified by silica gel column chromatography (developing solution=ethyl acetate: n-hexane (1:20)) to give the titled compound (455 mg, 65%).

¹H-NMR (CDCl₃) δ: 1.26 (3H, t, J=7.6 Hz), 2.67 (2H, q, J=7.6 Hz), 3.90 (3H, s), 6.88-6.93 (1H, m), 6.94-7.01 (2H, m), 7.19-7.26 (3H, m), 7.83 (1H, d, J=8.7 Hz)

2) Synthesis of [2-bromo-4-(4-ethylphenoxy)phenyl]methanol

Under a nitrogen stream, to a solution of 2-bromo-4-(ethylphenoxy)-benzoic acid methyl ester (90 mg, 0.269 mmol) in anhydrous toluene (2 ml), a toluene solution of DIBAL (1M, 0.537 ml, 0.537 mmol) was added dropwise at −78° C. The reaction mixture was stirred at −78° C. for 1.5 hours and at room temperature for 1.5 hours. The reaction mixture was cooled again to −78° C., followed by addition of 1N hydrochloric acid (0.2 ml) and ether (3.5 ml). The reaction mixture was extracted with ethyl acetate. The organic layer was washed with saturated aqueous sodium chloride and dried over sodium sulfate. After filtration, the solvent was distilled off under reduced pressure and the resulting residue was purified by silica gel column chromatography (developing solution=ethyl acetate:n-hexane (1:5)) to give the titled compound (78 mg, 94%).

¹H-NMR (CDCl₃) δ: 1.25 (3H, t, J=7.6 Hz), 2.65 (2H, q, J=7.6 Hz), 4.71 (2H, s), 6.91-6.97 (3H, m), 7.15-7.21 (3H, m), 7.39 (1H, d, J=8.4 Hz)

3) Synthesis of (2-trityloxymethyl)-5-(4-ethylphenoxy)-phenyl bromide

Under a nitrogen stream, to a solution of [2-bromo-4-(4-ethylphenoxy)phenyl]methanol (493 mg, 1.61 mmol) in a mixture of anhydrous DMF (5 ml) and methylene chloride (5 ml), trityl chloride (492 mg, 1.77 mmol), triethylamine (0.247 ml, 1.77 mmol) and 4-dimethylaminopyridine (50 mg) were added. The reaction mixture was stirred at room temperature for 12 hours. After addition of water, the reaction mixture was extracted with ethyl acetate. The organic layer was washed with saturated aqueous sodium chloride and dried over sodium sulfate. After filtration, the solvent was distilled off under reduced pressure and the resulting residue was purified by silica gel column chromatography (developing solution=ethyl acetate:n-hexane (1:9)) to give the titled compound (880 mg, 99%).

¹H-NMR (CDCl₃) δ: 1.25 (3H, t, J=7.6 Hz), 2.65 (2H, q, J=7.6 Hz), 4.19 (2H, s), 6.91-7.34 (15H, m), 7.49-7.53 (6H, m), 7.64-7.68 (1H, m)

4) Synthesis of 3,4,5-tris-benzyloxy-6-benzyloxymethyl-2-[5-(4-ethylphenoxy)-2-trityloxymethylphenyl]tetrahydropyran-2-ol Under a nitrogen stream, to a solution of (2-trityloxymethyl)-5-(4-ethylphenoxy)phenyl bromide (766 mg, 1.39 mmol) in anhydrous THF (15 ml), a hexane solution of n-butyllithium (1.6 M, 0.92 ml, 1.47 mmol) was added dropwise at −78° C. and the mixture was stirred for 15 minutes. To this solution was added a solution of 3,4,5-trisbenzyloxy-6-(benzyloxymethyl)tetrahydropyran-2-one (751 mg, 1.39 mmol) in anhydrous THF (1.5 ml) dropwise at −78° C. and the resulting solution was stirred at the same temperature for 10 minutes. After addition of saturated aqueous ammonium chloride, the reaction mixture was extracted with ethyl acetate. The organic layer was washed with saturated aqueous sodium chloride, dried over anhydrous sodium sulfate, and then evaporated under reduced pressure to remove the solvent. The resulting residue was purified by silica gel column chromatography (developing solution=ethyl acetate:n-hexane (1:7)) to give the titled compound (615 mg, 43%).

¹H-NMR (CDCl₃) δ: 1.22 (3H, t, J=7.6 Hz), 2.62 (2H, q, J=7.6 Hz), 3.30-3.59 (4H, m), 3.80-4.05 (3H, m), 4.25-4.39 (5H, m), 4.46-4.62 (2H, m), 4.72-4.85 (3H, m), 6.80-7.59 (42H, m)

5) Synthesis of 1,1-anhydro-1-C-[5-(4-ethylphenoxy)-2-(hydroxymethyl)-phenyl]-2,3,4,6-tetra-O-benzyl-β-D-glucopyranose Under a nitrogen stream, to a solution of 3,4,5-tris-benzyloxy-6-benzyloxymethyl-2-[5-(4-ethylphenoxy)-2-trityloxymethylphenyl]tetrahydropyran-2-ol (547 mg, 0.54 mmol) in methylene chloride (10 ml), triethylsilane (0.095 ml, 0.60 mmol) and TFA (0.046 ml, 0.60 mmol) were added at 0° C., followed by stirring at room temperature for 2 hours. After addition of saturated aqueous potassium carbonate, the reaction mixture was extracted with methylene chloride. The organic layer was washed with saturated aqueous sodium chloride, dried over anhydrous sodium sulfate, and then evaporated under reduced pressure to remove the solvent. The resulting residue was purified by silica gel column chromatography (developing solution=ethyl acetate:n-hexane (1:4)) to give the titled compound (405 mg, 99%).

¹H-NMR (CDCl₃) δ: 1.22 (3H, t, J=7.6 Hz), 2.62 (2H, q, J=7.6 Hz), 3.59-3.87 (4H, m), 4.04-4.21 (3H, m), 4.41-4.68 (4H, m), 4.81-4.95 (3H, m), 5.11-5.24 (2H, m), 6.77-6.91 (4H, m), 6.95 (1H, d, J=1.9 Hz), 7.01-7.36 (22H, m)

MS (ESI⁺): 772 [M+Na]⁺

6) Synthesis of 1,1-anhydro-1-C-[5-(4-ethylphenoxy)-2-(hydroxymethyl)phenyl]-β-D-glucopyranose To a solution of 1,1-anhydro-1-C-[5-(4-ethylphenoxy)-2-(hydroxymethyl)phenyl]-2,3,4,6-tetra-O-benzyl-β-D-glucopyranose (429 mg, 0.57 mmol) in a mixture of ethyl acetate (12 ml) and methanol (12 ml), 10% palladium catalyst (400 mg) was added. Under a hydrogen atmosphere, the reaction mixture was stirred for 12 hours at room temperature and then filtered to remove the catalyst. After distilling off the solvent under reduced pressure, the resulting residue was purified by silica gel column chromatography (developing solution=methylene chloride:methanol (10:1)) to give the titled compound (195 mg, 88%).

¹H-NMR (CD₃OD) δ: 1.23 (3H, t, J=7.6 Hz), 2.63 (2H, q, J=7.6 Hz), 3.40-3.46 (1H, m), 3.63-3.85 (5H, m), 5.10 (2H, m), 6.87-7.03 (4H, m), 7.14-7.28 (3H, m)

MS (ESI⁺): 411 [M+Na]⁺

Example 8

1,1-Anhydro-1-C-[5-(4-ethylphenyl)methyl-2-(2-hydroxyethyl)thiophen-3-yl]-β-D-glucopyranose

1) Synthesis of (4-bromo-thiophen-2-yl)-(4-ethylphenyl)-methanol

Under a nitrogen stream, to a solution of 4-bromo-2-thiophenecarboxaldehyde (10.0 g, 52.3 mmol) in anhydrous THF (100 ml), a hexane solution of n-butyllithium (1.6 M, 34.35 ml, 55.0 mmol) was added dropwise at −78° C. over 5 minutes. After stirring at the same temperature for 10 minutes, a solution of 1-bromo-4-ethylbenzene (10.2 g, 55.0 mmol) in THF (50 ml) was added dropwise. The reaction mixture was stirred at −78° C. for 2 hours and, after addition of saturated aqueous ammonium chloride, was then extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:10)) to give the titled compound (7.1 g, 45%).

$^1$H-NMR (CDCl$_3$) δ: 1.24 (3H, t, J=7.5 Hz), 2.42 (1H, s), 2.65 (2H, q, J=7.5 Hz), 5.93 (1H, s), 6.76 (1H, s), 7.14 (1H, s), 7.20 (2H, d, J=8.1 Hz), 7.32 (2H, d, J=8.1 Hz)

2) Synthesis of 4-bromo-2-(4-ethyl-phenyl)-methyl-thiophene

Under a nitrogen stream, to a solution of (4-bromo-thiophen-2-yl)-(4-ethyl-phenyl)-methanol (7.10 g, 23.9 mmol) in methylene chloride (70 ml), triethylsilane (4.6 ml, 28.7 mmol) and boron trifluoride diethyl ether complex (3.33 ml, 26.3 mmol) were added at 0° C., followed by stirring at room temperature for 2 hours. After addition of 50% methanol-water (1 ml), the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:50)) to give the titled compound (3.4 g, 51%).

$^1$H-NMR (CDCl$_3$) δ: 1.23 (3H, t, J=7.5 Hz), 2.63 (2H, q, J=7.5 Hz), 4.06 (2H, s), 6.70 (1H, s), 7.02 (1H, s), 7.14 (4H, s)

3) Synthesis of 2-[3-bromo-5-((4-ethylphenyl)methyl)thiophen-2-yl]ethanol

Under a nitrogen stream, to 4-bromo-2-((4-ethylphenyl)methyl)thiophene (2.80 g, 10.0 mmol) in anhydrous THF (40 ml), LDA (2.0 M, 5.50 ml, 11.0 ml) was added dropwise at −78° C. over 5 minutes. After the reaction mixture was stirred at 0° C. for 30 minutes, a THF solution of ethylene oxide (10 ml) was added dropwise at −78° C. The reaction mixture was warmed to room temperature and stirred for 3 hours. After addition of water, the reaction mixture was extracted with ether. The organic layer was washed with saturated aqueous sodium chloride, dried over anhydrous sodium sulfate, and then evaporated under reduced pressure to remove the solvent. The resulting residue was purified by silica gel column chromatography (developing solution=ethyl acetate:n-hexane (1:9)) to give the titled compound (2.55 g, 78%).

$^1$H-NMR (CDCl$_3$) δ: 1.23 (3H, t, J=7.5 Hz), 1.60 (1H, s), 2.63 (2H, q, J=7.5 Hz), 2.96 (2H, t, J=6.3 Hz), 3.80 (2H, t, J=6.3 Hz), 4.00 (2H, s), 6.62 (1H, s), 7.14 (4H, s)

4) Synthesis of 3-bromo-5-(4-ethylphenyl)-methyl-2-(2-trityloxyethyl)thiophene

Under a nitrogen stream, to a solution of 2-[3-bromo-5-((4-ethylphenyl)methyl)thiophen-2-yl]-ethanol (2.55 g, 7.84 mmol) in a mixture of anhydrous DMF (15 ml) and methylene chloride (15 ml), trityl chloride (3.29 g, 11.8 mmol) was added. To this solution, triethylamine (1.64 ml, 11.8 mmol) and 4-dimethylaminopyridine (77 mg, 0.63 mmol) were added at 0° C. The reaction mixture was stirred at 40° C. for 4 hours. After addition of water, the reaction mixture was extracted with methylene chloride. The organic layer was washed with saturated aqueous sodium chloride and dried over sodium sulfate. After filtration, the solvent was distilled off under reduced pressure and the resulting residue was purified by silica gel column chromatography (developing solution=ethyl acetate:n-hexane (1:20)) to give the titled compound (3.60 g, 81%).

$^1$H-NMR (CDCl$_3$) δ: 1.22 (3H, t, J=7.5 Hz), 2.62 (2H, q, J=7.5 Hz), 2.96 (2H, t, J=6.3 Hz), 3.26 (2H, t, J=6.3 Hz), 4.00 (2H, s), 6.60 (1H, s), 7.12 (4H, s), 7.12-7.27 (9H, m), 7.37-7.40 (6H, m)

5) Synthesis of 3,4,5-tris-benzyloxy-6-benzyloxymethyl-2-[5-(4-ethylphenyl)methyl-2-(2-trityloxyethyl)thiophen-3-yl]-tetrahydropyran-2-ol Under a nitrogen stream, to a solution of 3-bromo-5-((4-ethylphenyl)methyl)-2-(2-trityloxyethyl)thiophene (1.45 g, 2.55 mmol) in anhydrous THF (40 ml), a hexane solution of n-butyllithium (1.6 M, 1.76 ml, 2.81 mmol) was added dropwise at −78° C. and the mixture was stirred for 15 minutes. To this solution was added a solution of 3,4,5-trisbenzyloxy-6-(benzyloxymethyl)tetrahydropyran-2-one (1.50 g, 2.81 mmol) in anhydrous THF (10 ml) dropwise at −78° C. and the resulting solution was stirred at the same temperature for 10 minutes. After addition of saturated aqueous ammonium chloride, the reaction mixture was extracted with ethyl acetate. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:20)) to give the titled compound (1.70 g, 65%).

$^1$H-NMR (CDCl$_3$) δ: 1.22 (3H, t, J=4.5 Hz), 2.56 (1H, d, J=9.3 Hz), 2.62 (2H, q, J=4.5 Hz), 3.26-3.31 (2H, m), 3.39 (1H, d, J=6.0 Hz), 3.47 (1H, d, J=5.4 Hz), 3.75-4.08 (8H, m), 4.48 (2H, t, J=7.5 Hz), 4.60 (1H, d, J=7.2 Hz), 4.66 (1H, d, J=6.6 Hz), 4.87 (2H, q, J=3.3 Hz), 4.95 (1H, d, J=6.6 Hz), 5.25 (1H, s), 6.84 (1H, s), 7.02-7.31 (39H, m)

MS (ESI$^+$): 1049 [M+Na]$^+$

6) Synthesis of 1,1-anhydro-1-C-[5-(4-ethyl-phenyl)-methyl-2-(2-hydroxyethyl)-thiophen-3-yl]-2,3,4,6-tetra-O-benzyl-β-D-glucopyranose Under a nitrogen stream, to a solution of 3,4,5-tris-benzyloxy-6-benzyloxymethyl-2-[5-(4-ethyl-benzyl)-2-(2-trityloxy-ethyl)-thiophen-3-yl]-tetrahydropyran-2-ol (1.70 g, 1.68 mmol) in methylene chloride (60 ml), triethylsilane (0.30 ml, 1.85 mmol) and diethyl ether complex (0.234 ml, 1.85 mmol) were added at 0° C., followed by stirring at room temperature for 2 hours. After addition of saturated aqueous potassium carbonate, the reaction mixture was extracted with methylene chloride. The organic layer was washed with saturated aqueous sodium chloride, dried over anhydrous magnesium sulfate, and then evaporated under reduced pressure to remove the solvent. The resulting residue was purified by silica gel column chromatography (developing solution=ethyl acetate:n-hexane (1:9)) to give the titled compound (1.14 g, 84%).

$^1$H-NMR (CDCl$_3$) δ: 1.19 (3H, t, J=4.5 Hz), 2.56-2.59 (3H, m), 3.02-3.09 (1H, m), 3.69 (1H, d, J=6.0 Hz), 3.75-3.81 (3H, m), 3.95-4.12 (6H, m), 4.18 (1H, d, J=7.3 Hz), 4.50 (2H, dd, J=6.9, 9.0 Hz), 4.60 (2H, m), 4.86 (2H, d, J=5.4 Hz), 4.93 (1H, d, J=6.6 Hz), 6.62 (1H, s), 6.88 (2H, d, J=3.9 Hz), 7.03 (2H, d, J=4.8 Hz), 7.08 (2H, d, J=4.8 Hz), 7.16-7.33 (18H, m)

MS (ESI$^+$): 789 [M+Na]$^+$

7) Synthesis of 1,1-anhydro-1-C-[(4-ethyl-phenyl)-methyl-2-(2-hydroxyethyl)-thiophen-3-yl]-β-D-glucopyranose Under a nitrogen stream, to a solution of 1,1-anhydro-1-C-[5-(4-ethylphenyl)methyl-2-(2-hydroxyethyl)thiophen-3-yl]-2,3,4,6-tetra-O-benzyl-β-D-glucopyranose (1.14 g, 1.46 mmol) in anhydrous methylene chloride (50 ml), pentamethylbenzene (3.25 g, 21.9 mmol) was added at −78° C. Boron trichloride (14.6 ml, 14.6 mmol) was further added, followed by stirring at −78° C. for 2 hours. After addition of methanol, the solvent was distilled off under reduced pressure and the resulting residue was purified by silica gel column chromatography (developing solution=methylene chloride:methanol (20:1)) to give the titled compound (350 mg, 59%).

$^1$H-NMR (CD$_3$OD) δ: 1.20 (3H, t, J=7.5 Hz), 2.52-2.64 (3H, m), 2.93-3.03 (1H, m), 3.34-3.37 (1H, m), 3.61-3.83 (5H, m), 3.96-4.05 (4H, m), 6.67 (1H, s), 7.09-7.15 (4H, m)

MS (ESI$^+$): 407 [M+1]$^+$

Example 9

1,1-Anhydro-1-C-[5-(4-biphenyl)-methyl-2-hydroxymethyl]phenyl]-β-D-glucopyranose

1) Synthesis of 1,1-anhydro-1-C-[2,5-bis-(hydroxymethyl)phenyl]-β-D-glucopyranose 1,1-Anhydro-1-C-[2,5-bis-(hydroxymethyl)phenyl]-2,3,4,6-tetra-O-benzyl-β-D-glucopyranose synthesized in Example 1 (0.59 g, 0.90 mmol) and pentamethylbenzene (1.33 g, 8.95 mmol) were dissolved in dichloromethane (48 ml). To this solution, under a nitrogen stream, a 1.0 M dichloromethane solution of boron trichloride (8.95 ml, 8.95 mmol) was added at −78° C. and the mixture was stirred at the same temperature for 2 hours. After addition of methanol (48 ml), the reaction mixture was warmed to room temperature and evaporated under reduced pressure to remove the solvent. The resulting residue was purified by thin-layer chromatography (developing solution=methanol:dichloromethane (1:6)) to give the titled compound (0.18 g, 67%).

$^1$H-NMR (CD$_3$OD) δ: 3.47-3.50 (1H, m), 3.63-3.69 (1H, m), 3.75-3.85 (4H, m), 4.63 (2H, s), 5.13 (2H, dd, J=12.6, 19.5 Hz), 7.23-7.37 (3H, m)

MS (ESI$^+$): 299 [M+1]$^+$

2) Synthesis of 1,1-anhydro-1-C-[5-chloromethyl-2-(hydroxymethyl)phenyl]-2,3,4,6-tetra-O-acetyl-β-D-glucopyranose Under a nitrogen stream, to a solution of 1,1-anhydro-1-C-[2,5-bis(hydroxymethyl)phenyl]-β-D-glucopyranose (100 mg, 0.34 mmol) in DMSO (0.19 ml, 2.68 mmol), chlorotrimethylsilane (114 μl, 0.91 mmol) was added dropwise at room temperature and the mixture was stirred at the same temperature for 1.5 hours. To the crude product obtained by distilling off volatile components, N-methylmorpholine (0.74 ml, 6.70 mmol), 4-dimethylaminopyridine (41 mg, 0.34 mmol) and acetic anhydride (0.32 ml, 3.35 mmol) were added sequentially and the mixture was stirred on ice for 1 hour and 10 minutes. After addition of saturated aqueous sodium chloride (1 ml) and water (1 ml), the reaction mixture was extracted with ethyl acetate (10 ml). The organic layer was washed with water (1.5 ml) and saturated aqueous sodium chloride (1 ml), dried over sodium sulfate, and then concentrated under reduced pressure. The resulting residue was purified by flash column chromatography (developing solution=ethyl acetate:n-hexane (1:2.5)) to give the titled compound (122.9 mg, 76%).

$^1$H-NMR (CDCl$_3$) δ: 1.74 (3H, s), 2.01 (3H, s), 2.05 (1H, s), 2.08 (3H, s), 3.99-4.08 (1H, m), 4.24-4.37 (2H, m), 4.61 (2H, s), 5.12-5.34 (3H, m), 5.56-5.67 (2H, m), 7.22-7.28 (1H, m), 7.38-7.47 (2H, m)

3) Synthesis of 1,1-anhydro-1-C-[5-(4-biphenyl)-methyl-2-(hydroxymethyl)phenyl]-2,3,4,6-tetra-O-acetyl-β-D-glucopyranose Under a nitrogen stream, to a solution of 1,1-anhydro-1-C-[5-chloromethyl-2-(hydroxymethyl)phenyl]-2,3,4,6-tetra-O-acetyl-β-D-glucopyranose (250 mg, 0.516 mmol) in toluene (2.5 ml), triphenylphosphine (20.3 mg, 0.078 mmol), palladium acetate (8.7 mg, 0.039 mmol), 4-biphenylboronic acid (204 mg, 1.03 mmol) and potassium phosphate (219 mg, 1.03 mmol) were added. The reaction mixture was heated to 80° C. and stirred for 15 hours. After addition of water and ethyl acetate, the reaction mixture was washed with saturated aqueous sodium chloride. The organic layer was dried over magnesium sulfate, filtered and then evaporated under reduced pressure to remove the solvent. The residue was purified by flash column chromatography (developing solution=ethyl acetate:hexane (1:2)) to give the titled compound (280 mg, 90%).

$^1$H-NMR (CDCl$_3$) δ: 1.71 (3H, s), 2.00 (3H, s), 2.05 (3H, s), 2.06 (3H, s), 4.04 (2H, s), 4.25-4.36 (2H, m), 5.17 (2H, dd, J=12.5, 25.8 Hz), 5.26-5.33 (2H, m), 5.58-5.63 (2H, m), 7.15-7.34 (6H, m), 7.39-7.44 (2H, m), 7.51-7.58 (4H, m)

4) Synthesis of 1,1-anhydro-1-C-[5-(4-biphenyl)methyl-2-(hydroxymethyl)phenyl]-β-D-glucopyranose To a solution of 1,1-anhydro-1-C-[5-(4-biphenyl)-methyl-2-(hydroxymethyl)phenyl]-2,3,4,6-tetra-O-acetyl-β-D-glucopyranose (280 mg, 0.465 mmol) in methanol (3.0 ml), potassium carbonate (45 mg, 0.326 mmol) was added and the mixture was stirred at room temperature for 1 hour. After addition of water, the reaction mixture was extracted with ethyl acetate. The organic layer was washed with saturated aqueous sodium chloride and dried over magnesium sulfate. After filtration, the solvent was concentrated under reduced pressure. The resulting residue was purified by flash column chromatography (developing solution=methanol:methylene:chloride (1:15)) to give the titled compound (84 mg, 42%).

$^1$H-NMR (CD$_3$OD) δ: 3.40-3.51 (1H, m), 3.63-3.69 (1H, m), 3.75-3.84 (4H, m), 4.04 (2H, s), 5.11 (2H, m), 7.20-7.31 (6H, m), 7.37-7.42 (2H, m), 7.50-7.58 (4H, m)

MS (ESI$^+$): 457 [M+Na]$^+$

Example 10

1,1-Anhydro-1-C-[5-(4-((S)-tetrahydrofuran-3-yloxy)phenyl)-methyl-2-(hydroxymethyl)phenyl]-β-D-glucopyranose

1) Synthesis of 1,1-anhydro-1-C-[5-(4-benzyloxyphenyl)-methyl-2-(hydroxymethyl)phenyl]-2,3,4,6-tetra-O-acetyl-β-D-glucopyranose Using 1,1-anhydro-1-C-[5-chloromethyl-2-(hydroxymethyl)phenyl]-2,3,4,6-tetra-O-acetyl-β-D-glucopyranose and appropriate reagents, the same procedure as used in Example 9 was repeated to give the titled compound.

$^1$H-NMR (CDCl$_3$) δ: 1.70 (3H, s), 2.00 (3H, s), 2.05 (3H, s), 2.07 (3H, s), 3.94 (2H, s), 4.01-4.09 (1H, m), 4.23-4.36 (2H, m), 5.04 (2H, s), 5.15 (2H, dd, J=12.6, 25.9 Hz), 5.24-5.33 (1H, m), 5.53-5.66 (2H, m), 6.85-6.94 (2H, m), 7.03-7.47 (10H, m)

MS (ESI$^+$): 655 [M+Na]$^+$

2) Synthesis of 1,1-anhydro-1-C-[5-(4-hydroxyphenyl)methyl-2-(hydroxymethyl)phenyl]-2,3,4,6-tetra-O-acetyl-β-D-glucopyranose To a solution of 1,1-anhydro-1-C-[5-(4-benzyloxyphenyl)methyl-2-(hydroxymethyl)phenyl]-2,3,4,6-tetra-O-acetyl-β-D-glucopyranose (250 mg, 0.57 mmol) in a mixture of THF (7 ml) and methanol (7 ml), 10% palladium catalyst (200 mg) was added. Under a hydrogen atmosphere, the reaction mixture was stirred at 35° C. for 12 hours and then filtered to remove the catalyst. After distilling off the solvent under reduced pressure, the resulting residue was purified by silica gel column chromatography (developing solution=ethyl acetate:n-hexane (1:1)) to give the titled compound (193 mg, 90%).

$^1$H-NMR (CDCl$_3$) δ: 1.70 (3H, s), 2.00 (3H, s), 2.05 (3H, s), 2.07 (3H, s), 3.93 (2H, s), 4.01-4.09 (1H, m), 4.23-4.36 (2H, m), 4.65 (1H, s), 5.15 (2H, dd, J=12.2, 25.9 Hz), 5.24-5.33 (1H, m), 5.53-5.66 (2H, m), 6.72-6.78 (2H, m), 6.98-7.05 (2H, m), 7.11-7.24 (3H, m)

MS (ESI$^+$): 565 [M+Na]$^+$

3) Synthesis of 1,1-anhydro-1-C-[5-(4-((S)-tetrahydrofuran-3-yloxy)-phenyl)-methyl-2-(hydroxymethyl)phenyl]-2,3,4,6-tetra-O-acetyl-β-D-glucopyranose To a solution of 1,1-anhydro-1-C-[5-(4-hydroxyphenyl)methyl-2-(hydroxymethyl)phenyl]-2,3,4,6-tetra-O-acetyl-β-D-glucopyranose (190 mg, 0.35 mmol) in DMF (3 ml), (R)-p-toluenesulfonic acid tetrahydrofuran-3-yl ester (102 mg, 0.42 mmol) and cesium carbonate (137 mg, 0.42 mmol) were added and the mixture was stirred at room temperature for 12 hours. After addition of water, the reaction mixture was extracted with ethyl acetate. The organic layer was washed with saturated aqueous sodium chloride and dried over sodium sulfate. After filtration, the solvent was concentrated under reduced pressure. The resulting residue was purified by flash column chromatography (developing solution=ethyl acetate:n-hexane (1:2)) to give the titled compound (170 mg, 79%).

$^1$H-NMR (CDCl$_3$) δ: 1.71 (3H, s), 2.00 (3H, s), 2.04 (3H, s), 2.07 (3H, s), 2.12-2.21 (2H, m), 3.84-4.08 (7H, m), 4.22-4.36 (2H, m), 4.85-4.93 (1H, m), 5.16 (2H, dd, J=12.5, 25.7 Hz), 5.24-5.33 (1H, m), 5.53-5.66 (2H, m), 6.74-6.81 (2H, m), 7.01-7.10 (2H, m), 7.11-7.19 (2H, m), 7.23 (1H, s)

MS (ESI$^+$): 635 [M+Na]$^+$

4) Synthesis of 1,1-anhydro-1-C-[5-(4-((S)-tetrahydrofuran-3-yloxy)-phenyl)-methyl-2-(hydroxymethyl)phenyl]-β-D-glucopyranose Using 1,1-anhydro-1-C-[5-(4-((S)-tetrahydrofuran-3-yloxy)phenyl)-methyl-2-(hydroxymethyl)phenyl]-2,3,4,6-tetra-O-acetyl-β-D-glucopyranose and appropriate reagents, the same procedure as used in Example 9 was repeated to give the titled compound.

$^1$H-NMR (CD$_3$OD) δ: 2.00-2.28 (2H, m), 3.39-3.49 (1H, m), 3.60-3.98 (11H, m), 4.92-5.00 (1H, m), 5.10 (2H, m), 6.76-6.84 (2H, m), 7.08-7.15 (2H, m), 7.17-7.25 (3H, m)

MS (ESI$^+$): 467 [M+Na]$^+$

Example 11

1,1-Anhydro-1-C-[5-(4-((R)-tetrahydrofuran-3-yloxy)phenyl)-methyl-2-(hydroxymethyl)phenyl]-β-D-glucopyranose Using 1,1-anhydro-1-C-[5-chloromethyl-2-(hydroxymethyl)phenyl]-2,3,4,6-tetra-O-acetyl-β-D-glucopyranose and appropriate reagents, the same procedure as used in Example 10 was repeated to give the titled compound.

$^1$H-NMR (CD$_3$OD) δ: 2.01-2.29 (2H, m), 3.39-3.49 (1H, m), 3.60-4.01 (11H, m), 4.92-5.00 (1H, m), 5.10 (2H, m), 6.77-6.84 (2H, m), 7.08-7.16 (2H, m), 7.17-7.25 (3H, m)

MS (ESI$^+$): 467 [M+Na]$^+$

Example 12

1,1-Anhydro-1-C-[5-(4-ethynylphenyl)methyl-2-(hydroxymethyl)phenyl]-β-D-glucopyranose

1) Synthesis of 1,1-anhydro-1-C-[5-(4-trifluoromethanesulfonyloxyphenyl)methyl-2-(hydroxymethyl)phenyl]-2,3,4,6-tetra-O-acetyl-β-D-glucopyranose 1,1-Anhydro-1-C-[5-(4-hydroxyphenyl)methyl-2-(hydroxymethyl)phenyl]-2,3,4,6-tetra-O-acetyl-β-D-glucopyranose synthesized in Example 10 (185 mg, 0.341 mmol) was dissolved in anhydrous methylene chloride (5.0 ml). To this solution, under a nitrogen stream, pyridine (0.083 ml, 1.02 mmol) was added at room temperature, and trifluoromethanesulfonic acid anhydride (0.086 ml, 0.511 mmol) was further added dropwise. The reaction mixture was stirred for 2 hours at room temperature. After distilling off the solvent under reduced pressure, the resulting residue was purified by flash column chromatography (developing solution=ethyl acetate:n-hexane (1:1)) to give the titled compound (217 mg, 94%).

$^1$H-NMR (CDCl$_3$) δ: 1.70 (3H, s), 2.00 (3H, s), 2.05 (3H, s), 2.07 (3H, s), 3.97-4.15 (3H, m), 4.23-4.37 (2H, m), 5.17 (2H, dd, J=12.6, 25.9 Hz), 5.24-5.33 (1H, m), 5.54-5.66 (2H, m), 7.13-7.33 (7H, m)

2) Synthesis of 1,1-anhydro-1-C-[5-(4-trimethylsilanylethynylphenyl)methyl-2-(hydroxymethyl)phenyl]-2,3,4,6-tetra-O-acetyl-β-D-glucopyranose Under a nitrogen stream, 1,1-Anhydro-1-C-[5-(4-trifluoromethanesulfonyloxyphenyl)methyl-2-(hydroxymethyl)phenyl]-2,3,4,6-tetra-O-acetyl-β-D-glucopyranose (212 mg, 0.314 mmol), trimethylsilylacetylene (0.089 ml, 0.628 mmol), triethylamine (0.2 ml, 1.44 mmol) and dichlorobis(triphenylphosphine)palladium (11.0 mg, 0.016 mmol) were mixed. To this mixture, anhydrous DMF (3 ml) was added and the mixture was stirred at 90° C. for 4 hours. The reaction mixture was diluted with water and extracted with ethyl acetate. The organic layer was washed with saturated aqueous sodium chloride and dried over sodium sulfate. After filtration, the solvent was concentrated under reduced pressure. The resulting residue was purified by flash column chromatography (developing solution=ethyl acetate:n-hexane (1:2)) to give the titled compound (95 mg, 48%).

$^1$H-NMR (CDCl$_3$) δ: 0.23 (9H, s), 1.70 (3H, s), 2.00 (3H, s), 2.05 (3H, s), 2.07 (3H, s), 3.93-4.08 (3H, m), 4.23-4.37 (2H, m), 5.16 (2H, dd, J=12.6, 25.2 Hz), 5.24-5.33 (1H, m), 5.51-5.66 (2H, m), 7.04-7.18 (4H, m), 7.22 (1H, s), 7.35-7.42 (2H, m)

3) Synthesis of 1,1-anhydro-1-C-[5-(4-ethynylphenyl)methyl-2-(hydroxymethyl)phenyl]-β-D-glucopyranose Using 1,1-anhydro-1-C-[5-(4-trimethylsilanylethynylphenyl)methyl-2-(hydroxymethyl)phenyl]-2,3,4,6-tetra-O-acetyl-β-D-glucopyranose and appropriate reagents, the same procedure as used in Example 9 was repeated to give the titled compound.

$^1$H-NMR (CD$_3$OD) δ: 3.40 (1H, s), 3.41-3.49 (1H, m), 3.62-3.70 (1H, m), 3.72-3.85 (4H, m), 4.01 (2H, s), 5.11 (2H, m), 7.17-7.25 (5H, m), 7.34-7.40 (2H, m)

MS (ESI$^+$): 383 [M+1]$^+$

Example 13

1,1-Anhydro-1-C-[5-(4-hydroxyphenyl)methyl-2-(hydroxymethyl)phenyl]-β-D-glucopyranose Using 1,1-anhydro-1-C-[5-(4-hydroxyphenyl)methyl-2-(hydroxymethyl)phenyl]-2,3,4,6-tetra-O-acetyl-β-D-glucopyranose synthesized in Example 10 and appropriate reagents, the same procedure as used in Example 9 was repeated to give the titled compound.

$^1$H-NMR (CD$_3$OD) δ: 3.39-3.52 (1H, m), 3.61-3.71 (1H, m), 3.72-3.85 (4H, m), 3.90 (2H, s), 5.10 (2H, m), 6.64-6.74 (2H, m), 6.97-7.06 (2H, m), 7.15-7.25 (3H, m)

MS (ESI$^+$): 397 [M+Na]$^+$

Example 14

1,1-Anhydro-1-C-[5-(4-pyrazol-1-yl-phenyl)methyl-2-(hydroxymethyl)phenyl]-β-D-glucopyranose

1) Synthesis of 4-pyrazol-1-yl-phenylboronic acid

Under a nitrogen stream, to a solution of 1-(4-bromophenyl)-1H-pyrazole (995 mg, 4.46 mmol) in anhydrous THF (12 ml), a hexane solution of n-butyllithium (1.6 M, 2.79 ml, 4.46 mmol) was added dropwise at −78° C. After stirring at the same temperature for 1 hour, this solution was added dropwise at −78° C. to a solution of trimethyl borate (1.07 ml, 9.37 mmol) in anhydrous THF (8 ml). After stirring at the same temperature for 1 hour, the reaction mixture was stirred at room temperature for one day and a night. After addition of saturated aqueous ammonium chloride, the reaction mixture was extracted with ethyl acetate. The organic layer was washed with saturated aqueous sodium chloride and dried over magnesium sulfate. After filtration, the solvent was concentrated under reduced pressure. The resulting residue was purified by flash column chromatography (developing solution=methylene chloride:methanol (50:1)) to give the titled compound (314 mg, 37%).

$^1$H-NMR (CDCl$_3$) δ: 6.45-6.50 (1H, m), 7.52-7.64 (4H, m), 7.72 (1H, d, J=1.5 Hz), 7.89 (1H, d, J=2.3 Hz)

MS (ESI$^+$): 189 [M+1]$^+$

2) Synthesis of 1,1-anhydro-1-C-[5-(4-pyrazol-1-ylphenyl)methyl-2-(hydroxymethyl)phenyl]-β-D-glucopyranose Using 4-pyrazol-1-yl-phenylboronic acid, 1,1-anhydro-1-C-[5-chloromethyl-2-(hydroxymethyl)phenyl]-2,3,4,6-tetra-O-acetyl-β-D-glucopyranose and appropriate reagents, the same procedure as used in Example 9 was repeated to give the titled compound.

$^1$H-NMR (CD$_3$OD): 3.40-3.52 (1H, m), 3.61-3.70 (1H, m), 3.72-3.85 (4H, m), 4.05 (2H, s), 5.11 (2H, dd, J=12.6, 19.8 Hz), 6.46-6.52 (1H, m), 7.19-7.39 (5H, m), 7.59-7.72 (3H, m), 8.12-8.17 (1H, m)

MS (ESI$^+$): 425 [M+1]$^+$

Example 15

1,1-Anhydro-1-C-[5-(4-methoxyphenyl)ethyl-2-(hydroxymethyl)phenyl]-β-D-glucopyranose

1) Synthesis of 1,1-anhydro-1-C-[5-(4-methoxyphenyl)ethyl-2-(hydroxymethyl)phenyl]-2,3,4,6-tetra-O-acetyl-β-D-glucopyranose Under a nitrogen stream, to a solution of 1,1-anhydro-1-C-[5-chloromethyl-2-(hydroxymethyl)phenyl]-2,3,4,6-tetra-O-acetyl-β-D-glucopyranose (200 mg, 0.41 mmol) in anhydrous THF (1.0 ml), a THF solution of lithium tetrachlorocuprate (0.1 M, 0.124 ml, 0.012 mmol) and N-methylpyrrolidinone (0.16 ml, 1.64 mmol) were added dropwise at room temperature. A THF solution of 4-methoxybenzylmagnesium bromide (0.25 M, 1.72 ml) was added dropwise over 5 minutes at room temperature. The reaction mixture was stirred at room temperature for one day and a night. After addition of 2N hydrochloric acid (2 ml), the reaction mixture was extracted with ethyl acetate. The organic layer was washed with saturated aqueous sodium chloride and dried over magnesium sulfate. After filtration, the solvent was concentrated under reduced pressure. The resulting residue was purified by flash column chromatography (developing solution=ethyl acetate:n-hexane (2:3)) to give the titled compound (13 mg, 6%).

$^1$H-NMR (CDCl$_3$) δ: 1.73 (3H, s), 2.01 (3H, s), 2.05 (3H, s), 2.08 (3H, s), 2.80-2.95 (4H, m), 3.79 (3H, s), 4.01-4.07 (1H, m), 4.27-4.37 (2H, m), 5.13 (1H, d, J=12.3 Hz), 5.21 (1H, d, J=12.3 Hz), 5.27-5.34 (1H, m), 5.57-5.67 (2H, m), 6.80 (2H, d, J=8.6 Hz), 7.07 (2H, d, J=8.6 Hz), 7.14 (2H, s), 7.25-7.26 (1H, m)

2) Synthesis of 1,1-anhydro-1-C-[5-(4-methoxyphenyl)ethyl-2-(hydroxymethyl)phenyl]-β-D-glucopyranose Using 1,1-anhydro-1-C-[5-(4-methoxyphenyl)ethyl-2-(hydroxymethyl)phenyl]-2,3,4,6-tetra-O-acetyl-β-D-glucopyranose and appropriate reagents, the same procedure as used in Example 9 was repeated to give the titled compound.

$^1$H-NMR (CD$_3$OD): 2.70-2.90 (4H, m), 3.38-3.44 (1H, m), 3.57-3.78 (8H, m), 5.02 (1H, d, J=12.3 Hz), 5.07 (1H, d, J=12.3 Hz), 6.74 (2H, d, J=8.7 Hz), 7.03 (2H, d, J=8.7 Hz), 7.10 (2H, m), 7.15 (1H, s)

MS (ESI$^+$): 402 [M]$^+$

Tables 1-1 and 1-2 show the structural formulae of the compounds prepared in the above examples. The compounds listed in Tables 1-3 to 1-8 can also be readily prepared in the same manner as shown in the above examples or production schemes with or without minor modifications obvious to those skilled in the art.

TABLE 1-1
Example 1
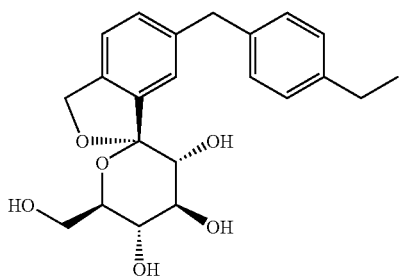
Example 2
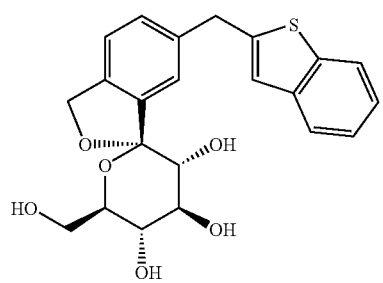
Example 3
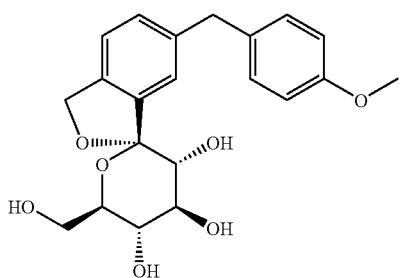
Example 4
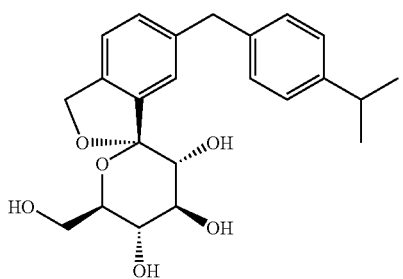
Example 5
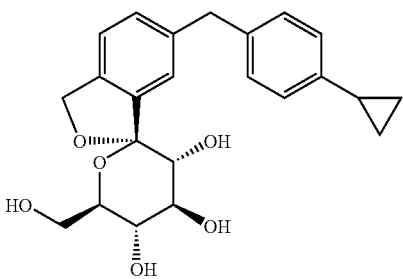
TABLE 1-1-continued
Example 6
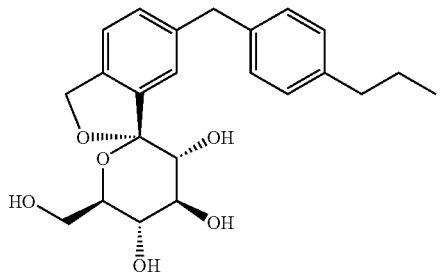
Example 7
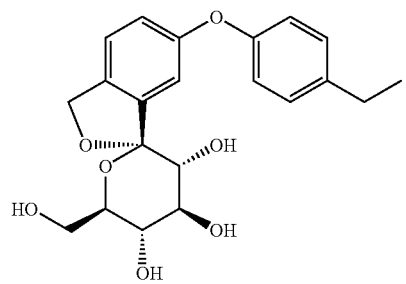
Example 8
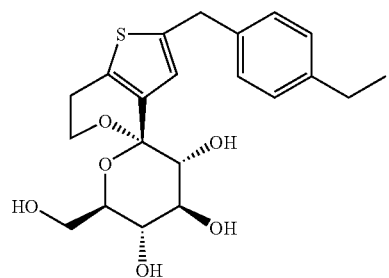
Example 9
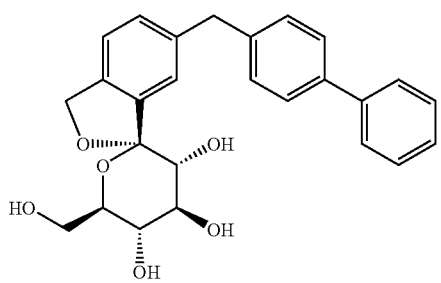
Example 10
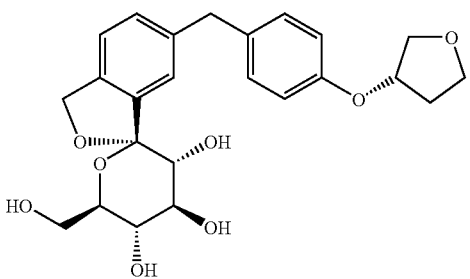

TABLE 1-2
Example 11 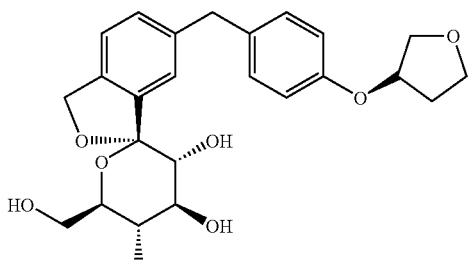
Example 12 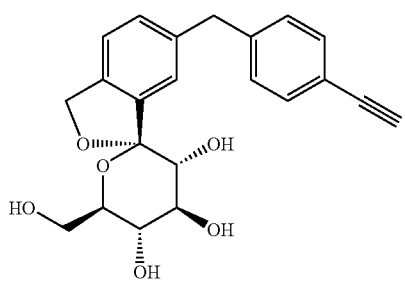
Example 13 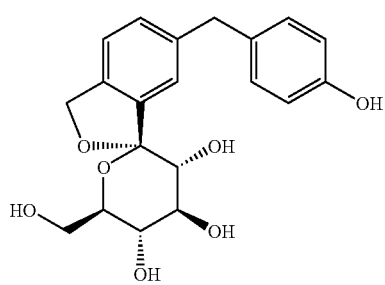
TABLE 1-2-continued
Example 14 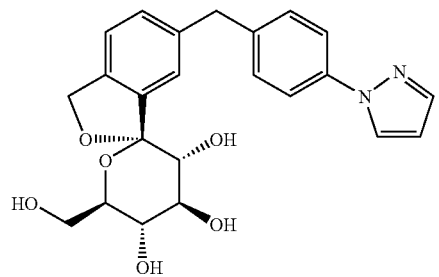
Example 15 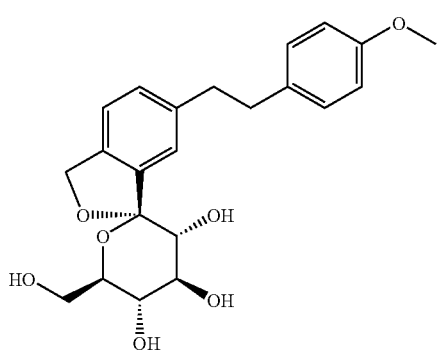
TABLE 1-3
| Example 16 | 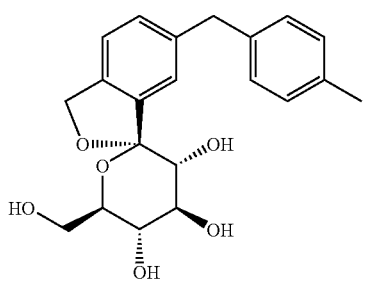 | $^1$H-NMR (CD$_3$OD) δ: 2.28 (3H, s), 3.41-3.50 (1H, m), 3.62-3.68 (1H, m), 3.75-3.83 (4H, m), 3.95 (2H, s), 5.10 (2H, m), 7.04-7.10 (4H, m), 7.17-7.22 (3H, m)<br>MS (ESI+): 395 [M + Na]$^+$ |
|---|---|---|
| Example 17 | 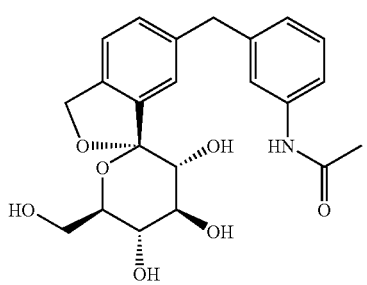 | $^1$H-NMR (CD$_3$OD) δ: 2.08 (3H, s), 3.44-3.51 (1H, m), 3.63-3.69 (1H, m), 3.75-3.84 (4H, m), 3.98 (2H, s), 5.10 (2H, m), 6.96 (1H, d, J = 7.6 Hz), 7.17-7.25 (4H, m), 7.36-7.38 (2H, m)<br>MS (ESI+): 438 [M + Na]$^+$ |

TABLE 1-3-continued
| Example 18 | 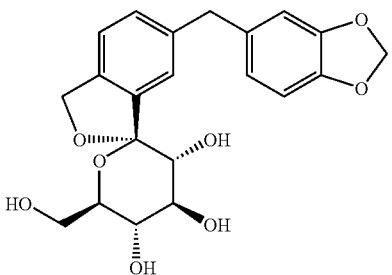 | ¹H-NMR (CD₃OD) δ: 3.40-3.50 (1H, m), 3.62-3.68 (1H, m), 3.74-3.84 (4H, m), 3.91 (2H, s), 5.10 (2H, m), 5.87 (2H, s), 6.67-6.70 (3H, m), 7.21 (3H, s)<br>MS (ESI+): 425 [M + Na]⁺ |
| --- | --- | --- |
| Example 19 | 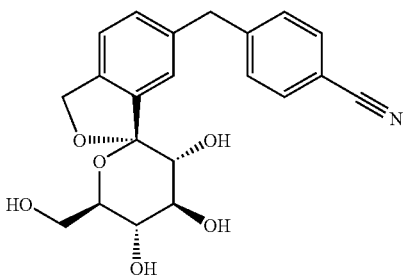 | ¹H-NMR (CD₃OD) δ: 3.37-3.50 (1H, m), 3.62-3.68 (1H, m), 3.74-3.84 (4H, m), 4.10 (2H, s), 5.11 (2H, m), 7.24 (3H, s), 7.41 (2H, d, J = 8.1 Hz), 7.62 (2H, d, J = 8.1 Hz)<br>MS (ESI+): 406 [M + Na]⁺ |
| Example 20 | 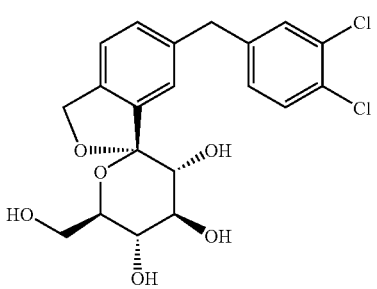 | ¹H-NMR (CD₃OD) δ: 3.40-3.51 (1H, m), 3.63-3.69 (1H, m), 3.73-3.84 (4H, m), 3.99 (2H, s), 5.11 (2H, m), 7.13-7.17 (1H, m), 7.24 (3H, s), 7.36-7.41 (2H, m)<br>MS (ESI+): 449 [M + Na]⁺ |
TABLE 1-4
| Example 21 | 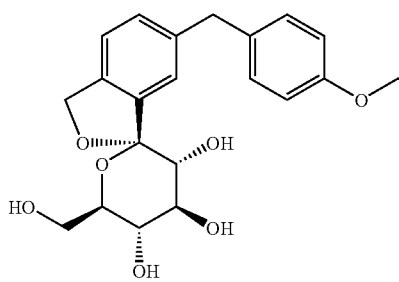 | ¹H-NMR (CD₃OD) δ: 1.35 (3H, t, J = 6.9 Hz), 3.39-3.49 (1H, m), 3.61-3.69 (1H, m), 3.72-3.85 (4H, m), 3.93 (2H, s), 3.99 (2H, q, J = 6.9 Hz), 5.10 (2H, m), 6.77-6.83 (2H, m), 7.07-7.14 (2H, m), 7.20 (3H, m)<br>MS (ESI+): 403 [M + 1]⁺ |
| --- | --- | --- |
| Example 22 | 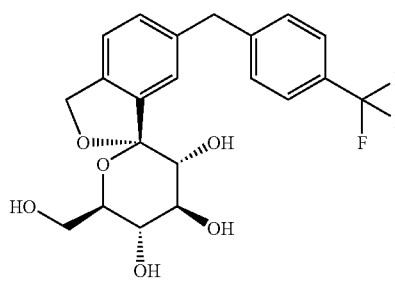 | ¹H-NMR (CD₃OD) δ: 3.39-3.50 (1H, m), 3.61-3.71 (1H, m), 3.71-3.85 (4H, m), 4.10 (2H, s), 5.11 (2H, m), 7.25 (3H, s), 7.37-7.45 (2H, m), 7.52-7.60 (2H, m)<br>MS (ESI+): 427 [M + 1]⁺ |

TABLE 1-4-continued
| Example 23 | 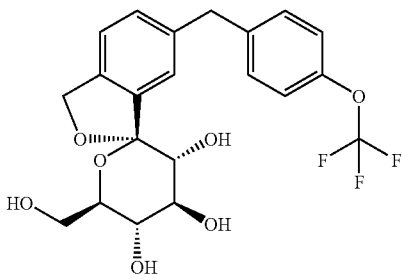 | $^1$H-NMR (CD$_3$OD) δ: 3.40-3.50 (1H, m), 3.62-3.70 (1H, m), 3.73-3.85 (4H, m), 4.03 (2H, s), 5.11 (2H, m), 7.11-7.36 (7H, m)<br>MS (ESI+): 443 [M + 1]$^+$ |
| --- | --- | --- |
| Example 24 | 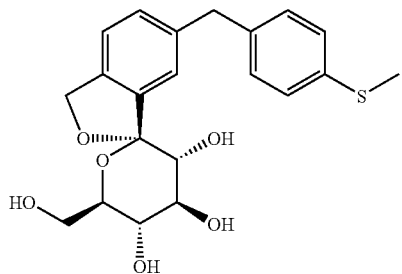 | $^1$H-NMR (CD$_3$OD) δ: 2.43 (3H, s), 3.38-3.50 (1H, m), 3.62-3.68 (1H, m), 3.72-3.85 (4H, m), 3.96 (2H, s), 5.10 (2H, m), 7.12-7.25 (7H, m)<br>MS (ESI+): 405 [M + 1]$^+$ |
| Example 25 | 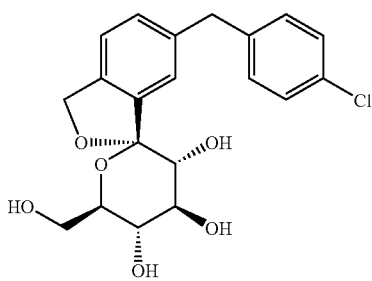 | $^1$H-NMR (CD$_3$OD) δ: 3.38-3.51 (1H, m), 3.58-3.70 (1H, m), 3.71-3.85 (4H, m), 3.99 (2H, s), 5.11 (2H, m), 7.15-7.29 (7H, m)<br>MS (ESI+): 393 [M + 1]$^+$ |
TABLE 1-5
| Example 26 | 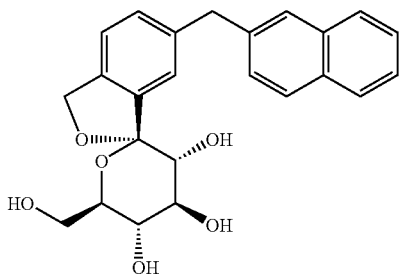 | $^1$H-NMR (CD$_3$OD) δ: 3.39-3.49 (1H, m), 3.59-3.70 (1H, m), 3.71-3.86 (4H, m), 4.17 (2H, s), 5.12 (2H, m), 7.20-7.49 (6H, m), 7.68 (1H, s), 7.71-7.83 (3H, m)<br>MS (ESI+): 431 [M + Na]$^+$ |
| --- | --- | --- |
| Example 27 | 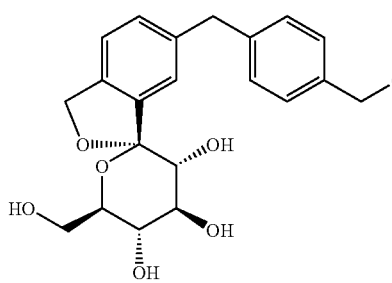 | $^1$H-NMR (CD$_3$OD) δ: 3.40-3.48 (1H, m), 3.60-3.70 (1H, m), 3.72-3.86 (4H, m), 4.00 (2H, s), 4.56 (2H, s), 5.11 (2H, m), 7.15-7.32 (7H, m)<br>MS (ESI+): 411 [M + Na]$^+$ |

TABLE 1-5-continued
| Example 28 | 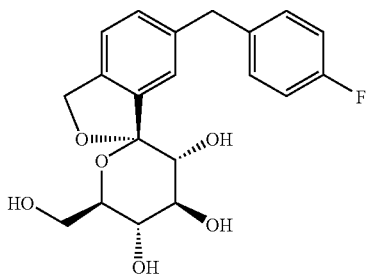 | $^1$H-NMR (CD$_3$OD) δ: 3.39-3.48 (1H, m), 3.62-3.68 (1H, m), 3.75-3.84 (4H, m), 3.99 (2H, s), 5.11 (2H, m), 6.97 (2H, t, J = 8.8 Hz), 7.19-7.23 (5H, m)<br>MS (ESI+): 399 [M + Na]$^+$ |
|---|---|---|
| Example 29 | 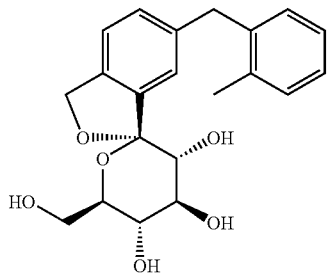 | $^1$H-NMR (CD$_3$OD) δ: 2.25 (3H, s), 3.40-3.46 (1H, dd, J = 9.8, 8.7 Hz), 3.61-3.67 (1H, m), 3.70-3.84 (4H, m), 4.03 (2H, s), 5.10 (2H, m), 7.12-7.20 (7H, m)<br>MS (ESI+): 395 [M + Na]$^+$ |
| Example 30 | 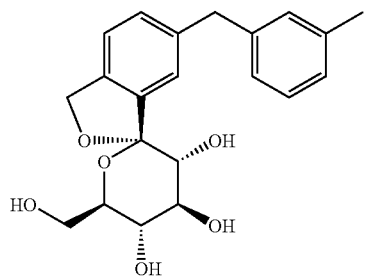 | $^1$H-NMR (CD$_3$OD) δ: 2.27 (3H, s), 3.42-3.48 (1H, m), 3.62-3.68 (1H, m), 3.75-3.85 (4H, m), 3.95 (2H, s), 5.10 (2H, m), 6.99 (3H, t, J = 7.1 Hz), 7.10-7.22 (4H, m)<br>MS (ESI+): 373 [M + 1]$^+$ |
TABLE 1-6
| Example 31 | 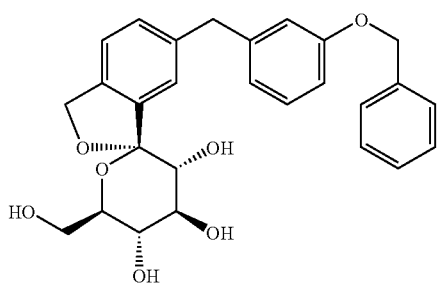 | $^1$H-NMR (CD$_3$OD) δ: 3.42-3.48 (1H, m), 3.62-3.68 (1H, m), 3.76-3.79 (4H, m), 3.96 (2H, s), 5.03 (2H, s), 5.11 (2H, m), 6.83-7.22 (3H, m), 6.83-7.22 (4H, m), 7.28-7.41 (5H, m)<br>MS (ESI+): 465 [M + 1]$^+$ |
|---|---|---|
| Example 32 | 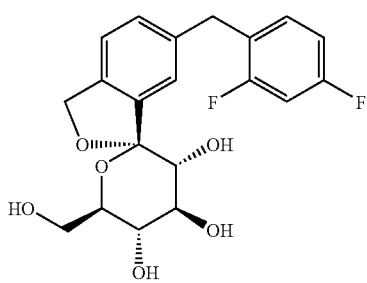 | $^1$H-NMR (CD$_3$OD) δ: 3.42-3.48 (1H, m), 3.62-3.68 (1H, m), 3.76-3.84 (4H, m), 4.00 (2H, s), 5.10 (2H, m), 6.84-6.94 (2H, m), 7.22-7.26 (4H, m)<br>MS (ESI+): 395 [M + 1]$^+$ |

TABLE 1-6-continued

| Example 33 | 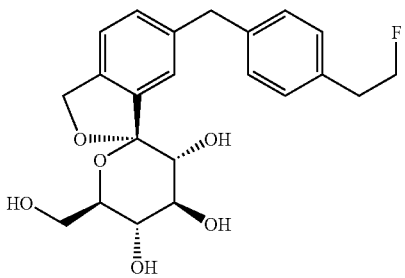 | $^1$H-NMR (CD$_3$OD) δ: 2.83 (1H, d, J = 6.5 Hz), 2.92 (1H, d, J = 6.5 Hz), 3.34-3.41 (1H, m), 3.55-3.62 (1H, m), 3.69-3.77 (4H, m), 3.91 (2H, s), 4.41 (1H, d, J = 6.5 Hz), 4.58 (1H, d, J = 6.5 Hz), 5.04 (2H, d, J = 6.5 Hz), 7.09-7.15 (7H, m) MS (ESI+): 405 [M]$^+$ |
|---|---|---|
| Example 34 | 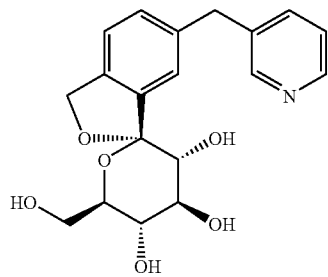 | $^1$H-NMR (CD$_3$OD) δ: 3.40-3.51 (1H, m), 3.62-3.68 (1H, m), 3.74-3.84 (4H, m), 4.06 (2H, s), 5.11 (2H, m), 7.19-7.27 (3H, m), 7.32-7.36 (1H, m), 7.67-7.71 (1H, m), 8.35-8.37 (1H, m), 8.44 (1H, d, J = 1.7 Hz) MS (ESI+): 360 [M + 1]$^+$ |
| Example 35 | 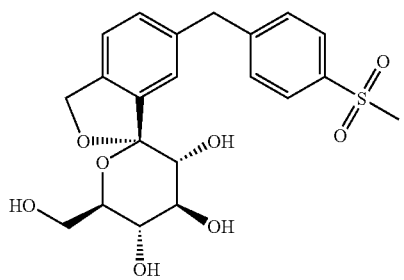 | $^1$H-NMR (CD$_3$OD) δ: 3.08 (3H, s), 3.41-3.48 (1H, m), 3.62-3.68 (1H, m), 3.74-3.80 (4H, m), 4.13 (2H, s), 5.11 (2H, m), 7.22-7.27 (3H, m), 7.49 (2H, d, J = 8.3 Hz), 7.85 (2H, d, J = 8.4 Hz) MS (ESI+): 437 [M + 1]$^+$ |

TABLE 1-7

| Example 36 | 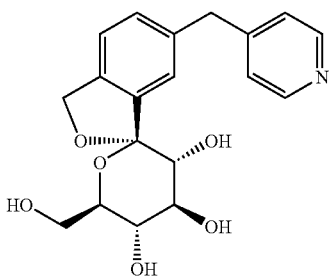 | $^1$H-NMR (CD$_3$OD) δ: 3.40-3.51 (1H, m), 3.63-3.69 (1H, m), 3.75-3.85 (4H, m), 4.07 (2H, s), 5.12 (2H, m), 7.26-7.31 (5H, m), 8.40 (2H, d, J = 5.8 Hz) MS (ESI+): 360 [M + 1]$^+$ |
|---|---|---|
| Example 37 | 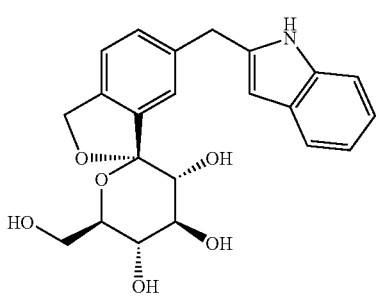 | $^1$H-NMR (CD$_3$OD) δ: 3.40-3.50 (1H, m), 3.63-3.68 (1H, m), 3.74-3.84 (4H, m), 4.13 (2H, s), 5.12 (2H, m), 6.12 (1H, s), 6.89-7.02 (2H, m), 7.22-7.24 (2H, m), 7.31-7.34 (2H, m), 7.40 (1H, d, J = 7.5 Hz) MS (ESI+): 398 [M + 1]$^+$ |

TABLE 1-7-continued

| Example 38 | (structure) | ¹H-NMR (CD₃OD) δ: 3.39-3.46 (1H, m), 3.60-3.66 (1H, m), 3.72-3.82 (4H, m), 3.89 (2H, s), 5.07 (2H, m), 6.56-6.67 (3H, m), 7.01-7.06 (1H, m), 7.18-7.20 (3H, m)<br>MS (ESI+): 397 [M + Na]⁺ |
|---|---|---|
| Example 39 | (structure) | ¹H-NMR (CD₃OD) δ: 3.42-3.48 (1H, m), 3.62-3.68 (1H, m), 3.74-3.84 (4H, m), 3.98 (2H, s), 5.05-5.18 (3H, m), 5.70 (1H, dd, J = 17.6, 1.1 Hz), 6.68 (1H, dd, J = 17.6, 11.0 Hz), 7.15-7.23 (5H, m), 7.32 (2H, d, J = 8.2 Hz)<br>MS (ESI+): 407 [M + Na]⁺ |
| Example 40 | (structure) | ¹H-NMR (CD₃OD) δ: 3.49-3.56 (1H, m), 3.69-3.75 (1H, m), 3.81-3.91 (4H, m), 3.93 (3H, s), 4.13 (s, 2H), 5.17 (2H, m), 7.26-7.31 (3H, m), 7.39 (2H, d, J = 8.2 Hz), 7.98 (2H, d, J = 8.4 Hz)<br>MS (ESI+): 439 [M + Na]⁺ |

TABLE 1-8

| Example 41 | (structure) | ¹H-NMR (CD₃OD) δ: 3.42-3.51 (1H, m), 3.62-3.68 (1H, m), 3.75-3.84 (4H, m), 4.08 (2H, s), 5.06-5.17 (2H, m), 7.21-7.27 (3H, m), 7.33 (2H, d, J = 8.2 Hz), 7.93 (2H, d, J = 8.2 Hz)<br>MS (ESI+): 425 [M + Na]⁺ |
|---|---|---|
| Example 42 | (structure) | ¹H-NMR (CD₃OD) δ: 3.08 (2H, td, J = 17.5, 4.6 Hz), 3.39-3.50 (1H, m), 3.59-3.85 (5H, m), 3.99 (2H, s), 5.11 (2H, m), 5.95 (1H, tt, J = 56.5, 4.6 Hz), 7.11-7.34 (7H, m)<br>MS (ESI+): 423 [M + 1]⁺ |

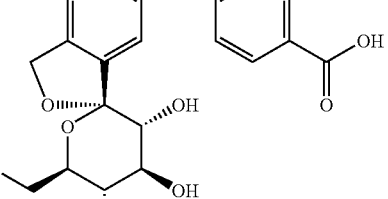
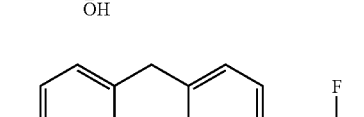

TABLE 1-8-continued
| Example 43 | 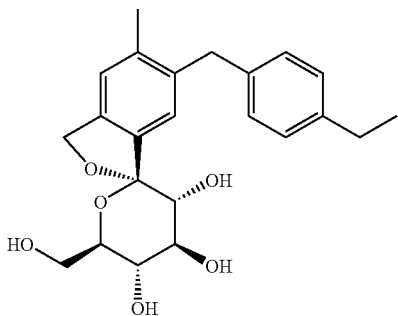 | ¹H-NMR (CDCl₃) δ: 1.17 (3H, t, J = 7.63 Hz), 2.20 (3H, s), 2.54 (1H, brs), 2.56 (2H, q, J = 7.63 Hz), 3.19 (1H, d, J = 7.25 Hz), 3.66-4.00 (8H, m), 4.25 (1H, brs), 4.54 (1H, s), 5.02 (2H, dd, J = 12.69, 17.93 Hz), 6.97 (1H, s), 7.00 (4H, dd, J = 8.01, 12.97 Hz), 7.14 (1H, s)<br>MS (ESI⁺): 423 [M + Na] |
|---|---|---|
| Example 44 | 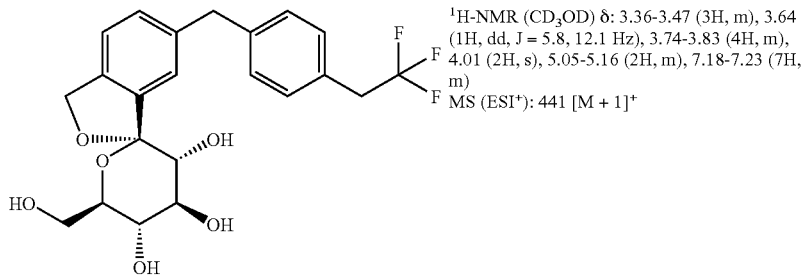 | ¹H-NMR (CD₃OD) δ: 3.36-3.47 (3H, m), 3.64 (1H, dd, J = 5.8, 12.1 Hz), 3.74-3.83 (4H, m), 4.01 (2H, s), 5.05-5.16 (2H, m), 7.18-7.23 (7H, m)<br>MS (ESI⁺): 441 [M + 1]⁺ |
| Example 45 | 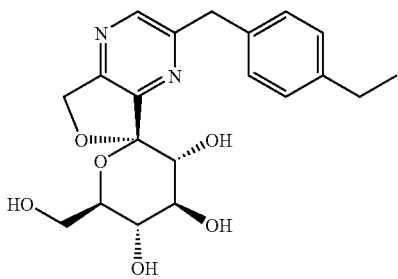 | |
TABLE 1-9
| Example 46 | 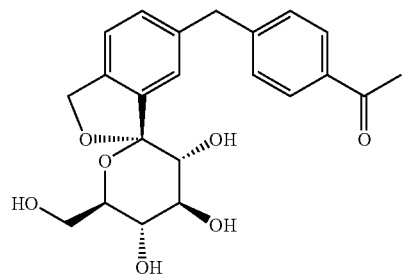 | ¹H-NMR (CD₃OD) δ: 2.56 (3H, s), 3.41-3.47 (1H, m), 3.64 (1H, dd, J = 5.8, 12.1 Hz), 3.73-3.83 (4H, m), 4.08 (2H, s), 5.10 (2H, dd, J = 12.6, 19.8 Hz), 7.22-7.25 (3H, m), 7.33-7.36 (2H, m), 7.87-7.91 (2H, m)<br>MS (ESI⁺): 401 [M + 1]⁺ |
|---|---|---|
| Example 47 | 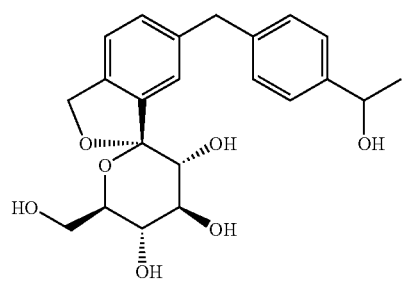 | ¹H-NMR (CD₃OD) δ: 1.41 (3H, d, J = 6.59 Hz), 3.40-3.47 (1H, m), 3.61-3.67 (1H, m), 3.74-3.83 (4H, m), 3.98 (2H, s), 4.74-4.81 (1H, m), 5.04-5.15 (2H, m), 7.15-7.27 (7H, m)<br>MS (ESI⁺): 425 [M + Na]⁺ |

Test Example 1

Evaluation of Inhibitory Activity Against methyl-α-D-glucopyranoside uptake of human Na⁺-glucose cotransporter (SGLT1 and SGLT2)

1) Construction of Human SGLT1 Expression Vector

Human SGLT1 cDNA was amplified by PCR with a cDNA library derived from human small intestine (Clontech) as a template, synthetic DNA primers and KOD+ DNA Polymerase (Toyobo Co., Ltd., Japan). The amplified cDNA was inserted into pcRII-Topo vector by using a Topo TA Cloning Dual Promoter kit (Invitrogen). E. coli competent cells (Invitrogen, TOP10) were transformed with the plasmid vector, cultured in LB medium containing ampicillin (50 mg/L) to grow ampicillin-resistant clones. The plasmid vector containing human SGLT1 cDNA was purified from the clone in a standard manner (see Maniatis et al., Molecular Cloning). Human SGLT1 cDNA added restriction enzyme recognition sites (Eco RI at 5'-end, Hind III at 3'-end) was amplified by PCR with the plasmid vector as a template, synthetic DNA primers containing an additional restriction enzyme recognition site, and KOD+ DNA Polymerase. This amplified cDNA was digested with Eco RI and Hind III and ligated into expression vector pcDNA3.1(−) (Invitrogen) digested with Eco RI and Hind III by a Rapid DNA Ligation kit (Roche Diagonostics). E. coli competent cells (Invitrogen, DH5α) were transformed with the ligated expression vector and grown in ampicillin-containing LB medium. Human SGLT1 expression vector was purified from the ampicillin-resistant clone in a standard manner.

2) Construction of Human SGLT2 Expression Vector

Human SGLT2 cDNA was amplified by PCR with a cDNA library derived from human kidney (Clontech) as a template, synthetic DNA primers and KOD+ DNA Polymerase. The amplified cDNA was inserted into pcRII-Topo vector by using a Topo TA Cloning Dual Promoter kit. E. coli competent cells (TPO10) were transformed with the plasmid vector, cultured in LB medium containing ampicillin (50 mg/L) to grow ampicillin-resistant clones. The plasmid vector containing human SGLT2 cDNA was purified from the clone in a standard manner. Human SGLT2 cDNA added restriction enzyme recognition sites (Xho I at 5'-end, Hind III at 3'-end) was amplified by PCR with the plasmid vector as a template, synthetic DNA primers containing an additional restriction enzyme recognition site and KOD+ DNA Polymerase. This amplified cDNA was digested with Xho I and Hind III, and ligated into expression vector pcDNA3.1(−) digested with Xho I and Hind III by using a Rapid DNA Ligation kit. E. coli competent cells (DH5α) were transformed with the ligated expression vector and grown in ampicillin-containing LB medium. Human SGLT2 expression vector was purified from the ampicillin-resistant clone in a standard manner.

3) Establishment of Cell Lines Stably Expressing Human SGLT1 or Human SGLT2

The human SGLT1 expression vector or the human SGLT2 expression vector was digested with the restriction enzyme Pvu I and transfected into CHO-K1 cells with FuGENE (Roche Diagonostics). After the transfection, the cells were cultured at 37° C. in the presence of 5% $CO_2$ for about 3 weeks in DMEM medium (Gibco) containing penicillin (50 U/mL, SIGMA), streptomycin (50 mg/L, SIGMA), geneticin (200 mg/L, Nacalai Tesque, Inc., Japan) and 20% fetal bovine serum to obtain geneticin-resistant clones. Among these clones, clones stably expressing human SGLT1 or human SGLT2 were selected by the evaluating the sodium-dependent uptake activity of sugar (methyl-α-D-glucopyranoside).

4) Evaluation of Inhibitory Activity Against methyl-α-D-glucopyranoside Uptake

Cell lines stably expressing human SGLT1 or human SGLT2 CHO were seeded in 96-well culture plates at a density of 30000 to 40000 cells/well and cultured for 4 to 6 days. The medium in these plates was removed and replaced by 150 μL/well pretreatment buffer (i.e., a buffer containing 140 mM choline chloride, 2 mM potassium chloride, 1 mM calcium chloride, 1 mM magnesium chloride, 10 mM 2-[4-(2-hydroxyethyl)-1-piperazinyl]ethanesulfonic acid and tris(hydroxymethyl)aminomethane, pH 7.4), and the plates were incubated at 37° C. for 20 minutes. The pretreatment buffer in the plates was removed, replaced by 50 μL/well fresh pretreatment buffer, and the plates were incubated at 37° C. for 20 minutes. Methyl-α-D-(U-$^{14}$C)glucopyranoside (6.3 mL, Amersham Pharmacia Biotech, 200 mCi/L) was added to and mixed with 100 mL buffer (i.e., a buffer containing 140 mM sodium chloride, 2 mM potassium chloride, 1 mM calcium chloride, 1 mM magnesium chloride, 1 mM methyl-α-D-glucopyranoside, 10 mM [4-(2-hydroxyethyl)-1-piperazinyl]ethanesulfonic acid and tris(hydroxymethyl)aminomethane, pH 7.4), which was used as uptake buffer. Test compounds were dissolved into uptake buffer and these test compound solutions were used for evaluating inhibitory activity. Uptake buffer without a test compound was used as a control solution. Moreover, for use in measuring baseline uptake in the absence of sodium, sodium-free solution was prepared in the same manner to contain 140 mM choline chloride instead of sodium chloride. The pretreatment buffer was removed from each well of the plates and replaced by 35 μL/well test compound solutions, control solution or sodium-free solution, and the plates were incubated at 37° C. for 45 minutes. The solutions were removed and replaced by 300 μL/well washing buffer (i.e., a buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethanesulfonic acid and tris(hydroxymethyl)aminomethane, pH 7.4). The washing buffer was removed immediately. This washing procedure was repeated once again, and a cell lysis solution (1 M sodium hydroxide, 0.1% sodium lauryl sulfate) was added in a volume of 30 μL per well to solubilize the cells. 2 M hydrochloric acid (15 μL) was added to the cell lysate in each well, and 40 μL of the resulting solution was transferred to a LumaPlate (Packard). The LumaPlate were left overnight at room temperature to evaporate the solvent. The samples on the plate were measured for their radioactivity with a Top-Count NXT (Packard). Assuming that the value obtained by subtracting the baseline uptake level from the uptake level of the control sample was set to 100%, the concentration required for a test compounds to cause 50% inhibition of the uptake level ($IC_{50}$ value) were calculated from the concentration-dependent inhibition curve using ELfit ver. 3. As a result, the compounds of the present invention were found to show a remarkable inhibitory effect on SGLT2. The following table shows the $IC_{50}$ values of representative compounds of the present invention, as measured for SGLT2 inhibition.

TABLE 2

| Test compound | $IC_{50}$ (nM) |
|---|---|
| Example 1 | 4.2 |
| Example 2 | 4.0 |
| Example 4 | 5.0 |

INDUSTRIAL APPLICABILITY

The present invention enables the provision of spiroketal compounds, prodrugs thereof or pharmaceutically acceptable salts thereof, which have an excellent inhibitory effect on SGLT2 activity. The compounds of the present invention are also effective as prophylactic or therapeutic agents for diabetes, diabetes-related disease or diabetic complications.

The invention claimed is:

1. A compound of Formula (I):

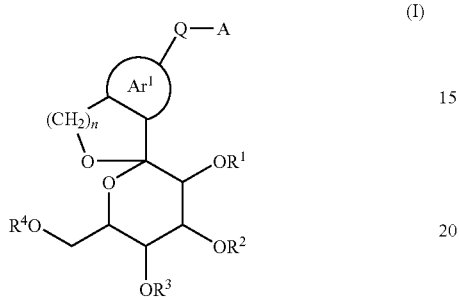

wherein $R^1$, $R^2$, $R^3$ and $R^4$ are each independently selected from a hydrogen atom, a $C_1$-$C_6$ alkyl group which may be substituted with one or more Ra, a $C_7$-$C_{14}$ aralkyl group which may be substituted with one or more $R^b$, and —C(=O)Rx;

Rx represents a $C_1$-$C_6$ alkyl group which may be substituted with one or more Ra, an aryl group which may be substituted with one or more Rb, a heteroaryl group which may be substituted with one or more Rb, a $C_1$-$C_6$ alkoxy group which may be substituted with one or more Ra, or —NReRf;

$Ar^1$ represents an aromatic carbocyclic ring which may be substituted with one or more substituents, or an aromatic heterocyclic ring which may be substituted with one or more substituents;

wherein the substituent optionally present on $Ar^1$ is independently selected from a $C_1$-$C_6$ alkyl group which may be substituted with one or more Rc, a $C_3$-$C_8$ cycloalkyl group which may be substituted with one or more Rc, a $C_2$-$C_6$ alkenyl group which may be substituted with one or more Rc, a $C_2$-$C_6$ alkynyl group which ma be substituted with one or more Rc, a $C_7$-$C_{14}$ aralkyl group which may be substituted with one or more Rd, a halogen atom, a hydroxyl group, a cyano group, a nitro group, a carboxyl group, a $C_1$-$C_6$ alkoxy, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkylcarbonyl group which may be substituted with one or more Rc, a $C_1$-$C_6$ alkoxycarbonyl group which may be substituted with one or more Rc, a $C_1$-$C_3$ alkylenedioxy group, a heterocyclyl group, and a heterocyclyloxy group;

Q represents —$(CH_2)_m$-$(L)_p$- or -$(L)_p$-$(CH_2)_m$—;

m represents an integer selected from 0 to 2, n represents an integer selected from 1 and 2, and p represents an integer selected from 0 and 1;

L represents —O—, —S— or —$NR^5$—, $R^5$ is selected from a hydrogen atom, a $C_1$-$C_6$ alkyl group which may be substituted with one or more Ra, and —C(=O)Rx;

A represents an aryl group which may be substituted with one or more Rb or a heteroaryl group which may be substituted with one or more Rb, wherein the aryl group or the heteroaryl group may form a condensed ring together with an aromatic carbocyclic ring or an aromatic heterocyclic ring;

Ra is independently selected from a halogen atom, a hydroxyl group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkoxycarbonyl group which may be substituted with one or more Rc, and a $C_1$-$C_6$ alkylcarbonyl group which may be substituted with one or more Rc;

Rb is independently selected from a $C_1$-$C_6$ alkyl group which may be substituted with one or more Rc, a $C_3$-$C_8$ cycloalkyl group which may be substituted with one or more Rc, a $C_2$-$C_6$ alkenyl group which may be substituted with one or more Rc, a $C_2$-$C_6$ alkynyl group which may be substituted with one or more Rc, a $C_7$-$C_{14}$ aralkyl group which may be substituted with one or more Rd, a halogen atom, a hydroxyl group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkylcarbonyl group which may be substituted with one or more Rc, a $C_1$-$C_6$ alkoxycarbonyl group which may be substituted with one or more Rc, a $C_1$-$C_3$ alkylenedioxy group, a heterocyclyl group, and a heterocyclyloxy group;

Rc is independently selected from a halogen atom, a hydroxyl group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamino group, and a di-($C_1$-$C_6$ alkyl)amino group;

Rd is independently selected from a $C_1$-$C_6$ alkyl group which may be substituted with one or more halogen atoms, a $C_7$-$C_{14}$ aralkyl group, a halogen atom, a hydroxyl group, a cyano group, a nitro group, an amino group, a $C_1$-$C_6$ alkylamino group, and a di-($C_1$-$C_6$ alkyl) amino group;

Re represents a hydrogen atom, a $C_1$-$C_6$ alkyl group which may be substituted with one or more Rc, an aryl group which may be substituted with one or more Rd, or a heteroaryl group which may be substituted with one or more Rd;

Rf represents a hydrogen atom or a $C_1$-$C_6$ alkyl group which may be substituted with one or more Rc; and Rg represents a hydrogen atom, a $C_1$-$C_6$ alkyl group which may be substituted with Rc, a $C_1$-$C_6$ alkylcarbonyl group which may be substituted with one or more Rc, an aryl group which may be substituted with one or more Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc, or, Re and Rf, or Rr and Rg may form a 4- to 7-membered heterocyclic ring together with the nitrogen atom to which they are attached, or a pharmaceutically acceptable salt thereof.

2. The compound according to claim 1, wherein $R^1$, $R^2$, $R^3$ and $R^4$ are each independently selected from a hydrogen atom and —C(=O)Rx, and Rx is a $C_1$-$C_6$ alkyl group which may be substituted with one or more Ra or a $C_1$-$C_6$ alkoxy group which may be substituted with one or more Ra, or a pharmaceutically acceptable salt thereof.

3. The compound according to claim 1, wherein $R^1$, $R^2$, $R^3$ and $R^4$ are each a hydrogen atom, or a pharmaceutically acceptable salt thereof.

4. The compound according to claim 1, wherein $Ar^1$ is a phenylene group or a thienylene group, each of which may be substituted with one or more Rb, or a pharmaceutically acceptable salt thereof.

5. The compound according to claim 1, wherein m is 1 and p is 0, or a pharmaceutically acceptable salt thereof.

6. The compound according to claim 1, wherein n is 1, or a pharmaceutically acceptable salt thereof.

7. The compound according to claim 1, wherein $Ar^1$ has the substituent—Q-A on its ring atom that is 2 atoms apart from the ring atom directly attached to the substituted glucitol group, or a pharmaceutically acceptable salt thereof.

8. The compound according to claim 1, which is represented by Formula (Ia):

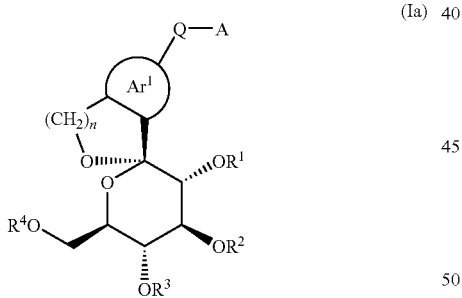

or a pharmaceutically acceptable salt thereof.

9. A compound selected from the group consisting of:
1,1-anhydro-1-C-[5-(4-ethylphenyl)methyl-2-(hydroxymethyl)phenyl]-β-D-glucopyranose,
1,1-anhydro-1-C-[5-(2-benzothiophenyl)methyl-2-(hydroxymethyl)phenyl]-β-D-glucopyranose,
1,1-anhydro-1-C-[5-(4-methoxyphenyl)methyl-2-(hydroxymethyl)phenyl]-β-D-glucopyranose,
1,1-anhydro-1-C-[5-(4-isopropylphenyl)methyl-2-(hydroxymethyl)phenyl]-β-D-glucopyranose,
1,1-anhydro-1-C-[5-(4-cyclopropylphenyl)methyl-2-(hydroxymethyl)phenyl]-β-D-glucopyranose,
1,1-anhydro-1-C-[5-(4-n-propylphenyl)methyl-2-(hydroxymethyl)phenyl]-β-D-glucopyranose,
1,1-anhydro-1-C-[5-(4-ethylphenyloxy)-2-(hydroxymethyl)phenyl]-β-D-glucopyranose,
1,1-anhydro-1-C-[5-(4-ethylphenyl)methyl-2-(2-hydroxyethyl)thiophen-3-yl]-β-D-glucopyranose,
1,1-anhydro-1-C-[5-(4-biphenyl)methyl-2-hydroxymethyl]phenyl]-β-D-glucopyranose,
1,1-anhydro-1-C-[5-(4-((S)-tetrahydrofuran-3-yloxy)phenyl)methyl-2-(hydroxymethyl)phenyl]-β-D-glucopyranose,
1,1-anhydro-1-C-[5-(4-((R)-tetrahydrofuran-3-yloxy)phenyl)methyl-2-(hydroxymethyl)phenyl]-β-D-glucopyranose,
1,1-anhydro-1-C-[5-(4-ethynylphenyl)methyl-2-(hydroxymethyl)phenyl]-β-D-glucopyranose,
1,1-anhydro-1-C-[5-(4-hydroxyphenyl)methyl-2-(hydroxymethyl)phenyl]-β-D-glucopyranose,
1,1-anhydro-1-C-[5-(4-pyrazol-1-ylphenyl)methyl-2-(hydroxymethyl)phenyl]-β-D-glucopyranose,
1,1-anhydro-1-C-[5-(4-methoxyphenyl)ethyl-2-(hydroxymethyl)phenyl]-β-D-glucopyranose,
1,1-anhydro-1-C-[5-(4-methylphenyl)methyl-2-(hydroxymethyl)phenyl]-β-D-glucopyranose,
1,1-anhydro-1-C-[5-(3-acetamidophenyl)methyl-2-(hydroxymethyl)phenyl]-β-D-glucopyranose,
1,1-anhydro-1-C-[5-(3,4-methylenedioxyphenyl)methyl-2-(hydroxymethyl)phenyl]-β-D-glucopyranose,
1,1-anhydro-1-C-[5-(4-cyanophenyl)methyl-2-(hydroxymethyl)phenyl]-β-D-glucopyranose,
1,1-anhydro-1-C-[5-(3,4-dichlorophenyl)methyl-2-(hydroxymethyl)phenyl]-β-D-glucopyranose,
1,1-anhydro-1-C-[5-(4-ethoxyphenyl)methyl-2-(hydroxymethyl)phenyl]-β-D-glucopyranose,
1,1-anhydro-1-C-[5-(4-trifluoromethylphenyl)methyl-2-(hydroxymethyl)phenyl]-β-D-glucopyranose,
1,1-anhydro-1-C-[5-(4-trifluoromethoxyphenyl)methyl-2-(hydroxymethyl)phenyl]-β-D-glucopyranose,
1,1-anhydro-1-C-[5-(4-methylsulfanylphenyl)methyl-2-(hydroxymethyl)phenyl]-β-D-glucopyranose,
1,1-anhydro-1-C-[5-(4-chlorophenyl)methyl-2-(hydroxymethyl)phenyl]-β-D-glucopyranose,
1,1-anhydro-1-C-[5-(naphthalen-2-yl)methyl-2-(hydroxymethyl)phenyl]-β-D-glucopyranose,
1,1-anhydro-1-C-[5-(4-hydroxymethylphenyl)methyl-2-(hydroxymethyl)phenyl]-β-D-glucopyranose,
1,1-anhydro-1-C-[5-(4-fluorophenyl)methyl-2-(hydroxymethyl)phenyl]-β-D-glucopyranose,
1,1-anhydro-1-C-[5-(2-methylphenyl)methyl-2-(hydroxymethyl)phenyl]-β-D-glucopyranose,
1,1-anhydro-1-C-[5-(3-methylphenyl)methyl-2-(hydroxymethyl)phenyl]-β-D-glucopyranose,
1,1-anhydro-1-C-[5-(3-benzyloxyphenyl)methyl-2-(hydroxymethyl)phenyl]-β-D-glucopyranose,
1,1-anhydro-1-C-[5-(2,4-difluorophenyl)methyl-2-(hydroxymethyl)phenyl]-β-D-glucopyranose,
1,1-anhydro-1-C-[5-(4-(2-fluoroethyl)phenyl)methyl-2-(hydroxymethyl)phenyl]-β-D-glucopyranose,
1,1-anhydro-1-C-[5-(pyridin-3-yl)methyl-2-(hydroxymethyl)phenyl]-β-D-glucopyranose,
1,1-anhydro-1-C-[5-(4-methanesulfonylphenyl)methyl-2-(hydroxymethyl)phenyl]-β-D-glucopyranose,
1,1-anhydro-1-C-[5-(pyridin-4-yl)methyl-2-(hydroxymethyl)phenyl]-β-D-glucopyranose,
1,1-anhydro-1-C-[5-(1H-indol-2-yl)methyl-2-(hydroxymethyl)phenyl]-β-D-glucopyranose,
1,1-anhydro-1-C-[5-(3-hydroxyphenyl)methyl-2-(hydroxymethyl)phenyl]-β-D-glucopyranose,
1,1-anhydro-1-C-[5-(4-vinylphenyl)methyl-2-(hydroxymethyl)phenyl]-β-D-glucopyranose, 1,1-anhydro-1-C-[5-(4-methoxycarbonylphenyl)methyl-2-(hydroxymethyl)phenyl]-β-D-glucopyranose,
1,1-anhydro-1-C-[5-(4-carboxyphenyl)methyl-2-(hydroxymethyl)phenyl]-β-D-glucopyranose, and
1,1-anhydro-1-C-[5-(4-(2,2-difluoroethyl)phenyl)methyl-2-(hydroxymethyl)phenyl]-β-D-glucopyranose,
1,1-anhydro-1-C-[5-(4-ethylphenyl)methyl-2-(hydroxymethyl)-4-methylphenyl]-β-D-glucopyranose,
1,1-anhydro-1-C-[5-(4-(2,2,2-trifluoroethyl)phenyl)methyl-2-(hydroxymethyl)phenyl]-β-D-glucopyranose,
1,1-anhydro-1-C-[5-(4-ethylphenyl)methyl-2-(hydroxymethyl)pyrazin-3-yl]-β-D-glucopyranose,
1,1-anhydro-1-C-[5-(4-acetylphenyl)methyl-2-(hydroxymethyl)phenyl]-β-D-glucopyranose, and
1,1-anhydro-1-C-[5-(4-(1-hydroxyethyl)phenyl)methyl-2-(hydroxymethyl)phenyl]-β-D-glucopyranose,
or a pharmaceutically acceptable salt thereof.

10. A compound of Formula (Ib):

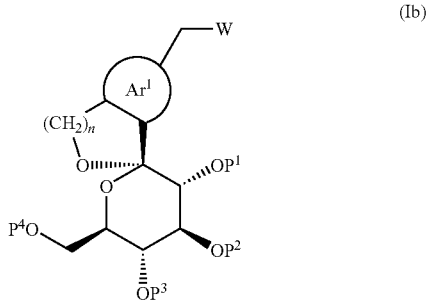

(Ib)

wherein n represents an integer selected from 1 and 2;
$Ar^1$ represents an aromatic carbocyclic ring which may be substituted with one or more Rb, or an aromatic heterocyclic ring which may be substituted with one or more Rb;
W represents —O—Z or a halogen atom;
Z represents a hydrogen atom, an acyl group or a benzyl group;
$P^1$, $P^2$, $P^3$ and $P^4$ are each independently selected from a hydrogen atom, an acyl group or a benzyl group; and
Rb is as defined in claim 1.

11. A pharmaceutical composition for use as an $Na^+$-glucose cotransporter inhibitor, which comprises the compound according to claim 1, or a pharmaceutically acceptable salt thereof.

12. A pharmaceutical composition for use in treating diabetes, hyperglycemia, diabetic complications induced thereby, or obesity, which comprises the compound according to any one of claims 1 to 9, or a pharmaceutically acceptable salt thereof.

13. The pharmaceutical composition according to claim 12, wherein diabetes is insulin-dependent diabetes mellitus (type I diabetes) or non-insulin-dependent diabetes mellitus (type II diabetes).

14. A method for treating diabetes, hyperglycemia-induced diabetic complications or obesity, which comprises administering to a patient a therapeutically effective amount of the compound according to claim 1, or a pharmaceutically acceptable salt thereof.

15. The method according to claim 14, wherein diabetes is insulin-dependent diabetes mellitus (type I diabetes) or non-insulin-dependent diabetes mellitus (type II diabetes).

16. A compound according to claim 1, which is 1,1-anhydro-1-C-[5-(4-ethylphenyl)methyl-2-(hydroxymethyl)phenyl]-β-D-glucopyranose, or a pharmaceutically acceptable salt thereof.

17. A method of claim 14, wherein said compound is 1,1-anhydro-1-C-[5-(4-ethylphenyl)methyl-2-(hydroxymethyl)phenyl]-β-D-glucopyranose, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,767,651 B2 | |
| APPLICATION NO. | : 11/815074 | |
| DATED | : August 3, 2010 | |
| INVENTOR(S) | : Takamitsu Kobayashi | |

It is certified that error appears in the above-identified patent and that said Letters Patent is hereby corrected as shown below:

Claim 1, column 65, line 27, delete "$R^b$" and insert --$R_b$--;
Claim 1, column 65, line 44, delete "ma be" and insert --maybe--.
Claim 1, column 65, line 48, after "C1-C6 alkoxy", add --group--.
Claim 1, column 67, line 12, delete "Rr" and insert --Rf--.
Claim 4, column 67, line 27, delete "Rb" and insert --substituents:
  wherein the substituent optionally present on Ar1 is independently selected from a C1-C6 alkyl group which may be substituted with one or more Rc, a C3-C8 cycloalkyl group which may be substituted with one or more Rc, a C2-C6 alkenyl group which may be substituted with one or more Rc, a C2-C6 alkynyl group which may be substituted with one or more Rc, a C7-C14 aralkyl group which may be substituted with one or more Rd, a halogen atom, a hydroxyl group, a cyano group, a nitro group, a carboxyl group, a C1-C6 alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a C1-C6 alkylthio group which may be substituted with one or more Rc, a C1-C6 alkylsulfinyl group which may be substituted with one or more Rc, a C1-C6 alkylsulfonyl group which may be substituted with one or more Rc, -NRfRg, a C1-C6 alkylcarbonyl group which may be substituted with one or more Rc, a C1-C6 alkoxycarbonyl group which may be substituted with one or more Rc, a C1-C3 alkylenedioxy group, a heterocyclyl group, and a heterocyclyloxy group;

Rc is independently selected from a halogen atom, a hydroxyl group, a cyano group, a nitro group, a carboxyl group, a C1-C6 alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a C1-C6 alkylamino group, and a di (C1-C6 alkyl)amino group;

Rd is independently selected from a C1-C6 alkyl group which may be substituted with one or more halogen atoms, a C7 C14 aralkyl group, a halogen atom, a hydroxyl group, a cyano group, a nitro group, an amino group, a C1-C6 alkylamino group, and a di-(C1-C6 alkyl)amino group;

Signed and Sealed this
Twenty-fourth Day of July, 2012

David J. Kappos
*Director of the United States Patent and Trademark Office*

Rf represents a hydrogen atom or a C1-C6 alkyl group which may be substituted with one or more Rc; and Rg represents a hydrogen atom, a C1-C6 alkyl group which may be substituted with Rc, a C1-C6 alkylcarbonyl group which may be substituted with one or more Rc, an aryl group which may be substituted with one or more Rd, a heteroaryl group which may be substituted with one or more Rd, a carbamoyl group, a C1-C6 alkoxycarbonyl group which may be substituted with one or more Rc, or a C1-C6 alkylsulfonyl group which may be substituted with one or more Rc, or, Rf and Rg may form a 4- to 7-membered heterocyclic ring together with the nitrogen atom to which they are attached,--

Claim 10, column 70, line 5, after "benzyl group; and" insert

--Rb is independently selected from a C1-C6 alkyl group which may be substituted with one or more Rc, a C3-C8 cycloalkyl group which may be substituted with one or more Rc, a C2-C6 alkenyl group which may be substituted with one or more Rc, a C2-C6 alkynyl group which may be substituted with one or more Rc, a C7-C14 aralkyl group which may be substituted with one or more Rd, a halogen atom, a hydroxyl group, a cyano group, a nitro group, a carboxyl group, a C1-C6 alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a C1-C6 alkylthio group which may be substituted with one or more Rc, a C1-C6 alkylsulfinyl group which may be substituted with one or more Rc, a C1-C6 alkylsulfonyl group which may be substituted with one or more Rc, -NRfRg, a C1-C6 alkylcarbonyl group which may be substituted with one or more Rc, a C1-C6 alkoxycarbonyl group which may be substituted with one or more Rc, a C1-C3 alkylenedioxy group, a heterocyclyl group, and a heterocyclyloxy group;

Rc is independently selected from a halogen atom, a hydroxyl group, a cyano group, a nitro group, a carboxyl group, a C1-C6 alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a C1-C6 alkylamino group, and a di (C1-C6 alkyl)amino group;
Rd is independently selected from a C1-C6 alkyl group which may be substituted with one or more halogen atoms, a C7 C14 aralkyl group, a halogen atom, a hydroxyl group, a cyano group, a nitro group, an amino group, a C1-C6 alkylamino group, and a di-(C1-C6 alkyl)amino group;

Rf represents a hydrogen atom or a C1-C6 alkyl group which may be substituted with one or more Rc; and Rg represents a hydrogen atom, a C1-C6 alkyl group which may be substituted with Rc, a C1-C6 alkylcarbonyl group which may be substituted with one or more Rc, an aryl group which may be substituted with one or more Rd, a heteroaryl group which may be substituted with one or more Rd, a carbamoyl group, a C1-C6 alkoxycarbonyl group which may be substituted with one or more Rc, or a C1-C6 alkylsulfonyl group which may be substituted with one or more Rc, or, Rf and Rg may form a 4- to 7-membered heterocyclic ring together with the nitrogen atom to which they are attached.--

Claim 12, column 70, line 14, remove the multiple dependency by deleting "any of", and "or 9".

UNITED STATES PATENT AND TRADEMARK OFFICE
CERTIFICATE OF CORRECTION

PATENT NO.           : 7,767,651 B2                                 Page 1 of 3
APPLICATION NO.      : 11/815074
DATED                : August 3, 2010
INVENTOR(S)          : Takamitsu Kobayashi et al.

It is certified that error appears in the above-identified patent and that said Letters Patent is hereby corrected as shown below:

In the Claims:

Claim 1, column 65, line 27, delete "$R^b$" and insert --Rb--
Claim 1, column 65, line 44, delete "ma be" and insert -- rnay be--
Claim 1, column 65, line 48, after "$C_1$-$C_6$ alkoxy", add --group--
Claim 1, column 67, line 12, delete "Rr" and insert --Rf--
Claim 4, column 67, line 27, delete "Rb" and insert –substituents:
wherein the substituent optionally present on $Ar^1$ is independently selected from a $C_1$-$C_6$ alkyl group which may be substituted with one or more Rc, a $C_3$-$C_8$ cycloalkyl group which may be substituted with one or more Rc, a $C_2$-$C_6$ alkenyl group which may be substituted with one or more Rc, a $C_2$-$C_6$ alkynyl group which may be substituted with one or more Rc, a $C_7$-$C_{14}$ aralkyl group which may be substituted with one or more Rd, a halogen atom, a hydroxyl group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, -NRfRg, a $C_1$-$C_6$ alkylcarbonyl group which may be substituted with one or more Rc, a $C_1$-$C_6$ alkoxycarbonyl group which may be substituted with one or more Rc, a $C_1$-$C_3$ alkylenedioxy group, a heterocyclyl group, and a heterocyclyloxy group;

This certificate supersedes the Certificate of Correction issued July 24, 2012.

Signed and Sealed this
Twenty-fourth Day of September, 2013

Teresa Stanek Rea
*Deputy Director of the United States Patent and Trademark Office*

Rc is independently selected from a halogen atom, a hydroxyl group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamine group, and a di-($C_1$-$C_6$ alkyl)amino group;

Rd is independently selected from a $C_1$-$C_6$ alkyl group which may be substituted with one or more halogen atoms, a $C_7$-$C_{14}$ aralkyl group, a halogen atom, a hydroxyl group, a cyano group, a nitro group, an amino group, a $C_1$-$C_6$ alkylamine group, and a di-($C_1$-$C_6$ alkyl)amino group;

Rf represents a hydrogen atom or a $C_1$-$C_6$ alkyl group which may be substituted with one or more Rc; and Rg represents a hydrogen atom, a $C_1$-$C_6$ alkyl group which may be substituted with Rc, a $C_1$-$C_6$ alkylcarbonyl group which may be substituted with one or more Rc, an aryl group which may be substituted with one or more Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc, or, Rf and Rg may form a 4- to 7-membered heterocyclic ring together with the nitrogen atom to which they are attached,--

Claim 10, column 70, line 6, delete "Rb is as defined in claim 1." and insert:

--Rb is independently selected from a $C_1$-$C_6$ alkyl group which may be substituted with one or more Rc, a $C_3$-$C_8$ cycloalkyl group which may be substituted with one or more Rc, a $C_2$-$C_6$ alkenyl group which may be substituted with one or more Rc, a $C_2$-$C_6$ alkynyl group which may be substituted with one or more Rc, a $C_7$-$C_{14}$ aralkyl group which may be substituted with one or more Rd, a halogen atom, a hydroxyl group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, -NRfRg, a $C_1$-$C_6$ alkylcarbonyl group which may be substituted with one or more Rc, a $C_1$-$C_6$ alkoxycarbonyl group which may be substituted with one or more Rc, a $C_1$-$C_3$ alkylenedioxy group, a heterocyclyl group, and a heterocyclyloxy group;

Rc is independently selected from a halogen atom, a hydroxyl group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamine group, and a di-($C_1$-$C_6$ alkyl)amino group;

CERTIFICATE OF CORRECTION (continued)

U.S. Pat. No. 7,767,651 B2

Rd is independently selected from a $C_1$-$C_6$ alkyl group which may be substituted with one or more halogen atoms, a $C_7$ $C_{14}$ aralkyl group, a halogen atom, a hydroxyl group, a cyano group, a nitro group, an amino group, a $C_1$-$C_6$ alkylamine group, and a di-($C_1$-$C_6$ alkyl)amino group;

Rf represents a hydrogen atom or a $C_1$-$C_6$ alkyl group which may be substituted with one or more Rc; and Rg represents a hydrogen atom, a $C_1$-$C_6$ alkyl group which may be substituted with Rc, a $C_1$-$C_6$ alkylcarbonyl group which may be substituted with one or more Rc, an aryl group which may be substituted with one or more Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc, or, Rf and Rg may form a 4- to 7 -membered heterocyclic ring together with the nitrogen atom to which they are attached.--

Claim 12, column 70, line 14, delete "any one of claims 1 to 9," and insert "claim 1,".